(12) United States Patent
Freyne et al.

(10) Patent No.: US 7,514,445 B2
(45) Date of Patent: Apr. 7, 2009

(54) HETEROARYL AMINES AS GLYCOGEN SYNTHASE KINASE 3β INHIBITORS (GSK3 INHIBITORS)

(75) Inventors: Eddy Jean Edgard Freyne, Rumst (BE); Peter Jacobus Johannes Antonius Buijnsters, Breda (NL); Marc Willems, Vosselaar (BE); Werner Constant Johan Embrechts, Beerse (BE); Christopher John Love, Deurne (BE); Paul Adriaan Jan Janssen, Vosselaar (BE); Paulus Joannes Lewi, Turnhout (BE); Jan Heeres, Vosselaar (BE); Marc René de Jonge, Tilburg (NL); Lucien Maria Henricus Koymans, Retie (BE); Hendrik Maarten Vinkers, Antwerp (BE); Koen Jeanne Alfons Van Aken, Kortrijk (BE); Gaston Stanislas Marcella Diels, Ravels (BE)

(73) Assignee: Janssen Pharmaceutica N.V., Beerse (BE)

( * ) Notice: Subject to any disclaimer, the term of this patent is extended or adjusted under 35 U.S.C. 154(b) by 569 days.

(21) Appl. No.: 10/493,452

(22) PCT Filed: Oct. 29, 2002

(86) PCT No.: PCT/EP02/12077

§ 371 (c)(1),
(2), (4) Date: Apr. 23, 2004

(87) PCT Pub. No.: WO03/037891

PCT Pub. Date: May 8, 2003

(65) Prior Publication Data
US 2005/0004125 A1     Jan. 6, 2005

(30) Foreign Application Priority Data
Nov. 1, 2001   (EP) .................. 01204196

(51) Int. Cl.
| | | |
|---|---|---|
| A61K 31/506 | (2006.01) | |
| A61P 3/10 | (2006.01) | |
| A61P 25/28 | (2006.01) | |
| A61P 25/02 | (2006.01) | |
| C07D 403/06 | (2006.01) | |
| C07D 403/12 | (2006.01) | |
| C07D 403/14 | (2006.01) | |

(52) U.S. Cl. .............. 514/272; 514/275; 544/328; 544/331
(58) Field of Classification Search ............... 544/331, 544/328; 514/275, 272
See application file for complete search history.

(56) References Cited

U.S. PATENT DOCUMENTS 4,966,622 A    10/1990   Rempfler et al. ............... 71/92

(Continued)

FOREIGN PATENT DOCUMENTS

EP        0 164 204 A1    12/1985

(Continued)

OTHER PUBLICATIONS

Cecil Textbook of Medicine, edited by Bennet, J.C., and Plum F., 20th edition, vol. 1, 1004-1010, 1996.*

(Continued)

*Primary Examiner*—Venkataraman Balasubramanian
(74) *Attorney, Agent, or Firm*—Woodcock Washburn LLP

(57) ABSTRACT

This invention concerns a compound of formula

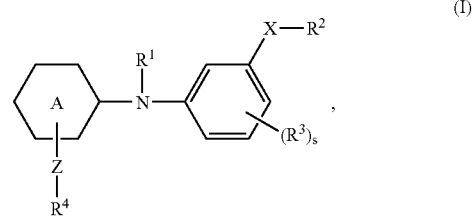

(I)

a N-oxide, a pharmaceutically acceptable addition salt, a quaternary amine and a stereochemically isomeric form thereof, wherein ring A is a 6-membered heterocycle; $R^1$ is hydrogen; aryl; formyl; $C_{1-6}$alkylcarbonyl; optionally substituted $C_{1-6}$alkyl; $C_{1-6}$alkyloxycarbonyl; optionally substituted $C_{1-6}$alkyloxy$C_{1-6}$alkylcarbonyl; X is a direct bond or a linker atom or group; Z is a direct bond or a linker atom or group; $R^2$ is hydrogen, $C_{1-10}$alkyl, $C_{2-10}$alkenyl, $C_{2-10}$alkynyl, a carbocycle or a heterocycle, each of said groups may optionally be substituted; $R^3$ is hydrogen; hydroxy; halo; optionally substituted $C_{1-6}$alkyl or $C_{2-6}$alkenyl or $C_{2-6}$alkynyl; $C_{1-6}$alkyloxy; $C_{1-6}$alkylthio; $C_{1-6}$alkyloxycarbonyl; $C_{1-6}$alkylcarbonyloxy; carboxyl; cyano; nitro; amino; mono- or di($C_{1-6}$alkyl)amino; polyhalo$C_{1-6}$alkyl; polyhalo$C_{1-6}$alkyloxy; polyhalo$C_{1-6}$alkylthio; $R^{21}$; $R^{21}$—$C_{1-6}$alkyl; $R^{21}$—O—; $R^{21}$—S—; $R^{21}$—C(=O)—; $R^{21}$—S(=O)$_p$—; $R^7$—S(=O)$_p$—; $R^7$—S(=O)$_p$—NH—; $R^{21}$—S(=O)$_p$—NH—; $R^7$—C(=O)—; —NHC(=O)H; —C(=O)NHNH$_2$; $R^7$—C(=O)—NH—; $R^{21}$—C(=O)—NH—; —C(=NH)$R^7$—C(=NH)$R^{21}$; $R^4$ is an optionally substituted heterocycle provided that —X—$R^2$ and/or $R^3$ is other than hydrogen; their use, pharmaceutical compositions comprising them and processes for their preparation.

8 Claims, No Drawings

U.S. PATENT DOCUMENTS

| | | | |
|---|---|---|---|
| 5,516,775 A | 5/1996 | Zimmermann et al. | 514/224.2 |
| 5,521,184 A | 5/1996 | Zimmermann | 514/252 |
| 5,728,708 A | 3/1998 | Zimmermann | 514/275 |
| 5,958,935 A | 9/1999 | Davis et al. | 514/275 |
| 6,417,185 B1 | 7/2002 | Goff et al. | 514/235.8 |
| 6,441,053 B1 | 8/2002 | Klein et al. | 514/789 |
| 2002/0065270 A1 | 5/2002 | Moriarty et al. | 514/218 |

FOREIGN PATENT DOCUMENTS

| | | |
|---|---|---|
| EP | 0 337 943 A2 | 10/1989 |
| EP | 0 233 461 B1 | 3/1996 |
| EP | 0 834 507 B1 | 5/2004 |
| WO | 91/18887 A1 | 12/1991 |
| WO | 95/09853 A1 | 4/1995 |
| WO | WO 9509851 A1 * | 4/1995 |
| WO | 97/19065 A1 | 5/1997 |
| WO | 97/41854 A1 | 11/1997 |
| WO | 98/18782 A1 | 5/1998 |
| WO | WO 9841512 A1 * | 9/1998 |
| WO | 99/50250 A1 | 10/1999 |
| WO | 99/65897 A1 | 12/1999 |
| WO | 00/27825 A1 | 5/2000 |
| WO | 00/62778 A1 | 10/2000 |
| WO | 01/12621 A1 | 2/2001 |
| WO | 01/29009 A1 | 4/2001 |
| WO | 01/47897 A1 | 7/2001 |
| WO | WO 0160816 A1 * | 8/2001 |
| WO | WO 0172745 A1 * | 10/2001 |

OTHER PUBLICATIONS

Patel et al. Biochem. Soc. Trans. 32(5), 803-808,2004.*
Jope et al., Trends in Biochemical Sciences, 20(2): 95-102, 2004.*
Cohen et al., Nature Reviews/Molecular Biology 2: 769-776, 2001.*
Hers, I. et al., "The protein kinase C inhibitors bisindolylmaleimide I (GF 109203x) and IX (Ro 31-8220) are potent inhibitors of glycogen synthase kinase-3 activity," *FEBS Letters*, 1999, 460, 433-436.
Smith, D. G. et al., "3-Anilino-4-arylmaleimides: Potent and Selective Inhibitors of Glycogen Synthase Kinase-3 (GSK-3)," *Bioorganic & Medicinal Chemistry Letters*, 2001, 11, 635-639.

* cited by examiner

HETEROARYL AMINES AS GLYCOGEN SYNTHASE KINASE 3β INHIBITORS (GSK3 INHIBITORS)

CROSS REFERENCE TO RELATED APPLICATIONS

This application is the national stage of Application No. PCT/EP02/12077, filed Oct. 29, 2002, which application claims priority from EP 01204196.8 filed Nov. 1, 2001.

The present invention concerns a novel group of heterocyclic derivatives, their use as a medicine, their use for the manufacture of a medicament for the treatment of diseases mediated through glycogen synthase kinase 3; processes for their preparation and pharmaceutical compositions comprising them.

SUMMARY OF THE INVENTION

WO 01/72745 describes 2-substituted 4-heteroaryl-pyrimidines useful in the treatment of proliferative disorders.

WO 98/41512 relates to substituted 2-anilinopyrimidines useful as protein kinase inhibitors.

WO 95/09851 describes pyrimidineamine derivatives useful in the treatment of tumour diseases.

WO 01/12621 describes inhibitors of c-JUN-N-terminal kinases and other protein kinases.

WO 01/60816 describes pyrimidine derivatives useful as kinase inhibitors.

WO 97/19065 discloses substituted 2-anilinopyrimidines useful as $p56^{lck}$, $p59^{fyn}$, ZAP-70 and protein kinase C inhibitors.

WO 91/18887 discloses diaminopyrimidine compounds as inhibitors of gastric acid secretion.

WO 99/50250 concerns HIV inhibiting aminopyrimidine derivatives.

U.S. Pat. No. 5,516,775 concerns the use of 2-anilinopyrimidines as protein kinase C inhibitors.

WO 95/09853 describes N-phenyl-2-pyrimidineamine derivatives for the treatment of tumor diseases.

WO 98/18782 concerns 2-pyrimidineamine derivatives as selective protein tyrosine kinase inhibitors.

EP 0,337,943 discloses N-phenyl-N-pyrimidin-2-yl derivatives having herbicidal plant growth regulating activity.

EP 0,164,204 concerns 2-aminopyrimidines which augment the immune respons.

EP 0,233,461 relates to 4,5,6-substituted 2-pyrimidineamines having anti-asthmatic activity.

WO 00/62778 describes cyclic protein tyrosine kinase inhibitors.

U.S. Pat. No. 5,521,184 describes pyrimidine derivatives for the treatment of tumoral diseases.

The present invention relates to compounds which are distinguishable from the prior art in structure, pharmacological activity, potency or selectivity.

DETAILED DESCRIPTION OF THE INVENTION

The present invention concerns a compound of formula (I)

a N-oxide, a pharmaceutically acceptable addition salt, a quaternary amine and a stereochemically isomeric form thereof, wherein ring A is pyridyl, pyrimidinyl, pyrazinyl or pyridazinyl;

$R^1$ is hydrogen; aryl; formyl; $C_{1-6}$alkylcarbonyl; $C_{1-6}$alkyl; $C_{1-6}$alkyloxycarbonyl; $C_{1-6}$alkyl substituted with formyl, $C_{1-6}$alkylcarbonyl, $C_{1-6}$alkyloxycarbonyl, $C_{1-6}$alkylcarbonyloxy; $C_{1-6}$alkyloxy$C_{1-6}$alkylcarbonyl optionally substituted with $C_{1-6}$alkyloxycarbonyl;

X is —NR$^1$—; —NH—NH—; —N=N—; —O—; —C(=O)—; —C(=S)—; —O—C(=O)—; —C(=O)—O—; —O—C(=O)—$C_{1-6}$alkyl-; —C(=O)—O—$C_{1-6}$alkyl-; —O—$C_{1-6}$alkyl-C(=O)—; —C(=O)—$C_{1-6}$alkyl-O—; —O—C(=O)—NR$^1$—; —NR$^1$—C(=O)—O—; —O—C(=O)—C(=O)—; —C(=O)—NR$^1$—, —NR$^1$—C(=O)—; —C(=S)—NR$^1$—, —NR$^1$—C(=S)—; —NR$^1$—C(=O)—NR$^1$—; —NR$^1$—C(=S)—NR$^1$—; —NR$^1$—S(=O)—NR$^1$—; —NR$^1$—S(=O)$_2$—NR$^1$—; —$C_{1-6}$alkyl-C(=O)—NR$^1$—; —O—$C_{1-6}$alkyl-C(=O)—NR$^1$—; —$C_{1-6}$alkyl-O—C(=O)—NR$^1$—; —$C_{1-6}$alkyl-; —O—$C_{1-6}$alkyl-; —$C_{1-6}$alkyl-O—; —NR$^1$—$C_{1-6}$alkyl-; —$C_{1-6}$alkyl-NR$^1$—; —NR$^1$—$C_{1-6}$alkyl-NR$^1$—; —NR$^1$—$C_{1-6}$alkyl-$C_{3-7}$cycloalkyl-; —$C_{2-6}$alkenyl-; —$C_{2-6}$alkynyl-; —O—$C_{2-6}$alkenyl-; —$C_{2-6}$alkenyl-O—; —NR$^1$—$C_{2-6}$alkenyl-; —$C_{2-6}$alkenyl-NR$^1$—; —NR$^1$—$C_{2-6}$alkenyl-NR$^1$—; —NR$^1$—$C_{2-6}$alkenyl-$C_{3-7}$cycloalkyl-; —O—$C_{2-6}$alkynyl-; —$C_{2-6}$alkynyl-O—; —NR$^1$—$C_{2-6}$alkynyl-; —$C_{2-6}$alkynyl-NR$^1$—; —NR$^1$—$C_{2-6}$alkynyl-NR$^1$—; —NR$^1$—$C_{2-6}$alkynyl-$C_{3-7}$cycloalkyl-; —O—$C_{1-6}$alkyl-O—; —O—$C_{2-6}$alkenyl-O—; —O—$C_{2-6}$alkynyl-O—; —CHOH—; —S—; —S(=O)—; —S(=O)$_2$—; —S(=O)—NR$^1$—; —S(=O)$_2$—NR$^1$—; —NR$^1$—S(=O)—; —NR$^1$—S(=O)$_2$—; —S—$C_{1-6}$alkyl-; —$C_{1-6}$alkyl-S—; —S—$C_{2-6}$alkenyl-; —$C_{2-6}$alkenyl-S—; —S—$C_{2-6}$alkynyl-; —$C_{2-6}$alkynyl-S—; —O—$C_{1-6}$alkyl-S(=O)$_2$— or a direct bond;

Z is a direct bond, $C_{1-6}$alkanediyl, $C_{2-6}$alkenediyl, $C_{2-6}$alkynediyl; —O—; —O—$C_{1-6}$alkyl-; —S—; —C(=O)—; —C(=O)—O—; —O—C(=O)—; —C(=S)—; —S(=O)—; —S(=O)$_2$—; —NR$^1$—; —NR$^1$—$C_{1-6}$alkyl-; —NR$^1$—C(=O)—; —O—C(=O)—NR$^1$—; —NR$^1$C(=O)—O—; —NR$^1$—C(=S)—; —S(=O)—NR$^1$—; —S(=O)$_2$—NR$^1$—; —NR$^1$—S(=O)—; —NR$^1$—S(=O)$_2$—; —NR$^1$—C(=O)—NR$^1$—; —NR$^1$—C(=S)—NR$^1$—; —NR$^1$—S(=O)—NR$^1$—; —NR$^1$—S(=O)$_2$—NR$^1$—;

$R^2$ is hydrogen, $C_{1-10}$alkyl, $C_{2-10}$alkenyl, $C_{2-10}$alkynyl, $R^{20}$, each of said groups representing $R^2$ may optionally be substituted where possible with one or more substituents each independently being selected from =S; =O; $R^{15}$;

hydroxy; halo; nitro; cyano; $R^{15}$—O—; SH; $R^{15}$—S—; formyl; carboxyl; $R^{15}$—C(=O)—; $R^{15}$—O—C(=O)—; $R^{15}$—C(=O)—O—; $R^{15}$—O—C(=O)—O—; —SO$_3$H; $R^{15}$—S(=O)—; $R^{15}$—S(=O)$_2$—; $R^5R^6N$; $R^5R^6N$—C$_{1-6}$alkyl; $R^5R^6N$—C$_{3-7}$cycloalkyl; $R^5R^6N$—C$_{1-6}$alkyloxy; $R^5R^6N$—C(=O)—; $R^5R^6N$—C(=S)—; $R^5R^6N$—C(=O)—NH—; $R^5R^6N$—C(=S)—NH—; $R^5R^6N$—S(=O)—O—; $R^5R^6N$—S(=O)$_n$—NH—; $R^{15}$—C(=S)—; $R^{15}$—C(=O)—NH—; $R^{15}$—O—C(=O)—NH—; $R^{15}$—S(=O)$_n$—NH—; $R^{15}$—O—S(=O)$_n$—NH—; $R^{15}$—C(=S)—NH—; $R^{15}$—O—C(=S)—NH—; $R^{17}R^{18}N$—Y$_{1a}$—; $R^{17}R^{18}N$—Y$_2$—NR$^{16}$—Y$_1$—; $R^{15}$—Y$_2$—NR$^{19}$—Y$_1$—; H—Y$_2$—NR$^{19}$—Y$_1$—;

$R^3$ is hydrogen; hydroxy; halo; C$_{1-6}$alkyl; C$_{1-6}$alkyl substituted with cyano, hydroxy or —C(=O)R$^7$; C$_{2-6}$alkenyl; C$_{2-6}$alkenyl substituted with one or more halogen atoms or cyano; C$_{2-6}$alkynyl; C$_{2-6}$alkynyl substituted with one or more halogen atoms or cyano; C$_{1-6}$alkyloxy; C$_{1-6}$alkylthio; C$_{1-6}$alkyloxycarbonyl; C$_{1-6}$alkylcarbonyloxy; carboxyl; cyano; nitro; amino; mono- or di(C$_{1-6}$alkyl)amino; polyhaloC$_{1-6}$alkyl; polyhaloC$_{1-6}$alkyloxy; polyhaloC$_{1-6}$alkylthio; $R^{21}$; $R^{21}$—C$_{1-6}$alkyl; $R^{21}$—O—; $R^{21}$—S—; $R^{21}$—C(=O)—; $R^{21}$—S(=O)$_p$—; $R^7$—S(=O)$_p$—; $R^7$—S(=O)$_p$—NH—; $R^{21}$—S(=O)$_p$—NH—; $R^7$—C(=O)—; —NHC(=O)H; —C(=O)NHNH$_2$; $R^7$—C(=O)—NH—; $R^{21}$—C(=O)—NH—; —C(=NH)R$^7$; —C(=NH)R$^7$;

$R^4$ is a monocyclic, bicyclic or tricyclic saturated heterocycle; a monocyclic, bicyclic or tricyclic partially saturated heterocycle or a monocyclic, bicyclic or tricyclic aromatic heterocycle, each of said heterocycles optionally being substituted where possible with one or more substituents each independently being selected from =S; =O; $R^{15}$; hydroxy; halo; nitro; cyano; $R^{15}$—O—; SH; $R^{15}$—S—; formyl; carboxyl; $R^{15}$—C(=O)—; $R^{15}$—O—C(=O)—; $R^{15}$—C(=O)—O—; $R^{15}$—O—C(=O)—O—; —SO$_3$H; $R^{15}$—S(=O)—; $R^{15}$—S(=O)$_2$—; $R^5R^6N$; $R^5R^6NC_{1-6}$alkyl; $R^5R^6NC_{3-7}$cycloalkyl; $R^5R^6NC_{1-6}$alkyloxy; $R^5R^6N$—C(=O)—; $R^5R^6N$—C(=S)—; $R^5R^6N$—C(=O)—NH—; $R^5R^6N$—C(=S)—NH—; $R^5R^6N$—S(=O)$_n$—; $R^5R^6N$—S(=O)$_n$—NH—; $R^{15}$—C(=S)—; $R^{15}$—C(=O)—NH—; $R^{15}$—O—C(=O)—NH—; $R^{15}$—S(=O)$_n$—NH—; $R^{15}$—O—S(=O)$_n$—NH—; $R^{15}$—C(=S)—NH—; $R^{15}$—O—C(=S)—NH—; $R^{17}R^{18}N$—Y$_{1a}$—; $R^{17}R^{18}N$—Y$_2$—NR$^{16}$—Y$_1$—; $R^{15}$—Y$_2$—NR$^{19}$—Y$_1$—; H—Y$_2$—NR$^{19}$—Y$_1$—;

$R^5$ and $R^6$ each independently are hydrogen, $R^8$, —Y$_1$—NR$^9$—Y$_2$—NR$^{10}R^{11}$, —Y$_1$—NR$^9$—Y$_1$—R$^8$, —Y$_1$—NR$^9R^{10}$, or $R^5$ and $R^6$ may together with the nitrogen to which they are attached form a saturated or partially saturated monocyclic 3 to 8 membered heterocycle or an aromatic 4 to 8 membered monocyclic heterocycle, each of said heterocycles may optionally be substituted with one or more substituents selected from $R^{12}$, $R^{13}$ and $R^{14}$, or each of said heterocycles may optionally be fused with a benzene ring, said benzene ring being optionally substituted with one or more substituents selected from $R^{12}$, $R^{13}$ and $R^{14}$;

$R^7$ is C$_{1-6}$alkyl, C$_{1-6}$alkyloxy, amino, mono- or di(C$_{1-6}$alkyl)amino or polyhaloC$_{1-6}$alkyl;

$R^8$ is C$_{1-6}$alkyl; C$_{2-6}$alkenyl; C$_{2-6}$alkynyl; a monocyclic, bicyclic or tricyclic saturated carbocycle; a monocyclic, bicyclic or tricyclic partially saturated carbocycle; a monocyclic, bicyclic or tricyclic aromatic carbocycle; a monocyclic, bicyclic or tricyclic saturated heterocycle; a monocyclic, bicyclic or tricyclic partially saturated heterocycle; a monocyclic, bicyclic or tricyclic aromatic heterocycle; C$_{1-6}$alkyl substituted with a monocyclic, bicyclic or tricyclic saturated carbocycle or with a monocyclic, bicyclic or tricyclic partially saturated carbocycle or with a monocyclic, bicyclic or tricyclic aromatic carbocycle or with a monocyclic, bicyclic or tricyclic saturated heterocycle or with a monocyclic, bicyclic or tricyclic partially saturated heterocycle or with a monocyclic, bicyclic or tricyclic aromatic heterocycle; each of said groups representing $R^8$ may optionally be substituted with one or more substituents selected from $R^{12}$, $R^{13}$ and $R^{14}$;

$R^9$, $R^{10}$ and $R^{11}$ each independently are hydrogen or $R^8$, or any two of $R^9$, $R^{10}$ and $R^{11}$ may together be C$_{1-6}$alkanediyl or C$_{2-6}$alkenediyl thereby forming a saturated or partially saturated monocyclic 3 to 8 membered heterocycle or an aromatic 4 to 8 membered monocyclic heterocycle together with the nitrogen atoms to which they are attached, each of said heterocycles may optionally be substituted with one or more substituents selected from $R^{12}$, $R^{13}$ and $R^{14}$;

$R^{12}$, $R^{13}$ and $R^{14}$ each independently are hydrogen; $R^{15}$; hydroxy; halo; nitro; cyano; $R^{15}$—O—; SH; $R^{15}$—S—; formyl; carboxyl; $R^{15}$—C(=O)—; $R^{15}$—O—C(=O)—; $R^{15}$—C(=O)—O—; $R^{15}$—O—C(=O)—O—; —SO$_3$H; $R^{15}$—S(=O)—; $R^{15}$—S(=O)$_2$—; $R^{15}R^{16}N$—S(=O)—; $R^{15}R^{16}N$—S(=O)$_2$—; $R^{17}R^{18}N$—Y$_1$—; $R^{17}R^{18}N$—Y$_2$—NR$^{16}$—Y$_1$—; $R^{15}$—Y$_2$—NR$^{19}$—Y$_1$—; H—Y$_2$—NR$^{19}$—Y$_1$—; oxo, or any two of $R^{12}$, $R^{13}$ and $R^{14}$ may together be C$_{1-6}$alkanediyl or C$_{2-6}$alkenediyl thereby forming a saturated or partially saturated monocyclic 3 to 8 membered carbo— or heterocycle or an aromatic 4 to 8 membered monocyclic carbo— or heterocycle together with the atoms to which they are attached, or any two of $R^{12}$, $R^{13}$ and $R^{14}$ may together be —O—(CH$_2$)$_r$—O— thereby forming a saturated, partially saturated or aromatic monocyclic 4 to 8 membered carbo— or heterocycle together with the atoms to which they are attached;

$R^{15}$ is C$_{1-6}$alkyl, C$_{2-6}$alkenyl, C$_{2-6}$alkynyl, a monocyclic, bicyclic or tricyclic saturated carbocycle; a monocyclic, bicyclic or tricyclic partially saturated carbocycle; a monocyclic, bicyclic or tricyclic aromatic carbocycle; a monocyclic, bicyclic or tricyclic saturated heterocycle; a monocyclic, bicyclic or tricyclic partially saturated heterocycle; a monocyclic, bicyclic or tricyclic aromatic heterocycle; C$_{1-6}$alkyl substituted with a monocyclic, bicyclic or tricyclic saturated carbocycle or with a monocyclic, bicyclic or tricyclic partially saturated carbocycle or with a monocyclic, bicyclic or tricyclic aromatic carbocycle or with a monocyclic, bicyclic or tricyclic saturated heterocycle or with a monocyclic, bicyclic or tricyclic partially saturated heterocycle or with a monocyclic, bicyclic or tricyclic aromatic heterocycle; each of said substituents representing $R^{15}$ may optionally be substituted with one or more substituents selected from $R^{12}$, $R^{13}$ and $R^{14}$; or each of said carbocycles or heterocycles may optionally be fused with a benzene ring, said benzene ring being optionally substituted with one or more substituents selected from $R^{12}$, $R^{13}$ and $R^{14}$;

$R^{16}$, $R^{17}$, $R^{18}$ and $R^{19}$ each independently are hydrogen or $R^{15}$, or $R^{17}$ and $R^{18}$, or $R^{15}$ and $R^{19}$ may together be C$_{1-6}$alkanediyl or C$_{2-6}$alkenediyl thereby forming a saturated or partially saturated monocyclic 3 to 8 membered heterocycle or an aromatic 4 to 8 membered monocyclic heterocycle, each of said heterocycles may optionally be substituted with one or more substituents selected from $R^{12}$, $R^{13}$ and $R^{14}$; or R¹⁷ and R¹⁸ together with R¹⁶ may be $C_{1-6}$alkanediyl or $C_{2-6}$alkenediyl thereby forming a saturated or partially saturated monocyclic 3 to 8 membered heterocycle or an aromatic 4 to 8 membered monocyclic heterocycle together with the nitrogen atoms to which they are attached, each of said heterocycles may optionally be substituted with one or more substituents selected from $R^{12}$, $R^{13}$ and $R^{14}$;

$R^{20}$ is a monocyclic, bicyclic or tricyclic saturated carbocycle; a monocyclic, bicyclic or tricyclic partially saturated carbocycle; a monocyclic, bicyclic or tricyclic aromatic carbocycle; a monocyclic, bicyclic or tricyclic saturated heterocycle; a monocyclic, bicyclic or tricyclic partially saturated heterocycle; a monocyclic, bicyclic or tricyclic aromatic heterocycle;

$R^{21}$ is a monocyclic, bicyclic or tricyclic saturated carbocycle; a monocyclic, bicyclic or tricyclic partially saturated carbocycle; a monocyclic, bicyclic or tricyclic aromatic carbocycle; a monocyclic, bicyclic or tricyclic saturated heterocycle; a monocyclic, bicyclic or tricyclic partially saturated heterocycle; a monocyclic, bicyclic or tricyclic aromatic heterocycle, each of said carbocycles or heterocycles representing $R^{21}$ may optionally be substituted with one or more substituents selected from $R^{12}$, $R^{13}$ and $R^{14}$;

$Y_{1a}$ is $-Y_3-S(=O)-Y_4-$; $-Y_3-S(=O)_2-Y_4-$, $-Y_3-C(=O)-Y_4-$, $-Y_3-C(=S)-Y_4-$, $-Y_3-O-Y_4-$, $-Y_3-S-Y_4-$, $-Y_3-O-C(=O)-Y_4-$ or $-Y_3-C(=O)-O-Y_4-$;

$Y_1$ or $Y_2$ each independently are a direct bond, $-Y_3-S(=O)-Y_4-$; $-Y_3-S(=O)_2-Y_4-$, $-Y_3-C(=O)-Y_4-$, $-Y_3-C(=S)-Y_4-$, $-Y_3-O-Y_4-$, $-Y_3-S-Y_4-$, $-Y_3-O-C(=O)-Y_4-$ or $-Y_3-C(=O)-O-Y_4-$;

$Y_3$ or $Y_4$ each independently are a direct bond, $C_{1-6}$alkanediyl, $C_{2-6}$alkenediyl or $C_{2-6}$alkynediyl;

n is 1 or 2;
m is 1 or 2;
p is 1 or 2;
r is 1 to 5;
s is 1 to 3;

aryl is phenyl or phenyl substituted with one, two, three, four or five substituents each independently selected from halo, $C_{1-6}$alkyl, $C_{3-7}$cycloalkyl, $C_{1-6}$alkyloxy, cyano, nitro, polyhalo$C_{1-6}$alkyl and polyhalo$C_{1-6}$alkyloxy;

provided that $-X-R^2$ and/or $R^3$ is other than hydrogen; and provided that when

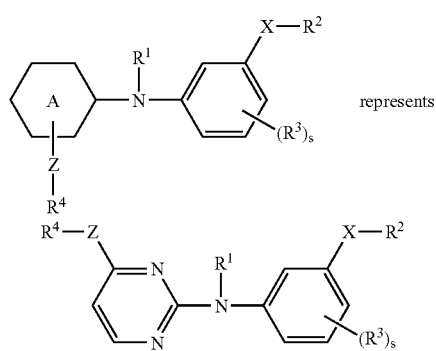 represents then
-Z is other than a direct bond or NH when $R^1$ is hydrogen or methyl, s is 2, $R^3$ is methoxy, and $-X-R^2$ is methoxy;

$-Z-R^4$ is other than 3-pyridyl, 4-pyridyl or 4-pyridyl N-oxide when $R^1$ is hydrogen or methyl, s is 1, $R^3$ is 3-chloro or 4-methoxy, and $-X-R^2$ is hydrogen;

$-Z-R^4$ is other than

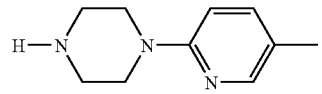

when $R^1$ is hydrogen;

$-R^3$ and $-X-R^2$ are other than hydrogen when $R^1$ is hydrogen and $-Z-R^4$ is 3-pyridyl or substituted 4-pyridyl;

and provided that when

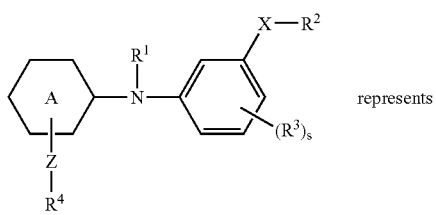 represents

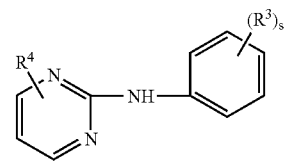

then
$-R^4$ is other than pyridyl optionally substituted with methyl, pyridyl N-oxide, 1-methyl-pyridinium, thienyl optionally substituted with one or two methyl groups, furanyl optionally substituted with one or two methyl groups, benzofuranyl, quinolinyl, indolyl, pyrrolyl optionally substituted with methyl, pyrimidinyl, phenothiazinyl; and provided that the following compounds

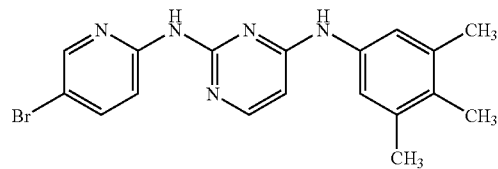

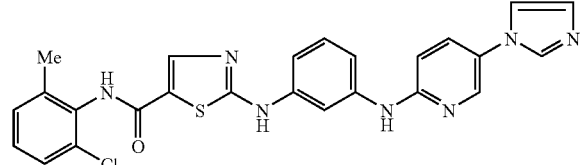

are not included.

The present invention also relates to the use of a compound for the manufacture of a medicament for the prevention or the treatment of diseases mediated through GSK3, said compound being a compound of formula (I')

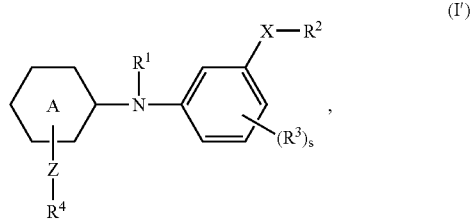

a N-oxide, a pharmaceutically acceptable addition salt, a quaternary amine and a stereochemically isomeric form thereof, wherein ring A is pyridyl, pyrimidinyl, pyrazinyl or pyridazinyl;

$R^1$ is hydrogen; aryl; formyl; $C_{1-6}$alkylcarbonyl; $C_{1-6}$alkyl; $C_{1-6}$alkyloxycarbonyl; $C_{1-6}$alkyl substituted with formyl, $C_{1-6}$alkylcarbonyl, $C_{1-6}$alkyloxycarbonyl, $C_{1-6}$alkylcarbonyloxy; $C_{1-6}$alkyloxy$C_{1-6}$alkylcarbonyl optionally substituted with $C_{1-6}$alkyloxycarbonyl;

X is $-NR^1-$; $-NH-NH-$; $-N=N-$; $-O-$; $-C(=O)-$; $-C(=S)-$; $-O-C(=O)-$; $-C(=O)-O-$; $-O-C(=O)-C_{1-6}$alkyl-; $-C(=O)-O-C_{1-6}$alkyl-; $-O-C_{1-6}$alkyl-C(=O)-; $-C(=O)-C_{1-6}$alkyl-O-; $-O-C(=O)-NR^1-$; $-NR^1-C(=O)-O-$; $-O-C(=O)-C(=O)-$; $-C(=O)-NR^1-$, $-NR^1-C(=O)-$; $-C(=S)-NR^1-$, $-NR^1-C(=S)-$; $-NR^1-C(=O)-NR^1-$; $-NR^1-C(=S)-NR^1-$; $-NR^1-S(=O)-NR^1-$; $-NR^1-S(=O)_2-NR^1-$; $-C_{1-6}$alkyl-C(=O)-NR^1-$; $-O-C_{1-6}$alkyl-C(=O)-NR^1-$; $-C_{1-6}$alkyl-O-C(=O)-NR^1-$; $-C_{1-6}$alkyl-; $-O-C_{1-6}$alkyl-; $-C_{1-6}$alkyl-O-$; $-NR^1-C_{1-6}$alkyl-; $-C_{1-6}$alkyl-NR^1-$; $-NR^1-C_{1-6}$alkyl-NR^1-$; $-NR^1-C_{1-6}$alkyl-$C_{3-7}$cycloalkyl-; $-C_{2-6}$alkenyl-; $-C_{2-6}$alkynyl-; $-O-C_{2-6}$alkenyl-; $-C_{2-6}$alkenyl-O-; $-NR^1-C_{2-6}$alkenyl-; $-C_{2-6}$alkenyl-NR^1-$; $-NR_1-C_{2-6}$alkenyl-NR^1-$; $-NR^1-C_{2-6}$alkenyl-$C_{3-7}$cycloalkyl-; $-O-C_{2-6}$alkynyl-; $-C_{2-6}$alkynyl-O-; $-NR^1-C_{2-6}$alkynyl-; $-C_{2-6}$alkynyl-NR^1-$; $-NR^1-C_{2-6}$alkynyl-NR^1-$; $-NR^1-C_{2-6}$alkynyl-$C_{3-7}$cycloalkyl-; $-O-C_{1-6}$alkyl-O-$; $-O-C_{2-6}$alkenyl-O-; $-O-C_{2-6}$alkynyl-O-; $-CHOH-$; $-S-$; $-S(=O)-$; $-S(=O)_2-$; $-S(=O)-NR^1-$; $-S(=O)_2-NR^1-$; $-NR^1-S(=O)-$; $-NR^1-S(=O)_2-$; $-S-C_{1-6}$alkyl-; $-C_{1-6}$alkyl-S-; $-S-C_{2-6}$alkenyl-; $-C_{2-6}$alkenyl-S-; $-S-C_{2-6}$alkynyl-; $-C_{2-6}$alkynyl-S-; $-O-C_{1-6}$alkyl-S(=O)_2-$ or a direct bond;

Z is a direct bond, $C_{1-6}$alkanediyl, $C_{2-6}$alkenediyl, $C_{2-6}$alkynediyl; $-O-$; $-O-C_{1-6}$alkyl-; $-S-$; $-C(=O)-$; $-C(=O)-O-$; $-O-C(=O)-$; $-C(=S)-$; $-S(=O)-$; $-S(=O)_2-$; $-NR^1-$; $-NR^1-C_{1-6}$alkyl-; $-NR^1-C(=O)-$; $-O-C(=O)-NR^1-$; $-NR^1C(=O)-O-$; $-NR^1-C(=S)-$; $-S(=O)-NR^1-$; $-S(=O)_2-NR^1-$; $-NR^1-S(=O)-$; $-NR^1-C(=O)-NR^1-$; $-NR^1-C(=S)-NR^1-$; $-NR^1-S(=O)-NR^1-$; $-NR^1-S(=O)_2-NR^1-$;

$R^2$ is hydrogen, $C_{1-10}$alkyl, $C_{2-10}$alkenyl, $C_{2-10}$alkynyl, $R^{20}$, each of said groups representing $R^2$ may optionally be substituted where possible with one or more substituents each independently being selected from =S; =O; $R^{15}$; hydroxy; halo; nitro; cyano; $R^{15}-O-$; SH; $R^{15}-S-$; formyl; carboxyl; $R^{15}-C(=O)-$; $R^{15}-O-C(=O)-$; $R^{15}-C(=O)-O-$; $R^{15}-O-C(=O)-O-$; $-SO_3H$; $R^{15}-S(=O)-$; $R^{15}-S(=O)_2-$; $R^5R^6N$; $R^5R^6N-C_{1-6}$alkyl; $R^5R^6N-C_{3-7}$cycloalkyl; $R^5R^6N-C_{1-6}$alkyloxy; $R^5R^6N-C(=O)-$; $R^5R^6N-C(=S)-$; $R^5R^6N-C(=O)-NH-$; $R^5R^6N-C(=S)-NH-$; $R^5R^6N-S(=O)_n-$; $R^5R^6N-S(=O)_n-NH-$; $R^{15}-C(=S)-$; $R^{15}-C(=O)-NH-$; $R^{15}-O-C(=O)-NH-$; $R^{15}-S(=O)_n-NH-$; $R^{15}-O-S(=O), -NH-$; $R^{15}-C(=S)-NH-$; $R^{15}-O-C(=S)-NH-$; $R^{17}R^{18}N-Y_{1a}-$; $R^{17}R^{18}N-Y_2-NR^6-Y_1-$; $R^5-Y_2-NR^{19}-Y_1-$; $H-Y_2-NR^{19}-Y_1-$;

$R^3$ is hydrogen; hydroxy; halo; $C_{1-6}$alkyl; $C_{1-6}$alkyl substituted with cyano, hydroxy or $-C(=O)R^7$; $C_{2-6}$alkenyl; $C_{2-6}$alkenyl substituted with one or more halogen atoms or cyano; $C_{2-6}$alkynyl; $C_{2-6}$alkynyl substituted with one or more halogen atoms or cyano; $C_{1-6}$alkyloxy; $C_{1-6}$alkylthio; $C_{1-6}$alkyloxycarbonyl; $C_{1-6}$alkylcarbonyloxy; carboxyl; cyano; nitro; amino; mono- or di($C_{1-6}$alkyl)amino; polyhalo$C_{1-6}$alkyl; polyhalo$C_{1-6}$alkyloxy; polyhalo$C_{1-6}$alkylthio; $R^{21}$; $R^{21}-C_{1-6}$alkyl; $R^2-O-$; $R^2-S-$; $R^{21}-C(=O)-$; $R^{21}-S(=O)_n-$; $R^7-S(=O)_p-$; $R^7-S(=O)_p-NH-$; $R^2-S(=O)_p-NH-$; $R^7-C(=O)-$; $-NHC(=O)H$; $-C(=O)NHNH_2$; $R^7-C(=O)-NH-$; $R^{21}-C(=O)-NH-$; $-C(=NH)R^7$; $-C(=NH)R^{21}$;

$R^4$ is a monocyclic, bicyclic or tricyclic saturated heterocycle; a monocyclic, bicyclic or tricyclic partially saturated heterocycle or a monocyclic, bicyclic or tricyclic aromatic heterocycle, each of said heterocycles optionally being substituted where possible with one or more substituents each independently being selected from =S; =O; $R^{15}$; hydroxy; halo; nitro; cyano; $R^{15}-O-$; SH; $R^{15}-S-$; formyl; carboxyl; $R^{15}-C(=O)-$; $R^{15}-O-C(=O)-$; $R^{15}-C(=O)-O-$; $R^{15}-O-C(=O)-O-$; $-SO_3H$; $R^{15}-S(=O)-$; $R^{15}-S(=O)_2-$; $R^5R^6N$; $R^5R^6NC_{1-6}$alkyl; $R^5R^6NC_{3-7}$cycloalkyl; $R^5R^6NC_{1-6}$alkyloxy; $R^5R^6N-C(=O)-$; $R^5R^6N-C(=S)-$; $R^5R^6N-C(=O)-NH-$; $R^5R^6N-C(=S)-NH-$; $R^5R^6N-S(=O)_n-$; $R^5R^6N-S(=O)_n, -NH-$; $R^{15}-C(=S)-$; $R^{15}-C(=O)-NH-$; $R^{15}-O-C(=O)-NH-$; $R^{15}-S(=O)_n, -NH-$; $R^5-O-S(=O), -NH-$; $R^{15}-C(=S)-NH-$; $R^{15}-O-C(=S)-NH-$; $R^{17}R^{18}N-Y_{1a}-$; $R^{17}R^{18}N-Y_2-NR^{16}-Y_1-$; $R^{15}-Y_2-NR^{19}-Y_1-$; $H-Y_2-NR^{19}-Y_1-$;

$R^5$ and $R^6$ each independently are hydrogen, $R^8$, $-Y_1-NR^9-Y_2-NR^{10}R^{11}$, $-Y_1-NR^9-Y_1-R^8$, $-Y_1-NR^9R^{10}$, or $R^5$ and $R^6$ may together with the nitrogen to which they are attached form a saturated or partially saturated monocyclic 3 to 8 membered heterocycle or an aromatic 4 to 8 membered monocyclic heterocycle, each of said heterocycles may optionally be substituted with one or more substituents selected from $R^{12}$, $R^{13}$ and $R^{14}$, or each of said heterocycles may optionally be fused with a benzene ring, said benzene ring being optionally substituted with one or more substituents selected from $R^{12}$, $R^{13}$ and $R^{14}$;

$R^7$ is $C_{1-6}$alkyl, $C_{1-6}$alkyloxy, amino, mono- or di($C_{1-6}$alkyl)amino or polyhalo$C_{1-6}$alkyl;

$R^8$ is $C_{1-6}$alkyl; $C_{2-6}$alkenyl; $C_{2-6}$alkynyl; a monocyclic, bicyclic or tricyclic saturated carbocycle; a monocyclic, bicyclic or tricyclic partially saturated carbocycle; a monocyclic, bicyclic or tricyclic aromatic carbocycle; a monocyclic, bicyclic or tricyclic saturated heterocycle; a monocyclic, bicyclic or tricyclic partially saturated heterocycle; a monocyclic, bicyclic or tricyclic aromatic heterocycle; $C_{1-6}$alkyl substituted with a monocyclic, bicyclic or tricyclic saturated carbocycle or with a monocyclic, bicyclic or tricyclic partially saturated carbocycle or with a monocyclic, bicyclic or tricyclic aromatic carbocycle or with a monocyclic, bicyclic or tricyclic saturated heterocycle or with a monocyclic, bicyclic or tricyclic partially saturated heterocycle or with a monocyclic, bicyclic or tricyclic aromatic heterocycle; each of said groups representing $R^8$ may optionally be substituted with one or more substituents selected from $R^{12}$, $R^{13}$ and $R^{14}$;

$R^9$, $R^{10}$ and $R^{11}$ each independently are hydrogen or $R^8$, or any two of $R^9$, $R^{10}$ and $R^{11}$ may together be $C_{1-6}$alkanediyl or $C_{2-6}$alkenediyl thereby forming a saturated or partially saturated monocyclic 3 to 8 membered heterocycle or an aromatic 4 to 8 membered monocyclic heterocycle together with the nitrogen atoms to which they are attached, each of said heterocycles may optionally be substituted with one or more substituents selected from $R^{12}$, $R^{13}$ and $R^{14}$;

$R^{12}$, $R^{13}$ and $R^{14}$ each independently are hydrogen; $R^{15}$; hydroxy; halo; nitro; cyano; $R^{15}$—O—; SH; $R^{15}$—S—; formyl; carboxyl; $R^{15}$—C(=O)—; $R^{15}$—O—C(=O)—; $R^{15}$—C(=O)—O—; $R^{15}$—O—C(=O)—O—; —$SO_3H$; $R^{15}$—S(=O)—; $R^{15}$—S(=O)$_2$—; $R^{15}R^{16}N$—S(=O)—; $R^{15}R^{16}N$—S(=O)$_2$—; $R^{17}R^{18}N$—$Y_1$—; $R^{17}R^{18}N$—$Y_2$—$NR^{16}$—$Y_1$—; $R^{15}$—$Y_2$—$NR^{19}$—$Y_1$—; H—$Y_2$—$NR^{19}$—$Y_1$—; oxo, or any two of $R^{12}$, $R^{13}$ and $R^{14}$ may together be $C_{1-6}$alkanediyl or $C_{2-6}$alkenediyl thereby forming a saturated or partially saturated monocyclic 3 to 8 membered carbo—or heterocycle or an aromatic 4 to 8 membered monocyclic carbo—or heterocycle together with the atoms to which they are attached, or any two of $R^{12}$, $R^{13}$ and $R^{14}$ may together be —O—$(CH_2)_r$—O— thereby forming a saturated, partially saturated or aromatic monocyclic 4 to 8 membered carbo—or heterocycle together with the atoms to which they are attached;

$R^{15}$ is $C_{1-6}$alkyl, $C_{2-6}$alkenyl, $C_{2-6}$alkynyl, a monocyclic, bicyclic or tricyclic saturated carbocycle; a monocyclic, bicyclic or tricyclic partially saturated carbocycle; a monocyclic, bicyclic or tricyclic aromatic carbocycle; a monocyclic, bicyclic or tricyclic saturated heterocycle; a monocyclic, bicyclic or tricyclic partially saturated heterocycle; a monocyclic, bicyclic or tricyclic aromatic heterocycle; $C_{1-6}$alkyl substituted with a monocyclic, bicyclic or tricyclic saturated carbocycle or with a monocyclic, bicyclic or tricyclic partially saturated carbocycle or with a monocyclic, bicyclic or tricyclic aromatic carbocycle or with a monocyclic, bicyclic or tricyclic saturated heterocycle or with a monocyclic, bicyclic or tricyclic partially saturated heterocycle or with a monocyclic, bicyclic or tricyclic aromatic heterocycle; each of said substituents representing $R^{15}$ may optionally be substituted with one or more substituents selected from $R^{12}$, $R^{13}$ and $R^{14}$; or each of said carbocycles or heterocycles may optionally be fused with a benzene ring, said benzene ring being optionally substituted with one or more substituents selected from $R^{12}$, $R^{13}$ and $R^{14}$;

$R^{16}$, $R^{17}$, $R^{18}$ and $R^{19}$ each independently are hydrogen or $R^{15}$, or $R^{17}$ and $R^{18}$, or $R^{15}$ and $R^{19}$ may together be $C_{1-6}$alkanediyl or $C_{2-6}$alkenediyl thereby forming a saturated or partially saturated monocyclic 3 to 8 membered heterocycle or an aromatic 4 to 8 membered monocyclic heterocycle, each of said heterocycles may optionally be substituted with one or more substituents selected from $R^{12}$, $R^{13}$ and $R^{14}$; or $R^{17}$ and $R^{18}$ together with $R^{16}$ may be $C_{1-6}$alkanediyl or $C_{2-6}$alkenediyl thereby forming a saturated or partially saturated monocyclic 3 to 8 membered heterocycle or an aromatic 4 to 8 membered monocyclic heterocycle together with the nitrogen atoms to which they are attached, each of said heterocycles may optionally be substituted with one or more substituents selected from $R^{12}$, $R^{13}$ and $R^{14}$;

$R^{20}$ is a monocyclic, bicyclic or tricyclic saturated carbocycle; a monocyclic, bicyclic or tricyclic partially saturated carbocycle; a monocyclic, bicyclic or tricyclic aromatic carbocycle; a monocyclic, bicyclic or tricyclic saturated heterocycle; a monocyclic, bicyclic or tricyclic partially saturated heterocycle; a monocyclic, bicyclic or tricyclic aromatic heterocycle;

$R^{21}$ is a monocyclic, bicyclic or tricyclic saturated carbocycle; a monocyclic, bicyclic or tricyclic partially saturated carbocycle; a monocyclic, bicyclic or tricyclic aromatic carbocycle; a monocyclic, bicyclic or tricyclic saturated heterocycle; a monocyclic, bicyclic or tricyclic partially saturated heterocycle; a monocyclic, bicyclic or tricyclic aromatic heterocycle, each of said carbocycles or heterocycles representing $R^{21}$ may optionally be substituted with one or more substituents selected from $R^{12}$, $R^{13}$ and $R^{14}$;

$Y_{1a}$ is —$Y_3$—S(=O)—$Y_4$—; —$Y_3$—S(=O)$_2$—$Y_4$—, —$Y_3$—C(=O)—$Y_4$—, —$Y_3$—C(=S)—$Y_4$—, —$Y_3$—O—$Y_4$—, —$Y_3$—S—$Y_4$—, —$Y_3$—O—C(=O)—$Y_4$— or —$Y_3$—C(=O)—O—$Y_4$—;

$Y_1$ or $Y_2$ each independently are a direct bond, —$Y_3$—S(=O)—$Y_4$—; —$Y_3$—S(=O)$_2$—$Y_4$—, —$Y_3$—C(=O)—$Y_4$—, —$Y_3$—C(=S)—$Y_4$—, —$Y_3$—O—$Y_4$—, —$Y_3$—S—$Y_4$—, —$Y_3$—O—C(=O)—$Y_4$— or —$Y_3$—C(=O)—O—$Y_4$—;

$Y_3$ or $Y_4$ each independently are a direct bond, $C_{1-6}$alkanediyl, $C_{2-6}$alkenediyl or $C_{2-6}$alkynediyl;

n is 1 or 2;
m is 1 or 2;
p is 1 or 2;
r is 1 to 5;
s is 1 to 3;

aryl is phenyl or phenyl substituted with one, two, three, four or five substituents each independently selected from halo, $C_{1-6}$alkyl, $C_{3-7}$cycloalkyl, $C_{1-6}$alkyloxy, cyano, nitro, polyhalo$C_{1-6}$alkyl and polyhalo$C_{1-6}$alkyloxy; provided that —X—$R^2$ and/or $R^3$ is other than hydrogen.

As used herein $C_{1-3}$alkyl as a group or part of a group defines straight or branched chain saturated hydrocarbon radicals having from 1 to 3 carbon atoms such as methyl, ethyl, propyl, 1-methylethyl; $C_{1-4}$alkyl as a group or part of a group defines straight or branched chain saturated hydrocarbon radicals having from 1 to 4 carbon atoms such as the groups defined for $C_{1-3}$alkyl and butyl; $C_{1-6}$alkyl as a group or part of a group defines straight or branched chain saturated hydrocarbon radicals having from 1 to 6 carbon atoms such as the groups defined for $C_{1-4}$alkyl and pentyl, hexyl, 2-methylbutyl and the like; $C_{1-10}$alkyl as a group or part of a group defines straight or branched chain saturated hydrocarbon radicals having from 1 to 10 carbon atoms such as the groups defined for $C_{1-6}$alkyl and heptyl, octyl, nonyl, decyl and the like; $C_{1-6}$alkanediyl as a group or part of a group defines bivalent straight or branched chain saturated hydrocarbon radicals having from 1 to 6 carbon atoms such as methylene, 1,2-ethanediyl or 1,2-ethylidene, 1,3-propanediyl or 1,3-propylidene, 1,4-butanediyl or 1,4-butylidene and the like; $C_{2-6}$alkenyl defines straight and branched chain hydrocarbon radicals having from 2 to 6 carbon atoms containing a double bond such as ethenyl, propenyl, butenyl, pentenyl, hexenyl and the like; $C_{2-10}$alkenyl defines straight and branched chain hydrocarbon radicals having from 2 to 10 carbon atoms containing a double bond such as the groups defined for $C_{2-6}$alkenyl and heptenyl, octenyl, nonenyl, decenyl and the like; $C_{2-6}$alkenediyl defines bivalent straight and branched chain hydrocarbon radicals having from 2 to 6 carbon atoms containing one or more double bonds such as ethenediyl, propenediyl, butenediyl, pentenediyl, hexenediyl and the like; $C_{2-6}$alkynyl defines straight and branched chain hydrocarbon radicals having from 2 to 6 carbon atoms containing a triple bond such as ethynyl, propynyl, butynyl, pentynyl, hexynyl and the like; $C_{2-10}$alkynyl defines straight and branched chain hydrocarbon radicals having from 2 to 10 carbon atoms containing a triple bond such as the groups defined for $C_{2-6}$alkynyl and heptynyl, octynyl, nonynyl, decynyl and the like; $C_{2-6}$alkynediyl defines bivalent straight and branched chain hydrocarbon radicals having from 2 to 6 carbon atoms containing a triple bond such as ethynediyl, propynediyl, butynediyl, pentynediyl, hexynediyl and the like; $C_{3-7}$cycloalkyl is generic to cyclopropyl, cyclobutyl, cyclopentyl, cyclohexyl and cycloheptyl; a monocyclic, bicyclic or tricyclic saturated carbocycle represents a ring system consisting of 1, 2 or 3 rings, said ring system being composed of only carbon atoms and said ring system containing only single bonds; a monocyclic, bicyclic or tricyclic partially saturated carbocycle represents a ring system consisting of 1, 2 or 3 rings, said ring system being composed of only carbon atoms and comprising at least, one double bond provided that the ring system is not an aromatic ring system; a monocyclic, bicyclic or tricyclic aromatic carbocycle represents an aromatic ring system consisting of 1, 2 or 3 rings, said ring system being composed of only carbon atoms; the term aromatic is well known to a person skilled in the art and designates cyclically conjugated systems of 4n'30 2 electrons, that is with 6, 10, 14 etc. π-electrons (rule of Hückel; n' being 1, 2,3 etc.); a monocyclic, bicyclic or tricyclic saturated heterocycle represents a ring system consisting of 1, 2 or 3 rings and comprising at least one heteroatom selected from O, N or S, said ring system containing only single bonds; a monocyclic, bicyclic or tricyclic partially saturated heterocycle represents a ring system consisting of 1, 2 or 3 rings and comprising at least one heteroatom selected from O, N or S, and at least one double bond provided that the ring system is not an aromatic ring system; a monocyclic, bicyclic or tricyclic aromatic heterocycle represents an aromatic ring system consisting of 1, 2 or 3 rings and comprising at least one heteroatom selected from O, N or S.

Particular examples of monocyclic, bicyclic or tricyclic saturated carbocycles are cyclopropyl, cyclobutyl, cyclopentyl, cyclohexyl, cycloheptyl, cyclooctyl, bicyclo[4,2,0]octanyl, cyclononanyl, cyclodecanyl, decahydronapthalenyl, tetradecahydroanthracenyl.

Particular examples of monocyclic, bicyclic or tricyclic partially saturated carbocycles are cyclopropenyl, cyclobutenyl, cyclopentenyl, cyclohexenyl, cycloheptenyl, cyclo-octenyl, bicyclo[4,2,0]octenyl, cyclononenyl, cyclodecenyl, octahydronaphthalenyl, 1,2,3,4-tetrahydronaphthalenyl, 1,2,3,4,4a,9,9a,10-octahydro-anthracenyl.

Particular examples of monocyclic, bicyclic or tricyclic aromatic carbocycles are phenyl, naphthalenyl, anthracenyl.

Particular examples of monocyclic, bicyclic or tricyclic saturated heterocycles are tetrahydrofuranyl, pyrrolidinyl, dioxolanyl, imidazolidinyl, thiazolidinyl, tetrahydrothienyl, dihydrooxazolyl, isothiazolidinyl, isoxazolidinyl, oxadiazolidinyl, triazolidinyl, thiadiazolidinyl, pyrazolidinyl, piperidinyl, hexahydropyrimidinyl, hexahydropyrazinyl, dioxanyl, morpholinyl, dithianyl, thiomorpholinyl, piperazinyl, trithianyl, decahydroquinolinyl, octahydroindolyl.

Particular examples of monocyclic, bicyclic or tricyclic partially saturated heterocycles are pyrrolinyl, imidazolinyl, pyrazolinyl, 2,3-dihydrobenzofuranyl, 1,3-benzodioxolyl, 2,3-dihydro-1,4-benzodioxinyl, indolinyl and the like.

Particular examples of monocyclic, bicyclic or tricyclic aromatic heterocycles are azetyl, oxetylidenyl, pyrrolyl, furyl, thienyl, imidazolyl, oxazolyl, isoxazolyl, thiazolyl, isothiazolyl, pyrazolyl, triazolyl, thiadiazolyl, oxadiazolyl, tetrazolyl, pyridyl, pyrimidinyl, pyrazinyl, pyridazinyl, triazinyl, pyranyl, benzofuryl, isobenzofuryl, benzothienyl, isobenzothienyl, indolizinyl, indolyl, isoindolyl, benzoxazolyl, benzimidazolyl, indazolyl, benzisoxazolyl, benzisothiazolyl, benzopyrazolyl, benzoxadiazolyl, benzothiadiazolyl, benzotriazolyl, purinyl, quinolinyl, isoquinolinyl, cinnolinyl, quinolizinyl, phthalazinyl, quinoxalinyl, quinazolinyl, naphthiridinyl, pteridinyl, benzopyranyl, pyrrolopyridyl, thienopyridyl, furopyridyl, isothiazolopyridyl, thiazolopyridyl, isoxazolopyridyl, oxazolopyridyl, pyrazolopyridyl, imidazopyridyl, pyrrolopyrazinyl, thienopyrazinyl, furopyrazinyl, isothiazolopyrazinyl, thiazolopyrazinyl, isoxazolopyrazinyl, oxazolopyrazinyl, pyrazolopyrazinyl, imidazopyrazinyl, pyrrolopyrimidinyl, thienopyrimidinyl, furopyrimidinyl, isothiazolopyrimidinyl, thiazolopyrimidinyl, isoxazolopyrimidinyl, oxazolopyrimidinyl, pyrazolopyrimidinyl, imidazopyrimidinyl, pyrrolopyridazinyl, thienopyridazinyl, furopyridazinyl, isothiazolopyridazinyl, thiazolopyridazinyl, isoxazolopyridazinyl, oxazolopyridazinyl, pyrazolopyridazinyl, imidazopyridazinyl, oxadiazolopyridyl, thiadiazolopyridyl, triazolopyridyl, oxadiazolopyrazinyl, thiadiazolopyrazinyl, triazolopyrazinyl, oxadiazolopyrimidinyl, thiadiazolopyrimidinyl, triazolopyrimidinyl, oxadiazolopyridazinyl, thiadiazolopyridazinyl, triazolopyridazinyl, imidazooxazolyl, imidazothiazolyl, imidazoimidazolyl, isoxazolotriazinyl, isothiazolo-triazinyl, pyrazolotriazinyl, oxazolotriazinyl, thiazolotriazinyl, imidazotriazinyl, oxadiazolotriazinyl, thiadiazolotriazinyl, triazolotriazinyl, carbazolyl, acridinyl, phenazinyl, phenothiazinyl, phenoxazinyl.

Particular examples of 5-membered aromatic heterocycles are pyrrolyl, furyl, thienyl, imidazolyl, oxazolyl, isoxazolyl, thiazolyl, isothiazolyl, pyrazolyl, triazolyl, thiadiazolyl, oxadiazolyl, tetrazolyl.

As used herein before, the term (=O) forms a carbonyl moiety when attached to a carbon atom, a sulfoxide moiety when attached to a sulfur atom and a sulfonyl moiety when two of said terms are attached to a sulfur atom.

The term halo is generic to fluoro, chloro, bromo and iodo. As used in the foregoing and hereinafter, polyhalomethyl as a group or part of a group is defined as mono- or polyhalosubstituted methyl, in particular methyl with one or more fluoro atoms, for example, difluoromethyl or trifluoromethyl; polyhalo$C_{1-6}$alkyl as a group or part of a group is defined as mono- or polyhalosubstituted $C_{1-6}$alkyl, for example, the groups defined in halomethyl, 1,1-difluoro-ethyl and the like. In case more than one halogen atoms are attached to an alkyl group within the definition of polyhalomethyl or polyhalo$C_{1-6}$alkyl, they may be the same or different.

The term heterocycle as in the definition of for instance $R^4$, $R^5$, $R^6$, $R^8$ or $R^{15}$ is meant to include all the possible isomeric forms of the heterocycles, for instance, pyrrolyl also includes 2H-pyrrolyl.

The hereinabove-mentioned carbocycles may be attached to the remainder of the molecule of formula (I) or (I') through any ring carbon as appropriate, if not otherwise specified. Thus, for example, when the partially saturated bicyclic carbocycle is 1,2,3,4-tetrahydronaphthalenyl, it may be 1,2,3,4-tetrahydronaphthalen-1-yl, 1,2,3,4-tetrahydronaphthalen-2-yl and the like.

The hereinabove-mentioned heterocycles may be attached to the remainder of the molecule of formula (I) or (I') through any ring carbon or heteroatom as appropriate, if not otherwise specified. Thus, for example, when the aromatic monocyclic heterocycle is imidazolyl, it may be 1-imidazolyl, 2-imidazolyl, 4-imidazolyl and the like.

When any variable (eg. $R^5$, $R^6$ etc.) occurs more than one time in any constituent, each definition is independent.

Lines drawn into ring systems from substituents indicate that the bond may be attached to any of the suitable ring atoms.

For therapeutic use, salts of the compounds of formula (I) or (I') are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable addition salts as mentioned hereinabove are meant to comprise the therapeutically active non-toxic acid addition salt forms which the compounds of formula (I) or (I') are able to form. The latter can conveniently be obtained by treating the base form with such appropriate acids as inorganic acids, for example, hydrohalic acids, e.g. hydrochloric, hydrobromic and the like; sulfuric acid; nitric acid; phosphoric acid and the like; or organic acids, for example, acetic, propanoic, hydroxyacetic, 2-hydroxypropanoic, 2-oxopropanoic, oxalic, malonic, succinic, maleic, fumaric, malic, tartaric, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form.

The compounds of formula (I) or (I') containing acidic protons may be converted into their therapeutically active non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline, the benzathine, N-methyl-D-glucamine, 2-amino-2-(hydroxymethyl)-1,3-propanediol, hydrabamine salts, and salts with amino acids such as, for example, arginine, lysine and the like. Conversely the salt form can be converted by treatment with acid into the free acid form.

The term addition salt also comprises the hydrates and solvent addition forms which the compounds of formula (I) or (I') are able to form. Examples of such forms are e.g. hydrates, alcoholates and the like.

The term "quaternary amine" as used hereinbefore defines the quaternary ammonium salts which the compounds of formula (I) or (I') are able to form by reaction between a basic nitrogen of a compound of formula (I) or (I') and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

It will be appreciated that some of the compounds of formula (I) or (I') and their N-oxides, addition salts, quaternary amines and stereochemically isomeric forms may contain one or more centers of chirality and exist as stereochemically isomeric forms.

The term "stereochemically isomeric forms" as used hereinbefore defines all the possible stereoisomeric forms which the compounds of formula (I) or (I'), and their N-oxides, addition salts, quaternary amines or physiologically functional derivatives may possess. Unless otherwise mentioned or indicated, the chemical designation of compounds denotes the mixture of all possible stereochemically isomeric forms, said mixtures containing all diastereomers and enantiomers of the basic molecular structure as well as each of the individual isomeric forms of formula (I) or (I') and their N-oxides, salts, solvates or quaternary amines substantially free, i.e. associated with less than 10%, preferably less than 5%, in particular less than 2% and most preferably less than 1% of the other isomers. In particular, stereogenic centers may have the R- or S-configuration; substituents on bivalent cyclic (partially) saturated radicals may have either the cis- or trans-configuration. Compounds encompassing double bonds can have an E or Z-stereochemistry at said double bond. Stereochemically isomeric forms of the compounds of formula (I) or (I') are obviously intended to be embraced within the scope of this invention.

The N-oxide forms of the present compounds are meant to comprise the compounds of formula (I) wherein one or several tertiary nitrogen atoms are oxidized to the so-called N-oxide.

Some of the compounds of formula (I) or (I') may also exist in their tautomeric form (e.g. keto-enol tautomerie). Such forms although not explicitly indicated in the above formula are intended to be included within the scope of the present invention.

Whenever used hereinafter, the term "compounds of formula (I)" or "compounds of formula (I) or (I') is meant to also include their N-oxide forms, their salts, their quaternary amines and their stereochemically isomeric forms. Of special interest are those compounds of formula (I) or (I') which are stereochemically pure.

Particular compounds are those compounds of formula (I) or (I') as defined hereinabove provided that the molecular mass of the compounds is at most 1000 u, in particular at most 800 u, more in particular at most 700 u (u stands for unified atomic mass unit and equals $1.66 \times 10^{-27}$ kg).

Particular compounds are also those compounds of formula (I) or (I') as defined hereinabove provided that when $R^3$ is hydrogen then X is other than —C(=O)—$NR^1$— or —C(=S)—$NR^1$—; and provided that when X is a direct bond and $R^2$ is hydrogen than $R^3$ is other than $R^7$—C(=O)— with $R^7$ representing amino or mono- or di($C_{1-6}$alkyl)amino; and provided that when X is a direct bond and $R^2$ is hydrogen than $R^{21}$ is other than a heterocycle; and provided that when $R^3$ is hydrogen then $R^2$ is other than a heterocycle.

Particular interesting compounds are those compounds of formula (I) or (I') as defined hereinabove, their N-oxides, pharmaceutically acceptable addition salts, quaternary amines and stereochemically isomeric forms thereof, wherein ring A is pyridyl, pyrimidinyl, pyrazinyl or pyridazinyl;

$R^1$ is hydrogen; aryl; formyl; $C_{1-6}$alkylcarbonyl; $C_{1-6}$alkyl; $C_{1-6}$alkyloxycarbonyl; $C_{1-6}$alkyl substituted with formyl, $C_{1-6}$alkylcarbonyl, $C_{1-6}$alkyloxycarbonyl, $C_{1-6}$alkylcarbonyloxy; $C_{1-6}$alkyloxy$C_{1-6}$alkylcarbonyl optionally substituted with $C_{1-6}$alkyloxycarbonyl;

X is $-NR^1-$; $-NH-NH-$; $-N=N-$; $-O-$; $-C(=O)-$; $-C(=S)-$; $-O-C(=O)-$; $-C(=O)-O-$; $-O-C(=O)-C_{1-6}$alkyl-; $-C(=O)-O-C_{1-6}$alkyl-; $-O-C_{1-6}$alkyl-$C(=O)-$; $-C(=O)-C_{1-6}$alkyl-O-; $-O-C(=O)-NR^1-$; $-NR^1-C(=O)-O-$; $-O-C(=O)-C(=O)-$; $-C(=O)-NR^1-$, $-NR^1-C(=O)-$; $-C(=S)-NR^1-$, $-NR^1-C(=S)-$; $-NR^1-C(=O)-NR^1-$; $-NR^1-C(=S)-NR^1-$; $-NR^1-S(=O)-NR^1-$; $-NR^1-S(=O)_2-NR^1-$; $-C_{1-6}$alkyl-$C(=O)-NR^1-$; $-O-C_{1-6}$alkyl-$C(=O)-NR^1-$; $-C_{1-6}$alkyl-O-$C(=O)-NR^1-$; $-C_{1-6}$alkyl-; $-O-C_{1-6}$alkyl-; $-C_{1-6}$alkyl-O-; $-NR^1-C_{1-6}$alkyl-; $-C_{1-6}$alkyl-$NR^1-$; $-NR^1-C_{1-6}$alkyl-$NR^1-$; $-NR^1-C_{1-6}$alkyl-$C_{3-7}$cycloalkyl-; $-C_{2-6}$alkenyl-; $-C_{2-6}$alkynyl-; $-O-C_{2-6}$alkenyl-; $-C_{2-6}$alkenyl-O-; $-NR^1-C_{2-6}$alkenyl-; $-C_{2-6}$alkenyl-$NR^1-$; $-NR^1-C_{2-6}$alkenyl-$NR^1-$; $-NR^1-C_{2-6}$alkenyl-$C_{3-7}$cycloalkyl-; $-O-C_{2-6}$alkynyl-; $-C_{2-6}$alkynyl-O-; $-NR^1-C_{2-6}$alkynyl-; $-C_{2-6}$alkynyl-$NR^1-$; $-NR^1-C_{2-6}$alkynyl-$NR^1-$; $-NR^1-C_{2-6}$alkynyl-$C_{3-7}$cycloalkyl-; $-O-C_{1-6}$alkyl-O-; $-O-C_{2-6}$alkenyl-O-; $-O-C_{2-6}$alkynyl-O-; $-CHOH-$; $-S-$; $-S(=O)-$; $-S(=O)_2-$; $-S(=O)-NR^1-$; $-S(=O)_2-NR^1-$; $-NR^1-S(=O)-$; $-NR^1-S(=O)_2-$; $-S-C_{1-6}$alkyl-; $-C_{1-6}$alkyl-S-; $-S-C_{2-6}$alkenyl-; $-C_{2-6}$alkenyl-S-; $-S-C_{2-6}$alkynyl-; $-C_{2-6}$alkynyl-S-; $-O-C_{1-6}$alkyl-$S(=O)_2-$ or a direct bond;

Z is a direct bond, $C_{1-6}$alkanediyl, $C_{2-6}$alkenediyl, $C_{2-6}$alkynediyl; $-O-$; $-O-C_{1-6}$alkyl-; $-S-$; $-C(=O)-$; $-C(=O)-O-$; $-O-C(=O)-$; $-C(=S)-$; $-S(=O)-$; $-S(=O)_2-$; $-NR^1-$; $-NR^1-C_{1-6}$alkyl-; $-NR^1-C(=O)-$; $-O-C(=O)-NR^1-$; $-NR^1C(=O)-O-$; $-NR^1-C(=S)-$; $-S(=O)-NR^1-$; $-S(=O)_2-NR^1-$; $-NR^1-S(=O)-$; $-NR^1-S(=O)_2-$; $-NR^1-C(=O)-NR^1-$; $-NR^1-C(=S)-NR^1-$; $-NR^1-S(=O)-NR^1-$; $-NR^1-S(=O)_2-NR^1-$;

$R^2$ is hydrogen, $C_{1-10}$alkyl, $C_{2-10}$alkenyl, $C_{2-10}$alkynyl, $R^{20}$, each of said groups representing $R^2$ may optionally be substituted where possible with one or more substituents each independently being selected from =S; =O; $R^{15}$; hydroxy; halo; nitro; cyano; $R^{15}-O-$; SH; $R^{15}-S-$; formyl; carboxyl; $R^{15}-C(=O)-$; $R^{15}-O-C(=O)-$; $R^{15}-C(=O)-O-$; $R^{15}-O-C(=O)-O-$; $-SO_3H$; $R^{15}-S(=O)-$; $R^{15}-S(=O)_2-$; $R^5R^6N$; $R^5R^6N-C_{1-6}$alkyl; $R^5R^6N-C_{3-7}$cycloalkyl; $R^5R^6N-C_{1-6}$alkyloxy; $R^5R^6N-C(=O)-$; $R^5R^6N-C(=S)-$; $R^5R^6N-C(=O)-NH-$; $R^5R^6N-C(=S)-NH-$; $R^5R^6N-S(=O)_n-$; $R^5R^6N-S(=O)_n-NH-$; $R^{15}-C(=S)-$; $R^{15}-C(=O)-NH-$; $R^{15}-O-C(=O)-NH-$; $R^{15}-S(=O)_n-NH-$; $R^{15}-O-S(=O)_n-NH-$; $R^{15}-C(=S)-NH-$; $R^{15}-O-C(=S)-NH-$; $R^{17}R^{18}N-Y_{1a}-$; $R^{17}R^8N-Y_2-NR^6-Y_1-$; $R^5-Y_2-NR^{19}-Y_1-$; $H-Y_2-NR^{19}-Y_1-$;

$R^3$ is hydrogen; hydroxy; halo; $C_{1-6}$alkyl; $C_{1-6}$alkyl substituted with cyano, hydroxy or $-C(=O)R^7$; $C_{2-6}$alkenyl; $C_{2-6}$alkenyl substituted with one or more halogen atoms or cyano; $C_{2-6}$alkynyl; $C_{2-6}$alkynyl substituted with one or more halogen atoms or cyano; $C_{1-6}$alkyloxy; $C_{1-6}$alkylthio; $C_{1-6}$alkyloxycarbonyl; $C_{1-6}$alkylcarbonyloxy; carboxyl; cyano; nitro; amino; mono- or di($C_{1-6}$alkyl)amino; polyhalo$C_{1-6}$alkyl; polyhalo$C_{1-6}$alkyloxy; polyhalo$C_{1-6}$alkylthio; $R^{21}$; $R^{21}-C_{1-6}$alkyl; $R^{21}-O-$; $R^{21}-S-$; $R^{21}-C(=O)-$; $R^{21}-S(=O)_p-$; $R^7-S(=O)_p-$; $R^7-S(=O)_p-NH-$; $R^{21}-S(=O)_p-NH-$; $R^7-C(=O)-$; $-NHC(=O)H$; $-C(=O)NHNH_2$; $R^7-C(=O)-NH-$; $R^{21}-C(=O)-NH-$; $-C(=NH)R^7$; $-C(=NH)R^{21}$;

$R^4$ is a monocyclic, bicyclic or tricyclic saturated heterocycle; a monocyclic, bicyclic or tricyclic partially saturated heterocycle or a monocyclic, bicyclic or tricyclic aromatic heterocycle, each of said heterocycles optionally being substituted where possible with one or more substituents each independently being selected from =S; =O; $R^{15}$; hydroxy; halo; nitro; cyano; $R^{15}-O-$; SH; $R^{15}-S-$; formyl; carboxyl; $R^{15}-C(=O)-$; $R^{15}-O-C(=O)-$; $R^{15}-C(=O)-O-$; $R^{15}-O-C(=O)-O-$; $-SO_3H$; $R^{15}-S(=O)-$; $R^{15}-S(=O)_2-$; $R^5R^6N$; $R^5R^6NC_{1-6}$alkyl; $R^5R^6NC_{3-7}$cycloalkyl; $R^5R^6NC_{1-6}$alkyloxy; $R^5R^6N-C(=O)-$; $R^5R^6N-C(=S)-$; $R^5R^6N-C(=O)-NH-$; $R^5R^6N-C(=S)-NH-$; $R^5R^6N-S(=O)_n-$; $R^5R^6N-S(=O)_n-NH-$; $R^{15}-C(=S)-$; $R^{15}-C(=O)-NH-$; $R^{15}-O-C(=O)-NH-$; $R^{15}-S(=O)_n-NH-$; $R^{15}-O-S(=O)_n-NH-$; $R^{15}-C(=S)-NH-$; $R^{15}-O-C(=S)-NH-$; $R^{17}R^{18}N-Y_{1a}-$; $R^{17}R^{18}N-Y_2-NR^{16}-Y_1-$; $R^{15}-Y_2-NR^{19}-Y_1-$; $H-Y_2-NR^{19}-Y_1-$;

$R^5$ and $R^6$ each independently are hydrogen, $R^8$, $-Y_1-NR^9-Y_2-NR^{10}R^{11}$, $-Y_1-NR^9-Y-$, $-R^8$, $-Y_1-NR^9R^{10}$;

$R^7$ is $C_{1-6}$alkyl, $C_{1-6}$alkyloxy, amino, mono- or di($C_{1-6}$alkyl)amino or polyhalo$C_{1-6}$alkyl;

$R^8$ is $C_{1-6}$alkyl; $C_{2-6}$alkenyl; $C_{2-6}$alkynyl; a monocyclic, bicyclic or tricyclic saturated carbocycle; a monocyclic, bicyclic or tricyclic partially saturated carbocycle; a monocyclic, bicyclic or tricyclic aromatic carbocycle; a monocyclic, bicyclic or tricyclic saturated heterocycle; a monocyclic, bicyclic or tricyclic partially saturated heterocycle; a monocyclic, bicyclic or tricyclic aromatic heterocycle; $C_{1-6}$alkyl substituted with a monocyclic, bicyclic or tricyclic saturated carbocycle or with a monocyclic, bicyclic or tricyclic partially saturated carbocycle or with a monocyclic, bicyclic or tricyclic aromatic carbocycle or with a monocyclic, bicyclic or tricyclic saturated heterocycle or with a monocyclic, bicyclic or tricyclic partially saturated heterocycle or with a monocyclic, bicyclic or tricyclic aromatic heterocycle; each of said groups representing $R^8$ may optionally be substituted with one or more substituents selected from $R^{12}$, $R^{13}$ and $R^{14}$;

$R^9$, $R^{10}$ and $R^{11}$ each independently are hydrogen or $R^8$;

$R^{12}$, $R^{13}$ and $R^{14}$ each independently are hydrogen; $R^{15}$; hydroxy; halo; nitro; cyano; $R^{15}-O-$; SH; $R^{15}-S-$; formyl; carboxyl; $R^{15}-C(=O)-$; $R^{15}-O-C(=O)-$; $R^{15}-C(=O)-O-$; $R^{15}-O-C(=O)-O-$; $-SO_3H$; $R^{15}-S(=O)-$; $R^5-S(=O)_2-$; $R^5R^{16}N-S(=O)-$; $R^{15}R^{16}N-S(=O)_2-$; $R^{17}R^{18}N-Y_1-$; $R^{17}R^{18}N-Y_2-NR^{16}-Y_1-$; $R^{15}-Y_2-NR^{19}-Y_1-$; $H-Y_2-NR^{19}-Y_1-$; oxo;

$R^{15}$ is $C_{1-6}$alkyl, $C_{2-6}$alkenyl, $C_{2-6}$alkynyl, a monocyclic, bicyclic or tricyclic saturated carbocycle; a monocyclic, bicyclic or tricyclic partially saturated carbocycle; a monocyclic, bicyclic or tricyclic aromatic carbocycle; a monocyclic, bicyclic or tricyclic saturated heterocycle; a monocyclic, bicyclic or tricyclic partially saturated heterocycle;

a monocyclic, bicyclic or tricyclic aromatic heterocycle; $C_{1-6}$alkyl substituted with a monocyclic, bicyclic or tricyclic saturated carbocycle or with a monocyclic, bicyclic or tricyclic partially saturated carbocycle or with a monocyclic, bicyclic or tricyclic aromatic carbocycle or with a monocyclic, bicyclic or tricyclic saturated heterocycle or with a monocyclic, bicyclic or tricyclic partially saturated heterocycle or with a monocyclic, bicyclic or tricyclic aromatic heterocycle; each of said substituents representing $R^{15}$ may optionally be substituted with one or more substituents selected from $R^{12}$, $R^{13}$ and $R^{14}$;

$R^{16}$, $R^{17}$, $R^{18}$ and $R^{19}$ each independently are hydrogen or $R^{15}$;

$R^{20}$ is a monocyclic, bicyclic or tricyclic saturated carbocycle; a monocyclic, bicyclic or tricyclic partially saturated carbocycle; a monocyclic, bicyclic or tricyclic aromatic carbocycle; a monocyclic, bicyclic or tricyclic saturated heterocycle; a monocyclic, bicyclic or tricyclic partially saturated heterocycle; a monocyclic, bicyclic or tricyclic aromatic heterocycle;

$R^{21}$ is a monocyclic, bicyclic or tricyclic saturated carbocycle; a monocyclic, bicyclic or tricyclic partially saturated carbocycle; a monocyclic, bicyclic or tricyclic aromatic carbocycle; a monocyclic, bicyclic or tricyclic saturated heterocycle; a monocyclic, bicyclic or tricyclic partially saturated heterocycle; a monocyclic, bicyclic or tricyclic aromatic heterocycle, each of said carbocycles or heterocycles representing $R^{21}$ may optionally be substituted with one or more substituents selected from $R^{12}$, $R^{13}$ and $R^{14}$;

$Y_{1a}$ is $-Y_3-S(=O)-Y_4-$; $-Y_3-S(=O)_2-Y_4-$, $-Y_3-C(=O)-Y_4-$, $-Y_3-C(=S)-Y_4-$, $-Y_3-O-Y_4-$, $-Y_3-S-Y_4-$, $-Y_3-O-C(=O)-Y_4-$ or $-Y_3-C(=O)-O-Y_4-$;

$Y_1$ or $Y_2$ each independently are a direct bond, $-Y_3-S(=O)-Y_4-$; $-Y_3-S(=O)_2-Y_4-$, $-Y_3-C(=O)-Y_4-$, $-Y_3-C(=S)-Y_4-$, $-Y_3-O-Y_4-$, $-Y_3-S-Y_4-$, $-Y_3-O-C(=O)-Y_4-$ or $-Y_3-C(=O)-O-Y_4-$;

$Y_3$ or $Y_4$ each independently are a direct bond, $C_{1-6}$alkanediyl, $C_{2-6}$alkenediyl or $C_{2-6}$alkynediyl;

n is 1 or 2;
m is 1 or 2;
p is 1 or 2;
r is 1 to 5;
s is 1 to 3;

aryl is phenyl or phenyl substituted with one, two, three, four or five substituents each independently selected from halo, $C_{1-6}$alkyl, $C_{3-7}$cycloalkyl, $C_{1-6}$alkyloxy, cyano, nitro, polyhalo$C_{1-6}$alkyl and polyhalo$C_{1-6}$alkyloxy;

provided that $-X-R^2$ and/or $R^3$ is other than hydrogen; and provided that when

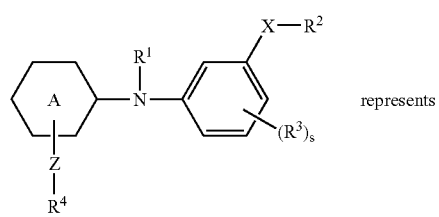

represents

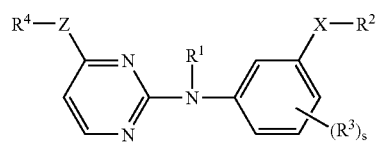

then

-Z is other than a direct bond or NH when $R^1$ is hydrogen or methyl, s is 2, $R^3$ is methoxy, and $-X-R^2$ is methoxy;

-Z—$R^4$ is other than 3-pyridyl, 4-pyridyl or 4-pyridyl N-oxide when $R^1$ is hydrogen or methyl, s is 1, $R^3$ is 3-chloro or 4-methoxy, and $-X-R^2$ is hydrogen;

-Z—$R^4$ is other than

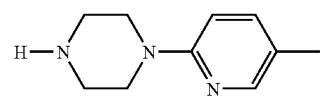

when $R^1$ is hydrogen;

—$R^3$ and —$X$—$R^2$ are other than hydrogen when $R^1$ is hydrogen and -Z—$R^4$ is 3-pyridyl or substituted 4-pyridyl;

and provided that when

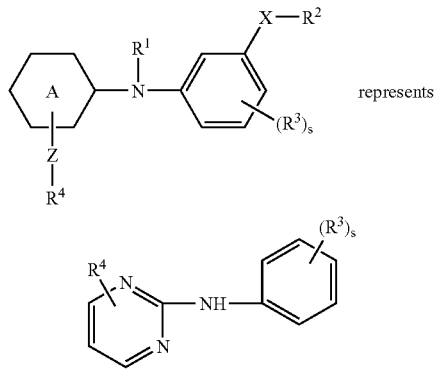

represents then

—$R^4$ is other than pyridyl optionally substituted with methyl, pyridyl N-oxide, 1-methyl-pyridinium, thienyl optionally substituted with one or two methyl groups, furanyl optionally substituted with one or two methyl groups, benzofuranyl, quinolinyl, indolyl, pyrrolyl optionally substituted with methyl, pyrimidinyl, phenothiazinyl; and provided that the following compounds

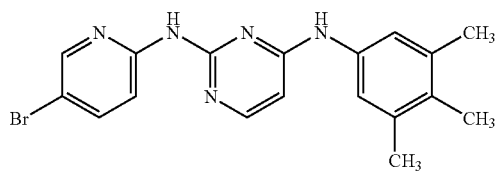

-continued

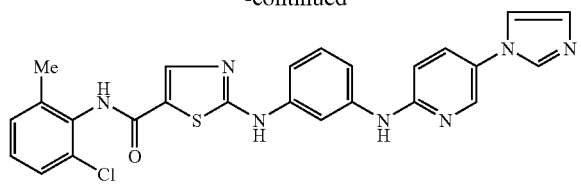

are not included.

Further interesting compounds are those compounds of formula (I) or (I') as defined hereinabove, their N-oxides, pharmaceutically acceptable addition salts, quaternary amines and stereochemically isomeric forms thereof, wherein ring A is pyridyl, pyrimidinyl or pyridazinyl;

$R^1$ is hydrogen;

X is a direct bond, —O— or —O—$C_{1-6}$alkyl-;

Z is a direct bond, —$NR^1$—, —$NR^1$—$C_{1-6}$alkyl- or —C(=O)—;

$R^2$ is hydrogen or $R^{20}$;

$R^3$ is hydrogen, halo, $C_{1-6}$alkyl, polyhalo$C_{1-6}$alkyl or cyano;

$R^4$ is a monocyclic, bicyclic or tricyclic saturated heterocycle; a monocyclic, bicyclic or tricyclic partially saturated heterocycle or a monocyclic, bicyclic or tricyclic aromatic heterocycle, each of said heterocycles optionally being substituted where possible with one or more substituents each independently being selected from $R^{15}$, $R^{15}$—O—, $R^{15}$—C(=O)— or halo;

$R^{15}$ is $C_{1-6}$alkyl; a monocyclic, bicyclic or tricyclic saturated heterocycle; $C_{1-6}$alkyl substituted with a monocyclic, bicyclic or tricyclic aromatic carbocycle;

$R^{20}$ is a monocyclic, bicyclic or tricyclic aromatic carbocycle;

s is 1 to 3;

provided that —X—$R^2$ and/or $R^3$ is other than hydrogen; and provided that when

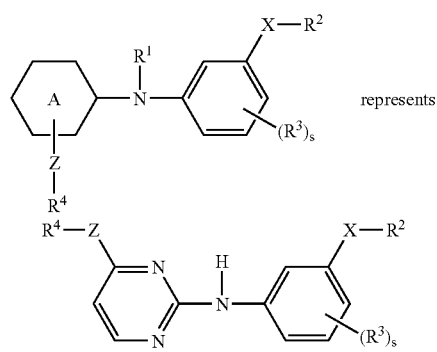

then
-Z—$R^4$ is other than 3-pyridyl, 4-pyridyl or 4-pyridyl N-oxide when s is 1, $R^3$ is 3-chloro, and —X—$R^2$ is hydrogen;
-Z—$R^4$ is other than

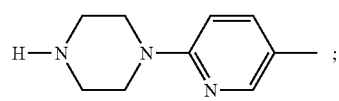

—$R^3$ and —X—$R^2$ are other than hydrogen when -Z—$R^4$ is 3-pyridyl or substituted 4-pyridyl;
and provided that when

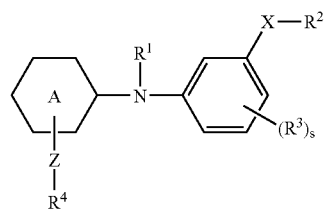 represents

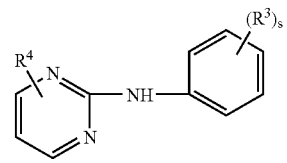

then
—$R^4$ is other than pyridyl optionally substituted with methyl, pyridyl N-oxide, 1-methyl-pyridinium, thienyl optionally substituted with one or two methyl groups, furanyl optionally substituted with one or two methyl groups, benzofuranyl, quinolinyl, indolyl, pyrrolyl optionally substituted with methyl, pyrimidinyl, phenothiazinyl;

Also interesting compounds are those compounds of formula (I) or (I') as defined hereinabove provided that the compound is other than a)

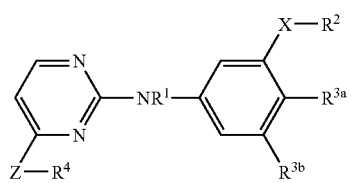

wherein
X is —O—; $R^2$ is $C_{1-10}$alkyl, $C_{2-10}$alkenyl or $C_{2-10}$alkynyl, said groups representing $R^2$ may optionally be substituted; $R^{3a}$ is $C_{1-6}$alkyloxy; $R^{3b}$ is hydrogen, halo, optionally substituted $C_{1-10}$alkyl, optionally substituted $C_{2-10}$alkenyl, optionally substituted $C_{2-10}$alkynyl, hydroxy, amino, mono- or di($C_{1-6}$alkyl)amino, $C_{1-6}$alkyl-C(=O)—NH—, $C_{1-6}$alkyloxy, polyhalo$C_{1-6}$alkyloxy, $C_{1-6}$alkylthio, polyhalo$C_{1-6}$alkylthio, aryloxy; $R^1$ is hydrogen or $C_{1-6}$alkyl and Z-$R^4$ is as defined hereinabove;

b) 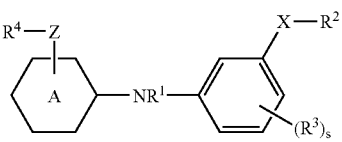

wherein
Z is $C_{1-6}$alkanediyl, $C_{2-6}$alkenediyl, —C(=O)— or —C(=S)—; ring A is as defined hereinabove; $R^4$ is monocyclic, bicyclic or tricyclic saturated heterocycle; a monocyclic, bicyclic or tricyclic partially saturated heterocycle or a monocyclic, bicyclic or tricyclic aromatic heterocycle, said groups representing $R^4$ may optionally be substituted; $R^1$ is hydrogen; aryl; $C_{1-6}$alkylcarbonyl; $C_{1-6}$alkyl; $C_{1-6}$alkyloxycarbonyl; $C_{1-6}$alkyl substituted with formyl, $C_{1-6}$alkylcarbonyl, $C_{1-6}$alkyloxycarbonyl, $C_{1-6}$alkylcarbonyloxy; $C_{1-6}$alkyloxy$C_{1-6}$alkylcarbonyl optionally substituted with $C_{1-6}$alkyloxycarbonyl; X is a direct bond or $C_{1-6}$alkyl; $R^2$, $R^3$ and s are as defined hereinabove;

c) 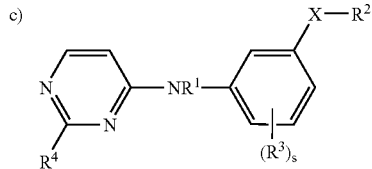

wherein

X is a direct bond, —O—, —S—, —C(=O)—NH—, —C(=O)—O—; $R^2$ is hydrogen, $CF_3$, $C_{1-4}$alkyl; $R^3$ is hydrogen, hydroxy, halo, $CF_3$, $C_{1-4}$alkyl, $C_{1-4}$alkyloxy, $C_{1-4}$alkylthio, cyano, amino, aminocarbonyl, carboxyl, $C_{1-4}$alkylcarbonyl; $R^1$ is hydrogen or $C_{1-4}$alkyl; $R^4$, $R^3$ and s are as defined hereinabove;

d) 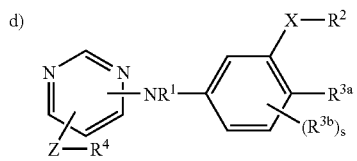

wherein $R^4$-Z represents indolyl-$C_{1-10}$alkyl or Z is a direct bond, —$C_{1-6}$alkyl-, —$NR^1$—, —NH—NH—, —N=N—, —O—, —(C=O)—, —CHOH—, —S—, —S(=O)—, —S(=O)$_2$—, —O—$C_{1-4}$alkyl-, —NR; —$C_{1-4}$alkyl-, —S—$C_{1-4}$alkyl- and $R^4$ is pyridyl, pyrimidinyl, pyridazinyl, pyrazinyl, said groups representing $R^4$ may optionally be substituted; $R^1$ is hydrogen, aryl, $C_{1-6}$alkylcarbonyl, $C_{1-6}$alkyl, $C_{1-6}$alkyloxycarbonyl; X—$R^2$ is hydrogen, hydroxy, $C_{1-6}$alkyl, $C_{1-6}$alkyloxy, trihalomethyl, trihalomethyloxy, cyano$C_{1-6}$alkyl; $R^{3a}$ is halo, $C_{1-6}$alkyl, cyano, nitro, trihalomethyl, trihalomethyloxy or $C_{1-6}$alkyl substituted with cyano or aminocarbonyl; $R^{3b}$ is hydroxy, halo, $C_{1-6}$alkyl, $C_{1-6}$alkyloxy, cyano, aminocarbonyl, nitro, amino, trihalomethyl, trihalomethyloxy; s is 0, 1 or 2;

e) 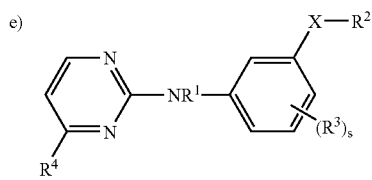

wherein $R^4$ is 2-pyridyl, 3-pyridyl, 4-pyridyl, 2-methyl-3-pyridyl, 4-methyl-3-pyridyl, 2-furyl, 5-methyl-2-furyl, 2,5-dimethyl-3-furyl, 2-thienyl, 3-thienyl, 5-methyl-2-thienyl, 2-phenothiazinyl, 4-pyrazinyl, 2-benzofuryl, N-oxido-2-pyridyl, N-oxido-3-pyridyl, N-oxido-4-pyridyl, 1H-indol-2-yl, 1H-indol-3-yl, 1-methyl-1H-pyrrol-2-yl, 4-quinolinyl, 1-methyl-pyridinium-4-yliodide; $R^1$ is hydrogen or $C_{1-3}$alkyl; X—$R^2$, $R^3$ and s are as defined hereinabove;

f) 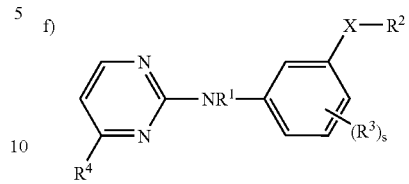

wherein $R^4$ is N-methylpiperazinyl, piperidinyl, imidazolyl, triazolyl, benzimidazolyl, 4-phenyl-piperazin-1-yl wherein phenyl may optionally be substituted with $C_{1-3}$alkyl or $C_{1-3}$alkyloxy or halo or trifluoromethyl, 1H-imidazol-1-yl$C_{1-3}$alkyl, 1H-imidazol-1-yl$C_{1-3}$alkyloxy, 1H-imidazol-1-yl$C_{1-3}$alkylthio, morpholinyl$C_{1-3}$alkyl, morpholinyl$C_{1-3}$alkyloxy, morpholinyl$C_{1-3}$alkylthio; X is a direct bond; $R^2$ is hydrogen, $C_{1-3}$alkyl, 2-pyridyl, 3-pyridyl, 4-pyridyl, 2-methyl-3-pyridyl, 4-methyl-3-pyridyl, 2-furyl, 5-methyl-2-furyl, 2,5-dimethyl-3-furyl, 2-thienyl, 3-thienyl, 5-methyl-2-thienyl, 2-phenothiazinyl, 4-pyrazinyl, 2-benzofuryl, N-oxido-2-pyridyl, N-oxido-3-pyridyl, N-oxido-4-pyridyl, 1H-indol-2-yl, 1H-indol-3-yl, 1-methyl-1H-pyrrol-2-yl, 4-quinolinyl, 1-methyl-pyridinium-4-yliodide; $R^3$ is hydrogen, $C_{1-3}$alkyl, 2-pyridyl, 3-pyridyl, 4-pyridyl, 2-methyl-3-pyridyl, 4-methyl-3-pyridyl, 2-furyl, 5-methyl-2-furyl, 2,5-dimethyl-3-furyl, 2-thienyl, 3-thienyl, 5-methyl-2-thienyl, 2-phenothiazinyl, 4-pyrazinyl, 2-benzofuryl, N-oxido-2-pyridyl, N-oxido-3-pyridyl, N-oxido-4-pyridyl, 1H-indol-2-yl, 1H-indol-3-yl, 1-methyl-1H-pyrrol-2-yl, 4-quinolinyl, 1-methyl-pyridinium-4-yliodide; s is as defined hereinbove;

g) 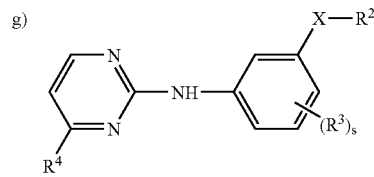

wherein $R^4$ is pyridyl substituted with an optionally substituted monocyclic, bicyclic or tricyclic saturated heterocycle consisting of from 3 to 7 atoms, and X, $R^2$, $R^3$ and s are as defined hereinabove;

h) 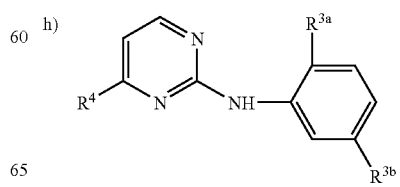

wherein R⁴ is 4-pyridyl substituted in position 3; $R^{3a}$ is hydrogen, halo, $C_{1-6}$alkyloxy or $C_{1-6}$alkyl; $R^{3b}$ is as defined above for $R^3$;

i)
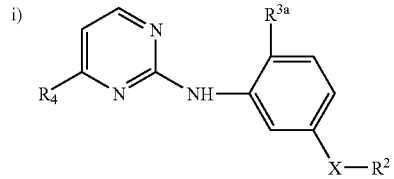

wherein R⁴ is 4-pyridyl substituted in position 3; $R^{3a}$ is hydrogen, halo, $C_{1-6}$alkyloxy or $C_{1-6}$alkyl; X—R² is as defined above;

j)
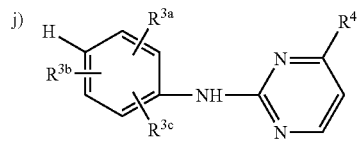

wherein $R^{3a}$ is halo, cyano, $C_{1-4}$alkyloxy, polyhalo$C_{1-4}$alkyloxy, $C_{1-4}$alkylthio, $C_{1-4}$alkyl-S(=O)—, $C_{1-4}$alkyl-S(=O)$_2$—, $C_{1-4}$alkyl, polyhalo$C_{1-4}$alkyl, $C_{1-4}$alkyloxycarbonyl, mono-or di($C_{1-4}$alkyl)aminocarbonyl, aminocarbonyl, polyhalo$C_{1-4}$alkylthio; $R^{3b}$ is hydrogen, halo, cyano, nitro, $C_{1-4}$alkyl, $C_{1-4}$alkyloxy, polyhalo$C_{1-4}$alkyl, $C_{1-4}$alkyloxycarbonyl, $C_{1-4}$alkylcarbonyl; $R^{3c}$ is hydrogen, halo or $C_{1-4}$alkyl; R⁴ is 2-furanyl, 2-thienyl or 3-thienyl;

k)
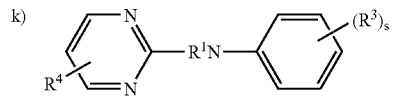

wherein R⁴ is pyridyl, pyrimidinyl, thiazolyl, pyrazinyl, pyridazinyl, or imidazolyl, each of said rings optionally substituted with one or more substituents selected from halo, cyano, aminocarbonyl, —C(=O)—O—R⁴', —C(=O)—R⁴', —S(=O)$_2$—NR⁴'R⁴'', NR⁴'R⁴'', —O—R⁴' or $C_{1-6}$alkyl optionally substituted with fluoro wherein R⁴' and R⁴'' each independently represent hydrogen or $C_{1-6}$alkyl optionally substituted with mono- or di($C_{1-6}$alkyl)amino; R¹, R³ and s are as defined hereinabove;

l)
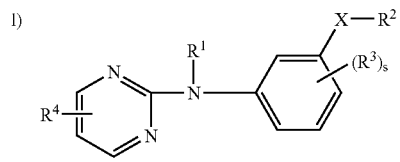

wherein R⁴ is 2-pyridyl, 3-pyridyl, 4-pyridyl, 2-methyl-3-pyridyl, 6-methyl-3-pyridyl, 2-furanyl, 5-methyl-2-furanyl, 2,5-dimethyl-3-furanyl, 2-thienyl, 3-thienyl, 5-methyl-2-thienyl, 2-pheno-thiazinyl, 2-pyrazinyl, 2-benzofuranyl, 2-pyridyl-N-oxide, 3-pyridyl-N-oxide, 4-pyridyl-N-oxide, 1H-indol-2-yl, 1H-indol-3-yl, 1-methyl-1H-pyrrol-2-yl, 4-quinolinyl, 4-pyridyl methyl iodide, dimethylaminophenyl; R¹ is hydrogen or $C_{1-3}$alkyl; s is 1 to 3; X, R² and R³ are as defined hereinabove.

m)
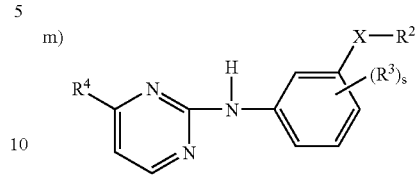

wherein R⁴ is 4-pyrazinyl, 1-methyl-1H-pyrrolyl, pyridyl optionally substituted with $C_{1-6}$alkyl, pyridyl N-oxide optionally substituted with $C_{1-6}$alkyl; X is —O—, —NR¹—C(=O)—O—, —NR¹—C(=O)—, —NR¹—C(=S)—, —NR¹—C(=O)—NR¹—, —NR¹—C(=S)—NR¹— or a direct bond; R² is fluoro-substituted $C_{1-10}$alkyl, optionally substituted phenyl or naphthyl, optionally substituted phenyl$C_{1-6}$alkyl, a monocyclic, bicyclic or tricyclic saturated carbocycle consisting of from 3 to 10 carbon atoms, a monocyclic, bicyclic or tricyclic partially saturated carbocycle consisting of from 3 to 10 carbon, $C_{1-6}$alkyl substituted with a monocyclic, bicyclic or tricyclic saturated carbocycle consisting of from 3 to 10 carbon atoms or a monocyclic, bicyclic or tricyclic partially saturated carbocycle consisting of from 3 to 10 carbon, a 5 or 6-membered heterocycle containing from 1 to 3 heteroatoms wherein the heteroatom is selected from O, N or S to which 5 or 6-membered heterocycle one or two benzene radicals may be fused, $C_{1-6}$alkyl substituted by a 5 or 6-membered heterocycle containing from 1 to 3 heteroatoms wherein the heteroatom is selected from O, N or S to which 5 or 6-membered heterocycle one or two benzene radicals may be fused; R³ is nitro, R⁷—C(=O)—NH—; $R^{21}$—C(=O)—NH—; s is as defined hereinabove.

Further preferred compounds are those compounds of formula (I) or (I') wherein one of the following restrictions apply:
a) X is a direct bond and R² is hydrogen;
b) R² and R³ are other than hydrogen;
c) R³ is hydrogen;
d) Z is a direct bond.

Also preferred compounds are those compounds of formula (I) or (I') wherein ring A is pyridyl, pyrimidinyl or pyridazinyl, in particular pyrimidinyl or pyridazinyl.

Other preferred compounds are those compounds of formula (I) or (I') wherein ring A is pyridyl, pyrimidinyl or pyridazinyl; in particular pyrimidinyl or pyridazinyl;
R¹ is hydrogen; aryl; formyl; $C_{1-6}$alkylcarbonyl; $C_{1-6}$alkyl; $C_{1-6}$alkyloxycarbonyl; $C_{1-6}$alkyl substituted with formyl, $C_{1-6}$alkylcarbonyl, $C_{1-6}$alkyloxycarbonyl, $C_{1-6}$alkylcarbonyloxy; $C_{1-6}$alkyloxy$C_{1-6}$alkylcarbonyl optionally substituted with $C_{1-6}$alkyloxycarbonyl;

X is —NR¹—; —NH—NH—; —N=N—; —O—; —C(=O)—; —C(=S)—; —O—C(=O)—; —C(=O)—O—; —O—C(=O)—$C_{1-6}$alkyl-; —C(=O)—O—$C_{1-6}$alkyl-; —O—$C_{1-6}$alkyl-C(=O)—; —C(=O)—$C_{1-6}$alkyl-O—; —O—C(=O)—NR¹—; —NR¹—C(=O)—O—; —O—C(=O)—C(=O)—; —C(=O)—NR¹—, —NR¹—C(=O)—; —C(=S)—NR¹—, —NR¹—C(=S)—; —NR¹—C(=O)—NR¹—; —NR¹—C(=S)—NR¹—; —NR¹—S(=O)—NR¹—; —NR¹—S(=O)$_2$—NR¹—; —$C_{1-6}$alkyl-C(=O)—NR¹—; —O—$C_{1-6}$alkyl-C(=O)—NR¹—; —$C_{1-6}$alkyl-O—C(=O)—NR¹—; —$C_{1-6}$alkyl-; —O—$C_{1-6}$alkyl-; —$C_{1-6}$alkyl-O—; —NR¹—$C_{1-6}$alkyl—; —$C_{1-6}$alkyl- —NR$^1$—; —NR$^1$—C$_{1-6}$alkyl-NR$^1$—; —NR$^1$—C$_{1-6}$alkyl-C$_{3-7}$cycloalkyl-; —C$_{2-6}$alkenyl-; —C$_{2-6}$alkynyl-; —O—C$_{2-6}$alkenyl-; —C$_{2-6}$alkenyl-O—; —NR$^1$—C$_{2-6}$alkenyl-; —C$_{2-6}$alkenyl-NR$^1$—; —NR$^1$—C$_{2-6}$alkenyl-NR$^1$—; —NR$^1$—C$_{2-6}$alkenyl-C$_{3-7}$cycloalkyl-; —O—C$_{2-6}$alkynyl-; —C$_{2-6}$alkynyl-O—; —NR$^1$—C$_{2-6}$alkynyl-; —C$_{2-6}$alkynyl-NR$^1$—; —NR$^1$—C$_{2-6}$alkynyl-NR$^1$—; —NR$^1$—C$_{2-6}$alkynyl-C$_{3-7}$cycloalkyl-; —O—C$_{1-6}$ alkyl-O—; —O—C$_{2-6}$alkenyl-O—; —O—C$_{2-6}$ alkynyl-O—; —CHOH—; —S—; —S(=O)—; —S(=O)$_2$—; —S(=O)—NR$^1$—; —S(=O)$_2$—NR$^1$—; —NR$^1$—S(=O)—; —NR$^1$—S(=O)$_2$—; —S—C$_{1-6}$ alkyl-; —C$_{1-6}$ alkyl-S—; —S—C$_{2-6}$alkenyl-; —C$_{2-6}$alkenyl-S—; —S—C$_{2-6}$alkynyl-; —C$_{2-6}$alkynyl-S—; —O—C$_{1-6}$alkyl-S(=O)$_2$— or a direct bond;

Z is a direct bond, C$_{1-6}$alkanediyl, C$_{2-6}$alkenediyl, C$_{2-6}$alkynediyl; —O—; —O—C$_{1-6}$alkyl-; —C(=O)—; —C(=O)—O—; —O—C(=O)—; —C(=S)—; —S(=O)—; —S(=O)$_2$—; —NR$^1$—; —NR$^1$—C$_{1-6}$alkyl-; —NR$^1$—C(=O)—; —O—C(=O)—NR$^1$—; —NR$^1$—C(=O)—O—; —NR$^1$—C(=S)—; —S(=O)—NR$^1$—; —S(=O)$_2$—NR$^1$—; —NR$^1$—S(=O)—; —NR$^1$—S(=O)$_2$—; —NR$^1$—(C=O)—NR$^1$—; —NR$^1$—C(=S)—NR$^1$—; —NR$^1$—S(=O)—NR$^1$—; —NR$^1$—S(=O)$_2$—NR$^1$—;

R$^2$ is hydrogen, C$_{1-10}$alkyl, C$_{2-10}$alkenyl, C$_{2-10}$alkynyl, R$^{20}$, each of said groups representing R$^2$ may optionally be substituted where possible with one or more substituents each independently being selected from =S; =O; R$^{15}$; hydroxy; halo; nitro; cyano; R$^{15}$—O—; SH; R$^{15}$—S—; formyl; carboxyl; R$^{15}$—C(=O)—; R$^{15}$—O—C(=O)—; R$^{15}$—C(=O)—O—; R$^{15}$—O—C(=O)—O—; —SO$_3$H; R$^{15}$—S(=O)—; R$^{15}$—S(=O)$_2$—; R$^5$R$^6$N; R$^5$R$^6$N—C$_{1-6}$alkyl; R$^5$R$^6$N—C$_{3-7}$cycloalkyl; R$^5$R$^6$N—C$_{1-6}$alkyloxy; R$^{5a}$R$^{6a}$N—C(=O)—; R$^5$R$^6$N—C(=S); R$^5$R$^6$N—C(=O)—NH—; R$^5$R$^6$N—C(=S)—NH—; R$^5$R$^6$N—S(=O)$_n$—; R$^5$R$^6$N—S(=O)$_1$—NH—; R$^{15}$—C(=S)—; R$^{15}$—C(=O)—NH—; R$^{15}$—O—C(=O)—NH—; R$^{15}$—S(=O), —NH—; R$^{15}$—O—S(=O), —NH—; R$^{15}$—C(=S)—NH—; R$^{15}$—O—C(=S)—NH—; R$^{17}$R$^{18}$N—Y$_{1a}$—; R$^{17}$R$^{18}$N—Y$_2$—NR$^{16}$—Y$_1$—; R$^{15}$—Y$_2$—NR$^9$—Y$_1$—; H—Y$_2$—NR$^{19}$—Y$_1$—;

R$^3$ is hydrogen; hydroxy; halo; C$_{1-6}$alkyl; C$_{1-6}$alkyl substituted with cyano, hydroxy or —C(=O)R$^7$; C$_{2-6}$alkenyl; C$_{2-6}$alkenyl substituted with one or more halogen atoms or cyano; C$_{2-6}$alkynyl; C$_{2-6}$alkynyl substituted with one or more halogen atoms or cyano; C$_{1-6}$alkylthio; C$_{1-6}$alkyloxycarbonyl; C$_{1-6}$alkylcarbonyloxy; carboxyl; cyano; nitro; amino; mono- or di(C$_{1-6}$alkyl)amino; polyhaloC$_{1-6}$alkyl; polyhaloC$_{1-6}$alkylthio; R$^{21}$; R$^{21}$—C$_{1-6}$alkyl; R$^{21}$—O—; R$^{21}$—S—; R$^{21}$—C(=O)—; R$^{21}$—S(=O)$_p$—; R$^7$—S(=O)$_p$—; R$^7$—S(=O)$_p$—NH—; R$^{21}$—S(=O)$_p$—NH—; R$^7$—C(=O)—; —NHC(=O)H; —C(=O)NHNH$_2$; R$^7$—C(=O)—NH—; R$^{21}$—C(=O)—NH—; —C(=NH)R$^7$; —C(=NH)R$^2$;

R$^4$ is tetrahydrofuranyl, dihydrofuranyl, pyrrolinyl, pyrrolidinyl, imidazolyl, imidazolinyl, imidazolidinyl, oxazolyl, pyrimidinyl, pyridyl, piperidinyl, piperazinyl, pyridazinyl, triazinyl, morpholinyl, dioxolanyl or dioxanyl, each of said heterocycles optionally being substituted where possible with one or more substituents each independently being selected from =S; =O; R$^{15}$; hydroxy; halo; nitro; cyano; R$^{15}$—O—; SH; R$^{15}$—S—; formyl; carboxyl; R$^{15}$—C(=O)—; R$^{15}$—O—C(=O)—; R$^{15}$—C(=O)—O—; R$^{15}$—O—C(=O)—O—; —SO$_3$H; R$^{15}$—S(=O)—; R$^{15}$—S(=O)$_2$—; R$^5$R$^6$N; R$^5$R$^6$NC$_{1-6}$alkyl; R$^5$R$^6$NC$_{3-7}$cycloalkyl; R$^5$R$^6$NC$_{1-6}$alkyloxy; R$^5$R$^6$N—C(=O)—; R$^5$R$^6$N—C(=S)—; R$^5$R$^6$N—C(=O)—NH—; R$^5$R$^6$N—C(=S)—NH—; R$^5$R$^6$N—S(=O)$_n$—; R$^5$R$^6$N—S(=O)$_n$—NH—; R$^{15}$—C(=S)—; R$^{15}$—C(=O)—NH—; R$^{15}$—O—C(=O)—NH—; R$^{15}$—S(=O)$_n$—, —NH—; R$^{15}$—O—S(=O), —NH—; R$^{15}$—C(=S)—NH—; R$^{15}$—O—C(=S)—NH—; R$^{17}$R$^{18}$N—Y$_{1a}$—; R$^{17}$R$^{18}$N—Y$_2$—NR$^6$—Y$_1$—; R$^{15}$—Y$_2$—NR$^{19}$—Y$_1$—; H—Y$_2$—NR$^{19}$—Y$_1$—;

R$^5$ and R$^6$ each independently are hydrogen, R$^8$, —Y$_1$—NR$^9$—Y$_2$—NR$^{10}$R$^{11}$, —Y$_1$—NR$^9$—Y$_1$—R$^8$, —Y, —NR$^9$R$^{10}$, or R$^{5a}$ and R$^{6a}$ each independently are hydrogen, C$_{1-6}$alkyl; C$_{2-6}$alkenyl or C$_{2-6}$alkynyl, each of said groups representing R$^{5a}$ and R$^{6a}$ may optionally be substituted with one or more substituents selected from R$^{12}$, R$^{13}$ and R$^{14}$;

R$^5$ and R$^6$ may together with the nitrogen to which they are attached form a saturated or partially saturated monocyclic 3 to 8 membered heterocycle or an aromatic 4 to 8 membered monocyclic heterocycle, each of said heterocycles may optionally be substituted with one or more substituents selected from R$^{12}$, R$^{13}$ and R$^{14}$, or each of said heterocycles may optionally be fused with a benzene ring, said benzene ring being optionally substituted with one or more substituents selected from R$^{12}$, R$^{13}$ and R$^{14}$;

R$^7$ is C$_{1-6}$alkyl, C$_{1-6}$alkyloxy, amino, mono- or di(C$_{1-6}$alkyl)amino or polyhaloC$_{1-6}$alkyl;

R$^8$ is C$_{1-6}$alkyl; C$_{2-6}$alkenyl; C$_{2-6}$alkynyl; a monocyclic, bicyclic or tricyclic saturated carbocycle; a monocyclic, bicyclic or tricyclic partially saturated carbocycle; a monocyclic, bicyclic or tricyclic aromatic carbocycle; a monocyclic, bicyclic or tricyclic saturated heterocycle; a monocyclic, bicyclic or tricyclic partially saturated heterocycle; a monocyclic, bicyclic or tricyclic aromatic heterocycle; C$_{1-6}$alkyl substituted with a monocyclic, bicyclic or tricyclic saturated carbocycle or with a monocyclic, bicyclic or tricyclic partially saturated carbocycle or with a monocyclic, bicyclic or tricyclic aromatic carbocycle or with a monocyclic, bicyclic or tricyclic saturated heterocycle or with a monocyclic, bicyclic or tricyclic partially saturated heterocycle or with a monocyclic, bicyclic or tricyclic aromatic heterocycle; each of said groups representing R$^8$ may optionally be substituted with one or more substituents selected from R$^{12}$, R$^{13}$ and R$^{14}$;

R$^9$, R$^{10}$ and R$^{11}$ each independently are hydrogen or R$^8$, or any two of R$^9$, R$^{10}$ and R$^{11}$ may together be C$_{1-6}$alkanediyl or C$_{2-6}$alkenediyl thereby forming a saturated or partially saturated monocyclic 3 to 8 membered heterocycle or an aromatic 4 to 8 membered monocyclic heterocycle together with the nitrogen atoms to which they are attached, each of said heterocycles may optionally be substituted with one or more substituents selected from R$^{12}$, R$^{13}$ and R$^{14}$;

R$^{12}$, R$^{13}$ and R$^{14}$ each independently are hydrogen; R$^{15}$; hydroxy; halo; nitro; cyano; R$^{15}$—O—; SH; R$^{15}$—S—; formyl; carboxyl; R$^{15}$—C(=O)—; R$^{15}$—O—C(=O)—; R$^{15}$—C(=O)—O—; R$^{15}$—O—C(=O)—O—; —SO$_3$H; R$^{15}$—S(=O)—; R$^{15}$—S(=O)$_2$—; R$^5$R$^{16}$N—S(=O)—; R$^{15}$R$^{16}$N—S(=O)$_2$—; R$^{17}$R$^{18}$N—Y$_1$—; R$^{17}$R$^{18}$N—Y$_2$—NR$^{16}$—Y$_1$—; R$^{15}$—Y$_2$—NR$^{19}$—Y$_1$—; H—Y$_2$—NR$^{19}$—Y$_1$—; oxo, or any two of R$^{12}$, R$^{13}$ and R$^{14}$ may together be C$_{1-6}$alkanediyl or C$_{2-6}$alkenediyl thereby forming a saturated or partially saturated monocyclic 3 to 8 membered carbo— or heterocycle or an aromatic 4 to 8 membered monocyclic carbo— or heterocycle together with the atoms to which they are attached, or any two of $R^{12}$, $R^{13}$ and $R^{14}$ may together be —O(CH$_2$)$_r$—O— thereby forming a saturated, partially saturated or aromatic monocyclic 4 to 8 membered carbo— or heterocycle together with the atoms to which they are attached;

$R^{15}$ is $C_{1-6}$alkyl, $C_{2-6}$alkenyl, $C_{2-6}$alkynyl, a monocyclic, bicyclic or tricyclic saturated carbocycle; a monocyclic, bicyclic or tricyclic partially saturated carbocycle; a monocyclic, bicyclic or tricyclic aromatic carbocycle; a monocyclic, bicyclic or tricyclic saturated heterocycle; a monocyclic, bicyclic or tricyclic partially saturated heterocycle; a monocyclic, bicyclic or tricyclic aromatic heterocycle; $C_{1-6}$alkyl substituted with a monocyclic, bicyclic or tricyclic saturated carbocycle or with a monocyclic, bicyclic or tricyclic partially saturated carbocycle or with a monocyclic, bicyclic or tricyclic aromatic carbocycle or with a monocyclic, bicyclic or tricyclic saturated heterocycle or with a monocyclic, bicyclic or tricyclic partially saturated heterocycle or with a monocyclic, bicyclic or tricyclic aromatic heterocycle; each of said substituents representing $R^{15}$ may optionally be substituted with one or more substituents selected from $R^{12}$, $R^{13}$ and $R^{14}$; or each of said carbocycles or heterocycles may optionally be fused with a benzene ring, said benzene ring being optionally substituted with one or more substituents selected from $R^{12}$, $R^{13}$ and $R^{14}$;

$R^{16}$, $R^{17}$, $R^{18}$ and $R^{19}$ each independently are hydrogen or $R^{17}$, or $R^{17}$ and $R^{18}$, or $R^{15}$ and $R^{19}$ may together be $C_{1-6}$alkanediyl or $C_{2-6}$alkenediyl thereby forming a saturated or partially saturated monocyclic 3 to 8 membered heterocycle or an aromatic 4 to 8 membered monocyclic heterocycle, each of said heterocycles may optionally be substituted with one or more substituents selected from $R^2$, $R^{13}$ and $R^4$; or $R^{17}$ and $R^{18}$ together with $R^{16}$ may be $C_{1-6}$alkanediyl or $C_{2-6}$alkenediyl thereby forming a saturated or partially saturated monocyclic 3 to 8 membered heterocycle or an aromatic 4 to 8 membered monocyclic heterocycle together with the nitrogen atoms to which they are attached, each of said heterocycles may optionally be substituted with one or more substituents selected from $R^{12}$, $R^{13}$ and $R^{14}$;

$R^{20}$ is a monocyclic, bicyclic or tricyclic saturated carbocycle; a monocyclic, bicyclic or tricyclic partially saturated carbocycle; a monocyclic, bicyclic or tricyclic aromatic carbocycle; a monocyclic, bicyclic or tricyclic saturated heterocycle; a monocyclic, bicyclic or tricyclic partially saturated heterocycle; a monocyclic, bicyclic or tricyclic aromatic heterocycle;

$R^{21}$ is a monocyclic, bicyclic or tricyclic saturated carbocycle; a monocyclic, bicyclic or tricyclic partially saturated carbocycle; a monocyclic, bicyclic or tricyclic aromatic carbocycle; a monocyclic, bicyclic or tricyclic saturated heterocycle; a monocyclic, bicyclic or tricyclic partially saturated heterocycle; a monocyclic, bicyclic or tricyclic aromatic heterocycle, each of said carbocycles or heterocycles representing $R^{21}$ may optionally be substituted with one or more substituents selected from $R^{12}$, $R^{13}$ and $R^{14}$;

$Y_{1a}$ is —$Y_3$—S(=O)—$Y_4$—; —$Y_3$—S(=O)$_2$—$Y_4$—, —$Y_3$—C(=O)—$Y_4$—, —$Y_3$—C(=S)—$Y_4$—, —$Y_3$—O—$Y_4$—, —$Y_3$—S—$Y_4$—, —$Y_3$—O—C(=O)—$Y_4$— or —$Y_3$—C(=O)—O—$Y_4$—;

$Y_1$ or $Y_2$ each independently are a direct bond, —$Y_3$—S(=O)—$Y_4$—; —$Y_3$—S(=O)$_2$—$Y_4$—, —$Y_3$—C(=O)—$Y_4$—, —$Y_3$—C(=S)—$Y_4$—, —$Y_3$—O—$Y_4$—, —$Y_3$—S—$Y_4$—, —$Y_3$—O—C(=O)—$Y_4$— or —$Y_3$—C(=O)—O—$Y_4$—;

$Y_3$ or $Y_4$ each independently are a direct bond, $C_{1-6}$alkanediyl, $C_{2-6}$alkenediyl or $C_{2-6}$alkynediyl;

n is 1 or 2;

m is 1 or 2;

p is 1 or 2;

r is 1 to 5;

s is 1 to 3;

aryl is phenyl or phenyl substituted with one, two, three, four or five substituents each independently selected from halo, $C_{1-6}$alkyl, $C_{3-7}$cycloalkyl, $C_{1-6}$alkyloxy, cyano, nitro, polyhalo$C_{1-6}$alkyl and polyhalo$C_{1-6}$alkyloxy; provided that —X—$R^2$ and/or $R^3$ is other than hydrogen; and provided that $R^4$ is other than optionally substituted pyridyl when ring A represents pyrimidinyl.

Still other preferred compounds are those compounds of formula (I) or (I') wherein ring A is pyridyl, pyrimidinyl or pyridazinyl; in particular pyrimidinyl or pyridazinyl;

$R^1$ is hydrogen; aryl; formyl; $C_{1-6}$alkylcarbonyl; $C_{1-6}$alkyl; $C_{1-6}$alkyloxycarbonyl; $C_{1-6}$alkyl substituted with formyl, $C_{1-6}$alkylcarbonyl, $C_{1-6}$alkyloxycarbonyl, $C_{1-6}$alkylcarbonyloxy; $C_{1-6}$alkyloxy$C_{1-6}$alkylcarbonyl optionally substituted with $C_{1-6}$alkyloxycarbonyl;

X is —NR$^1$—; —O—; —C(=O)—; —O—C(=O)—; —C(=O)—O—; —O—C(=O)—$C_{1-6}$alkyl-; —C(=O)—O—$C_{1-6}$alkyl-; —O—$C_{1-6}$alkyl-C(=O)—; —C(=O)—$C_{1-6}$alkyl-O—; —O—C(=O)—NR$^1$—; —NR$^1$—C(=O)—O—; —C(=O)—NR$^1$—, —NR$^1$—C(=O)—; —$C_{1-6}$alkyl-; —O—$C_{1-6}$alkyl-; —$C_{1-6}$alkyl-O—; —NR$^1$—$C_{1-6}$alkyl-; —$C_{1-6}$alkyl-NR$^1$—; —NR$^1$—$C_{1-6}$alkyl-NR$^1$—; —$C_{2-6}$alkenyl-; —$C_{2-6}$alkynyl-; —O—$C_{2-6}$alkenyl-; —$C_{2-6}$alkenyl-O—; —NR$^1$—$C_{2-6}$alkenyl-; —$C_{2-6}$alkenyl-NR$^1$—; —NR$^1$—$C_{2-6}$alkenyl-NR$^1$—; —O—$C_{2-6}$alkynyl-; —$C_{2-6}$alkynyl-O—; —NR$^1$—$C_{2-6}$alkynyl-; —$C_{2-6}$alkynyl-NR$^1$—; —NR$^1$—$C_{2-6}$alkynyl-NR$^1$—; —O—$C_{1-6}$alkyl-O—; —O—$C_{2-6}$alkenyl-O—; —O—$C_{2-6}$alkynyl-O—; —CHOH—; —S—; —S(=O)—; —S(=O)$_2$—; —S(=O)—NR$^1$—; —S(=O)$_2$—NR$^1$—; —NR$^1$—S(=O)—; —NR$^1$—S(=O)$_2$—; —S—$C_{1-6}$alkyl-; —$C_{1-6}$alkyl-S—; —S—$C_{2-6}$alkenyl-; —$C_{2-6}$alkenyl-S—; —S—$C_{2-6}$alkynyl-; —$C_{2-6}$alkynyl-S—; or a direct bond;

Z is a direct bond, $C_{1-6}$alkanediyl, $C_{2-6}$alkenediyl, $C_{2-6}$alkynediyl; —O—; —O—$C_{1-6}$alkyl-; —C(=O)—; —C(=O)—O—; —O—C(=O)—; —S(=O)—; —S(=O)$_2$—; —NR$^1$—; —NR$^1$—$C_{1-6}$alkyl-; —NR$^1$—C(=O)—; —O—C(=O)—NR$^1$—; —NR$^1$C(=O)—O—; —S(=O)—NR$^1$—; —S(=O)$_2$—NR$^1$—; —NR$^1$—S(=O)—; —NR$^1$—S(=O)$_2$—;

$R^2$ is hydrogen, $C_{1-10}$alkyl, $C_{2-10}$alkenyl, $C_{2-10}$alkynyl, $R^{20}$, each of said groups representing $R^2$ may optionally be substituted where possible with one or more substituents each independently being selected from =O; $R^{15}$; hydroxy; halo; nitro; cyano; $R^{15}$—O—; SH; $R^{15}$—S—; formyl; carboxyl; $R^{15}$—C(=O)—; $R^{15}$—O—C(=O)—; $R^{15}$—C(=O)—O—; $R^{15}$—O—C(=O)—O—; —SO$_3$H; $R^{15}$—S(=O)—; $R^{15}$—S(=O)$_2$—; $R^5R^6$N; $R^5R^6$N—$C_{1-6}$alkyl; $R^5R^6$N—$C_{1-6}$alkyloxy; $R^{5a}R^{6a}$N—C(=O)—; $R^5R^6$N—S(=O)$_n$—; $R^5R^6$N—S(=O)$_n$—NH—; $R^{15}$—C(=O)—NH—;

$R^3$ is hydrogen; hydroxy; halo; $C_{1-6}$alkyl; $C_{1-6}$alkyl substituted with cyano, hydroxy or —C(=O)R$^7$; $C_{2-6}$alkenyl; $C_{2-6}$alkenyl substituted with one or more halogen atoms or cyano; $C_{2-6}$alkynyl; $C_{2-6}$alkynyl substituted with one or more halogen atoms or cyano; $C_{1-6}$alkylthio; $C_{1-6}$alkyloxycarbonyl; carboxyl; cyano; nitro; amino; mono- or di($C_{1-6}$alkyl)amino; polyhalo$C_{1-6}$alkyl; polyhalo$C_{1-6}$alkylthio; $R^{21}$; $R^{21}$—$C_{1-6}$alkyl; $R^{21}$—

O—; $R^{21}$—S—; $R^{21}$—C(=O)—; $R^{21}$—S(=O)$_p$—; $R^7$—S(=O)$_p$—; $R^7$—C(=O)—; —C(=O)NHNH$_2$; $R^7$—C(=O)—NH—; $R^{21}$—C(=O)—NH—; —C(=NH)$R^7$; —C(=NH)$R^{21}$;

$R^4$ is tetrahydrofuranyl, dihydrofuranyl, pyrrolinyl, pyrrolidinyl, imidazolyl, imidazolinyl, imidazolidinyl, oxazolyl, pyrimidinyl, pyridyl, piperidinyl, piperazinyl, pyridazinyl, triazinyl, morpholinyl, dioxolanyl or dioxanyl, each of said heterocycles optionally being substituted where possible with one or more substituents each independently being selected from =O; $R^{15}$; hydroxy; halo; nitro; cyano; $R^{15}$—O—; SH; $R^{15}$—S—; formyl; carboxyl; $R^{15}$—C(=O)—; $R^{15}$—O—C(=O)—; $R^{15}$—C(=O)—O—; $R^{15}$—O—C(=O)—O—; —SO$_3$H; $R^{15}$—S(=O)—; $R^{15}$—S(=O)$_2$—; $R^5R^6$N; $R^5R^6$N—C$_{1-6}$alkyl; $R^5R^6$N—C$_{1-6}$alkyloxy; $R^{5a}R^{6a}$N—C(=O)—; $R^5R^6$N—S(=O)$_n$—; $R^{15}$—C(=O)—NH—;

$R^5$ and $R^6$ each independently are hydrogen or $R^8$;

$R^{5a}$ and $R^{6a}$ each independently are hydrogen, C$_{1-6}$alkyl; C$_{2-6}$alkenyl or C$_{2-6}$alkynyl, each of said groups representing $R^{5a}$ and $R^{6a}$ may optionally be substituted with one or more substituents selected from $R^{12}$, $R^{13}$ and $R^{14}$;

$R^7$ is C$_{1-6}$alkyl, C$_{1-6}$alkyloxy, amino, mono- or di(C$_{1-6}$alkyl)amino or polyhaloC$_{1-6}$alkyl;

$R^8$ is C$_{1-6}$alkyl; C$_{2-6}$alkenyl; C$_{2-6}$alkynyl; a monocyclic, bicyclic or tricyclic saturated carbocycle; a monocyclic, bicyclic or tricyclic partially saturated carbocycle; a monocyclic, bicyclic or tricyclic aromatic carbocycle; a monocyclic, bicyclic or tricyclic saturated heterocycle; a monocyclic, bicyclic or tricyclic partially saturated heterocycle; a monocyclic, bicyclic or tricyclic aromatic heterocycle; C$_{1-6}$alkyl substituted with a monocyclic, bicyclic or tricyclic saturated carbocycle or with a monocyclic, bicyclic or tricyclic partially saturated carbocycle or with a monocyclic, bicyclic or tricyclic aromatic carbocycle or with a monocyclic, bicyclic or tricyclic saturated heterocycle or with a monocyclic, bicyclic or tricyclic partially saturated heterocycle or with a monocyclic, bicyclic or tricyclic aromatic heterocycle; each of said groups representing $R^8$ may optionally be substituted with one or more substituents selected from $R^{12}$, $R^{13}$ and $R^{14}$;

$R^{12}$, $R^{13}$ and $R^{14}$ each independently are hydrogen; $R^{15}$; hydroxy; halo; nitro; cyano; $R^{15}$—O—; SH; $R^{15}$—S—; formyl; carboxyl; $R^{15}$—C(=O)—; $R^{15}$—O—C(=O)—; $R^{15}$—C(=O)—O—; $R^{15}$—O—C(=O)—O—; —SO$_3$H; $R^{15}$—S(=O)—; $R^{15}$—S(=O)$_2$—; $R^{15}R^{16}$N—S(=O)—; $R^{15}R^{16}$N—S(=O)$_2$—;

$R^{15}$ is C$_{1-6}$alkyl, C$_{2-6}$alkenyl, C$_{2-6}$alkynyl, a monocyclic, bicyclic or tricyclic saturated carbocycle; a monocyclic, bicyclic or tricyclic partially saturated carbocycle; a monocyclic, bicyclic or tricyclic aromatic carbocycle; a monocyclic, bicyclic or tricyclic saturated heterocycle; a monocyclic, bicyclic or tricyclic partially saturated heterocycle; a monocyclic, bicyclic or tricyclic aromatic heterocycle; C$_{1-6}$alkyl substituted with a monocyclic, bicyclic or tricyclic saturated carbocycle or with a monocyclic, bicyclic or tricyclic partially saturated carbocycle or with a monocyclic, bicyclic or tricyclic aromatic carbocycle or with a monocyclic, bicyclic or tricyclic saturated heterocycle or with a monocyclic, bicyclic or tricyclic partially saturated heterocycle or with a monocyclic, bicyclic or tricyclic aromatic heterocycle; each of said substituents representing $R^{15}$ may optionally be substituted with one or more substituents selected from $R^{12}$, $R^{13}$ and $R^{14}$;

$R^{16}$ is hydrogen or $R^{15}$;

$R^{20}$ is a monocyclic, bicyclic or tricyclic saturated carbocycle; a monocyclic, bicyclic or tricyclic partially saturated carbocycle; a monocyclic, bicyclic or tricyclic aromatic carbocycle; a monocyclic, bicyclic or tricyclic saturated heterocycle; a monocyclic, bicyclic or tricyclic partially saturated heterocycle; a monocyclic, bicyclic or tricyclic aromatic heterocycle;

$R^{21}$ is a monocyclic, bicyclic or tricyclic saturated carbocycle; a monocyclic, bicyclic or tricyclic partially saturated carbocycle; a monocyclic, bicyclic or tricyclic aromatic carbocycle; a monocyclic, bicyclic or tricyclic saturated heterocycle; a monocyclic, bicyclic or tricyclic partially saturated heterocycle; a monocyclic, bicyclic or tricyclic aromatic heterocycle, each of said carbocycles or heterocycles representing $R^{21}$ may optionally be substituted with one or more substituents selected from $R^{12}$, $R^{13}$ and $R^{14}$;

n is 1 or 2;
m is 1 or 2;
p is 1 or 2;
s is 1 to 3;

aryl is phenyl or phenyl substituted with one, two, three, four or five substituents each independently selected from halo, C$_{1-6}$alkyl, C$_{3-7}$cycloalkyl, C$_{1-6}$alkyloxy, cyano, nitro, polyhaloC$_{1-6}$alkyl and polyhaloC$_{1-6}$alkyloxy;

provided that —X—$R^2$ and/or $R^3$ is other than hydrogen; and provided that $R^4$ is other than optionally substituted pyridyl when ring A represents pyrimidinyl.

Further preferred are those compounds of formula (I) or (I') wherein the compounds are compounds from one of the following formulae:

1)

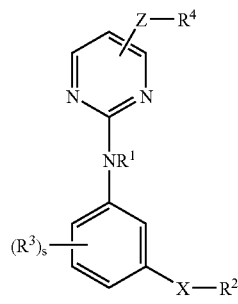

(a-1)

2)

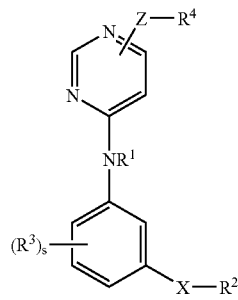

(a-2)

Also preferred are those compounds of formula (a-1) wherein one or where possible more, preferably all of the following restrictions apply:

(a) s is 1 and said $R^3$ substituent is placed at the para position compared to the NR$^1$ linker;

(b) s is 1 and said $R^3$ substituent is placed at the para position of the NR$^1$ linker and is other than C$_{1-6}$alkyloxy or polyhaloC$_{1-6}$alkyloxy;

(c) X is other than a direct bond or $C_{1-6}$alkyl
(d) Z is other than S;
(e) X—$R^2$ is other than hydroxy, $C_{1-6}$alkyl, $C_{1-6}$alkyloxy, trihalomethyl,
trihalomethyloxy, cyano$C_{1-6}$alkyl, aminocarbonyl;
(f) $R^4$ is an optionally substituted 5-membered heterocycle with at least 2 nitrogen atoms;
(g) $R^2$ is other than hydrogen, $C_{1-6}$alkyl, $C_{2-6}$alkenyl, $C_{2-6}$alkynyl, and X is other than O,
S, C(=O), S(=O), S(=O)$_2$, —NH—S(=O)—, —NH—S(=O)$_2$—, —NH—C(=O)—;
(h) $R^2$ is other than hydrogen.

Also preferred are those compounds of formula (a-2) wherein one or more, preferably all of the following restrictions apply
(a) X is other than a direct bond or $C_{1-6}$alkyl;
(b) $R^2$ is other than hydrogen, trifluoromethyl or $C_{1-4}$alkyl;
(c) X—$R^2$ is other than hydroxy, $C_{1-6}$alkyl, $C_{1-6}$alkyloxy, trihalomethyl,
trihalomethyloxy, cyano$C_{1-6}$alkyl, aminocarbonyl;
(d) $R^4$ is an optionally substituted 5-membered heterocycle.

Further interesting compounds are those compounds of formula (I), (I'), (a-1) or (a-2) wherein $R^4$ is an optionally substituted 5-membered heterocycle, in particular an optionally substituted imidazolyl or an optionally substituted triazolyl and/or wherein Z is a direct bond.

Particular preferred compounds of formula (I) or (I') are selected from $N^2$-(1H-indazol-5-yl)-$N^4$-(2,4,6-trimethylphenyl)-2,4-pyrimidinediamine; 4-[[4-(1-methyl-1H-imidazol-2-yl)-2-pyrimidinyl]amino]-2-(phenylmethoxy)-benzonitrile; 4-[[4-(1-methyl-1H-imidazol-2-yl)-2-pyrimidinyl]amino]-benzonitrile; a N-oxide, a pharmaceutically acceptable addition salt, a quaternary amine and a stereochemically isomeric form thereof.

Other preferred compounds of formula (I) or (I') are selected from $N^2$-(6-morpholinyl-4-yl-pyridin-3-yl)-N 4-(2,4,6-trimethyl-phenyl)-2,4-pyrimidinediamine; $N^2$-(3H-benzimidazol-5-yl)-$N^4$-(2,4,6-trimethyl-phenyl)-2,4-pyrimidinediamine; $N^2$-(1H-indazol-6-yl)-$N^4$-(2,4,6-trimethyl-phenyl)-2,4-pyrimidinediamine; $N^2$-(5-bromo-pyridin-2-yl)-N-4-(2,4,6-trimethyl-phenyl)-2,4-pyrimidinediamine; $N^2$-(6-methoxy-pyridin-3-yl)-$N^4$-(2,4,6-trimethyl-phenyl)-2,4-pyrimidinediamine; $N^2$-benzothiazol-6-yl-N 4(2,4,6-trimethyl-phenyl)-2,4-pyrimidinediamine; $N^2$-(1H-indazol-5-yl)—$N^4$-(2,4,6-trimethyl-phenyl)-2,4-pyrimidinediamine; $N^2$-(1H-benzotriazol-5-yl)-N 4-(2,4,6-trimethyl-phenyl)-2,4-pyrimidinediamine; $N^2$-benzo[1,3]dioxol-5-yl-$N^4$(2,4,6-trimethyl-phenyl)-2,4-pyrimidinediamine; $N^2$-(6-chloro-pyridin-3-yl)-$N^4$-(2,4,6-trimethyl-phenyl)-2,4-pyrimidinediamine; $N^2$-(1H-indol-5-yl)-$N^4$-(2,4,6-trimethyl-phenyl)-2,4-pyrimidinediamine; $N^2$-quinolin-6-yl-N-4-(2,4,6-trimethyl-phenyl)-2,4-pyrimidinediamine; 4-[4-[(benzo[1,3]dioxol-5-ylmethyl)-amino]-pyrimidin-2-ylamino]-benzonitrile; 4-[4-[(quinolin-3-methyl)-amino]-pyrimidin-2-ylamino]-benzonitrile; 4-[4-[(furan-2-ylmethyl)-amino]-pyrimidin-2-ylamino]-benzonitrile; 4-[4-[(thiophen-2-ylmethyl)-amino]-pyrimidin-2-ylamino]-benzonitrile; a N-oxide, a pharmaceutically acceptable addition salt, a quaternary amine and a stereochemically isomeric form thereof.

Compounds of formula (I) can be prepared by reacting an intermediate of formula (II) with an intermediate of formula (III) wherein $W_1$ represents a suitable leaving group, such as for example a halo atom, e.g. chloro, bromo and the like, in the presence of a suitable solvent, such as for example N N-dimethylacetamide, acetonitrile, tetrahydrofuran, water, an alcohol, e.g. methanol, ethanol, isopropanol and the like, and optionally in the presence of a suitable acid, such as for example hydrochloric acid and the like.

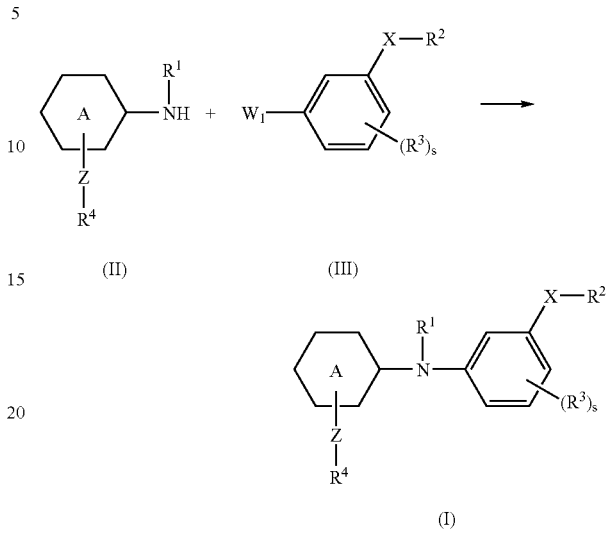

Alternatively, the above reaction may also be performed in the presence of a suitable solvent, such as for example toluene, a suitable catalyst, such as tris (dibenzylidene aceton) dipalladium (0), a suitable ligand such as for example 2,2-bis (diphenylphosphino)-1,1'-binaphthyl, and a suitable base, such as for example sodium tert.butoxide.

Compounds of formula (I) can also be prepared by reacting an intermediate of formula (IV) wherein $W_2$ represents a suitable leaving group, such as for example a halo atom, e.g. chloro and the like, with an intermediate of formula (V) in the presence of a suitable solvent, such as for example toluene, a suitable catalyst, such as tris (dibenzylidene aceton)dipalladium (0), a suitable ligand such as for example 2,2-bis(diphenylphosphino)-1,1'-binaphthyl, and a suitable base, such as for example sodium tert.butoxide.

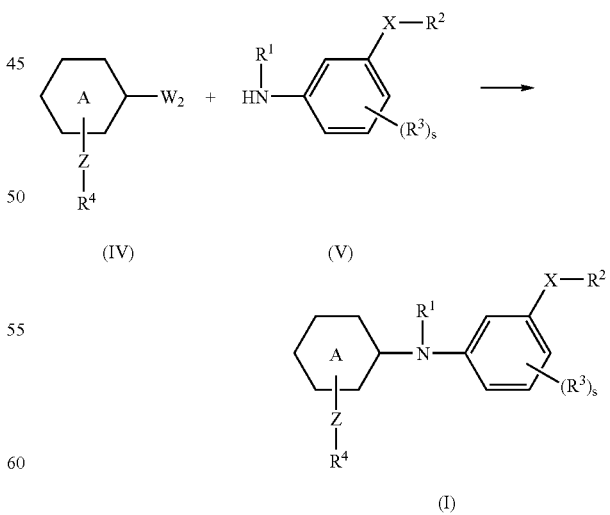

Compounds of formula (I) may also be prepared by reacting an intermediate of formula (VI), wherein $W_3$ represents a suitable leaving group, such as a halo atom, e.g. chloro and the like, with an intermediate of formula (VII) in the presence of a suitable solvent, such as 1,4-dioxane or an alcohol, e.g. methanol, ethanol, isopropanol and the like, or water, optionally in the presence of a suitable acid, such as hydrochloric acid and the like, or a suitable base, such as for example N,N-diisopropylethanamine.

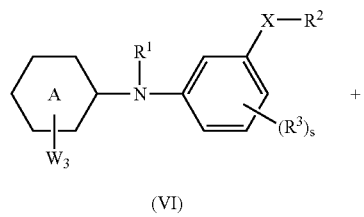

(VI)

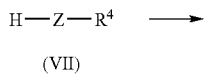

(VII)

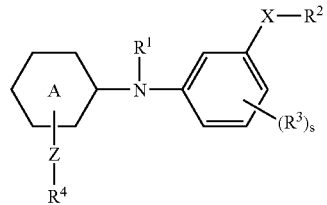

(I)

Compounds of formula (I) wherein Z is C(=O), said compounds being represented by formula (I-a), may be prepared by reacting an intermediate of formula (VIII), wherein $W_4$ represents a suitable leaving group, such as a halo atom, e.g. chloro and the like, or an alcoholate, such as methanolate, ethanolate and the like, with an intermediate of formula (IX) in the presence of a suitable solvent, such as for example an alcohol, e.g. methanol, ethanol and the like.

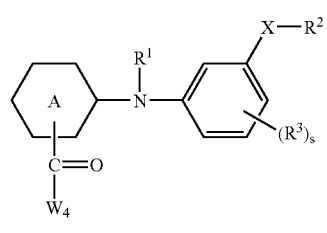

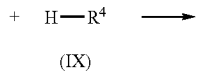

(VIII) (IX)

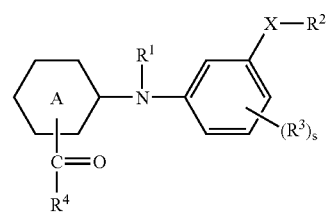

(I-a)

Compounds of formula (I) wherein Z is a direct bond, said compounds being represented by formula (I-b), can be prepared by reacting an intermediate of formula (VI) with an intermediate of formula (X) in the presence of a suitable catalyst, such as for example palladium tetrakis(triphenylphosphine), a suitable base, such as for example disodium carbonate, and a suitable solvent, such as for example acetonitrile and water.

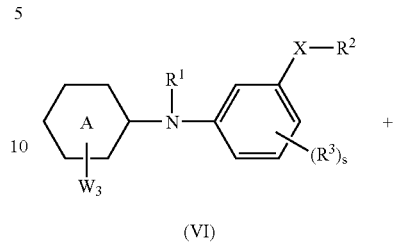

(VI)

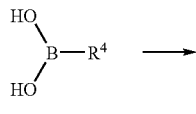

(X)

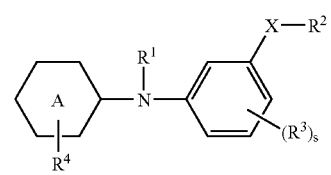

(I-b)

Compounds of formula (I) wherein Z is a direct bond and $R^4$ represents 5-tetrazolyl, said compounds being represented by formula (I-c), can be prepared by reacting an intermediate of formula (XI) with sodium azide in the presence of a suitable salt, such as for example N,N-diethylethanamine hydrochloric acid salt, and a suitable solvent, such as for example 1-methyl-2-pyrrolidinone.

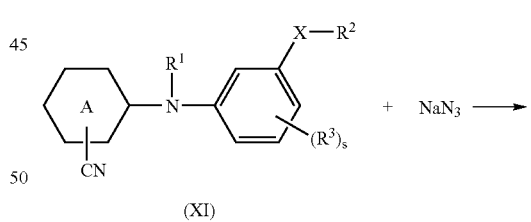

(XI)

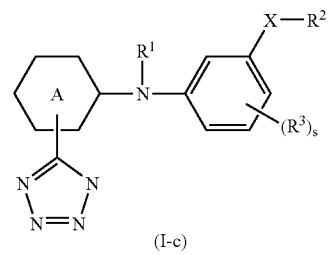

(I-c)

Compounds of formula (I) wherein Z is a direct bond and ring A is pyrimidinyl with the $NR^1$ linker placed in position 2, said compounds being represented by formula (I-d), may be prepared by reacting an intermediate of formula (XX) with an intermediate of formula (XXI) in the presence of a suitable solvent, such as for example N,N-dimethylacetamide and a suitable base, such as for example sodium ethanolate.

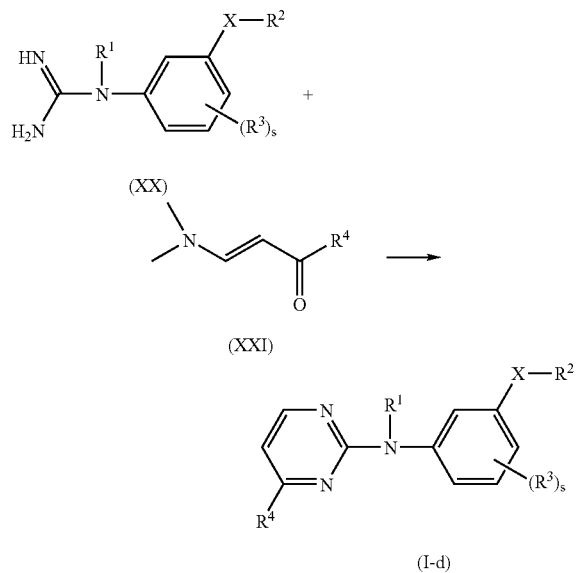

In the above reaction, if $R^4$ in a compound of formula (I-d) represents a heterocycle substituted with amino are aminocarbonyl, than $R^4$ in an intermediate of formula (XXI) may represent a heterocycle substituted with —N=CH—N(CU$_3$)$_2$ or —C(=O)—N=CH—N(CH$_3$)$_2$.

In this and the following preparations, the reaction products may be isolated from the reaction medium and, if necessary, further purified according to methodologies generally known in the art such as, for example, extraction, crystallization, distillation, trituration and chromatography.

The compounds of formula (I) may further be prepared by converting compounds of formula (I) into each other according to art-known group transformation reactions.

The compounds of formula (I) may be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarbo-peroxoic acid, peroxoalkanoic acids, e.g. peroxoacetic acid, alkylhydroperoxides, e.g. t.butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

Compounds of formula (I) wherein $R^3$ is halo, or wherein $R^2$ is substituted with halo, can be converted into a compound of formula (I) wherein $R^3$ is cyano, or wherein $R^2$ is substituted with cyano, by reaction with a suitable cyano-introducing agent, such as sodium cyanide or CuCN, optionally in the presence of a suitable catalyst, such as for example tetrakis(triphenylphosphine)palladium and a suitable solvent, such as N,N-dimethylacetamide or N,N-dimethylformamide. A compound of formula (I) wherein $R^3$ is cyano, or wherein $R^2$ is substituted with cyano, can further be converted into a compound of formula (I) wherein $R^3$ is aminocarbonyl, or wherein $R^1$ is substituted with aminocarbonyl, by reaction with HCOOH, in the presence of a suitable acid, such as hydrochloric acid. A compound of formula (I) wherein $R^3$ is cyano, or wherein $R^2$ is substituted with cyano, can also further be converted into a compound of formula (I) wherein $R^3$ is tetrazolyl, or wherein $R^2$ is substituted with tetrazolyl, by reaction with sodium azide in the presence of ammonium chloride and N,N-dimethylacetoacetamide.

Compounds of formula (I) wherein $R^2$ is substituted with halo, can also be converted into a compound of formula (I) wherein $R^2$ is substituted with mercapto, by reaction with disodium sulfide in the presence of a suitable solvent, such as, for example, 1,4-dioxane.

Compounds of formula (I) wherein $R^2$ is substituted with halo, can also be converted into a compound of formula (I) wherein $R^2$ is substituted with $C_{1-6}$alkylthio, by reaction with a reagent of formula alkaline metal$^+$−S—$C_{1-6}$alkyl e.g. Na$^+$ -S—$C_{1-6}$alkyl in the presence of a suitable solvent, such as dimethylsulfoxide. The latter compounds can further be converted into a compound of formula (I) wherein $R^2$ is substituted with $C_{1-6}$alkyl-S(=O)—, by reaction with a suitable oxidizing agent, such as a peroxide, e.g. 3-chlorobenzenecarboperoxoic acid, in the presence of a suitable solvent, such as an alcohol, e.g. ethanol.

Compounds of formula (I) wherein $R^3$ is halo, or wherein $R^2$ is substituted with halo, can also be converted into a compound of formula (I) wherein $R^3$ is $C_{1-6}$alkyloxy, or wherein $R^2$ is substituted with $C_{1-6}$alkyloxy, by reaction with alcoholate salt, such as, for example, LiOC$_{1-6}$alkyl, in the presence of a suitable solvent, such as an alcohol, e.g. methanol.

Compounds of formula (I) wherein $R^3$ is halo, or wherein $R^2$ is substituted with halo, can also be converted into a compound of formula (I) wherein $R^3$ is hydroxy, or wherein $R^2$ is substituted with hydroxy, by reaction with a suitable carboxylate, e.g. sodium acetate, in a suitable reaction-inert solvent, such as, for example, dimethylsulfoxide, followed by treating the obtained reaction product with a suitable base, such as pyridine, and acetyl chloride.

Compounds of formula (I) wherein $R^3$ is halo, or wherein $R^2$ is substituted with halo, can also be converted into a compound of formula (I) wherein $R^3$ is a monocyclic, bicyclic or tricyclic saturated carbocycle; a monocyclic, bicyclic or tricyclic partially saturated carbocycle; a monocyclic, bicyclic or tricyclic aromatic carbocycle; a monocyclic, bicyclic or tricyclic saturated heterocycle; a monocyclic, bicyclic or tricyclic partially saturated heterocycle; a monocyclic, bicyclic or tricyclic aromatic heterocycle, or wherein $R^2$ is substituted with a monocyclic, bicyclic or tricyclic saturated carbocycle; a monocyclic, bicyclic or tricyclic partially saturated carbocycle; a monocyclic, bicyclic or tricyclic aromatic carbocycle; a monocyclic, bicyclic or tricyclic saturated heterocycle; a monocyclic, bicyclic or tricyclic partially saturated heterocycle; a monocyclic, bicyclic or tricyclic aromatic heterocycle, said substituents being represented by -L, by reaction with H-L in the presence of a suitable base, such as for example sodium hydroxide, dipotassium carbonate, sodium hydride, in the presence of a suitable solvent, such as, for example, 1,4-dioxane, N,N-dimethylacetamide, N,N-dimethylformamide.

Compounds of formula (I) wherein $R^3$ is chloro, or wherein $R^2$ is substituted with chloro, can be converted into a compound of formula (I) wherein $R^3$ is fluoro, or wherein $R^2$ is substituted with fluoro, by reaction with a suitable fluoride salt, such as for example potassium fluoride, in the presence of a suitable solvent, e.g. sulfolane.

Compounds of formula (I) wherein X—$R^2$ is hydrogen and wherein the $R^3$ substituent positioned at the meta position compared to the $NR^1$ linker, is halo, can be converted into a compound of formula (I) wherein said $R^3$ substituent is replaced by X—$R^2$ wherein X is other than a direct bond when $R^2$ is hydrogen, by reaction with H—X—$R^2$ in the presence of a suitable solvent, such as N,N-dimethylacetamide or N,N-dimethylformamide optionally in the presence of a suitable base, such as for example N,N-diisopropylethanamine.

Compounds of formula (I) wherein $R^2$ is substituted with $C_{1-4}$alkyloxy$C_{1-6}$alkyl, can be converted into a compound of formula (I) wherein $R^2$ is substituted with hydroxy$C_{1-6}$alkyl, by dealkylating the ether in the presence of a suitable dealkylating agent, such as, for example, tribromoborane, and a suitable solvent, such as methylene chloride.

Compounds of formula (I) wherein $R^3$ or X—$R^2$ are $C_{1-6}$alkyloxycarbonyl, or wherein $R^2$ is substituted with $C_{1-6}$alkyloxycarbonyl, can be converted into a compound of formula (I) wherein $R^3$ or X—$R^2$ are aminocarbonyl, or wherein $R^2$ is substituted with aminocarbonyl or mono- or di($C_{1-6}$alkyl)aminocarbonyl, by reaction with a suitable agent such as ammonia, $NH_2(C_{1-6}alkyl)$, $AlCH_3[N(C_{1-6}alkyl)_2]Cl$ optionally in the presence of a suitable acid, such as for example hydrochloric acid, and in the presence of a suitable solvent such as an alcohol, e.g. methanol; tetrahydrofuran; N,N-diisopropylethane.

Compounds of formula (I) wherein $R^3$ is hydrogen or wherein $R^2$ is unsubstituted, can be converted into a compound wherein $R^3$ is halo or wherein $R^2$ is substituted with halo, by reaction with a suitable halogenating agent, such as, for example $Br_2$ or 1-(chloromethyl)-4-fluoro-1,4-diazoniabicyclo[2,2,2]octane bis[tetrafluoroborate], in the presence of a suitable solvent, such as tetrahydrofuran, water, acetonitrile, chloroform and optionally in the presence of a suitable base such as N,N-diethylethanamine.

Compounds of formula (I) wherein $R^3$ or —X—$R^2$ are $C_{1-6}$alkyloxycarbonyl or wherein $R^2$ is substituted with $C_{1-6}$alkyloxycarbonyl, can be converted into a compound of formula (I) wherein $R^3$ or X—$R^2$ are hydroxymethyl or wherein $R^2$ is substituted with hydroxymethyl, by reaction with a suitable reducing agent, such as for example $LiAlH_4$.

Compounds of formula (I) wherein —X—$R^2$ is —O—$CH_2$— (optionally substituted)phenyl may be converted into a compound of formula (I) wherein —X—$R^2$ represents OH, by reaction with a suitable reducing agent, such as $H_2$, in the presence of a suitable catalyst, such as for example palladium on charcoal, and a suitable solvent, such as for example an alcohol, e.g. methanol, ethanol and the like, or N,N-dimethylacetamide.

Compounds of formula (I) wherein —X—$R^2$ represents OH, may be converted into a compound of formula (I) wherein —X—$R^2$ represents —O—$X^1$—$R^2$, by reaction with $W_1$—$X_1$—$R^2$ wherein $W_1$ represents a suitable leaving group, such as for example a halo atom, e.g. chloro, and wherein —O—$X_1$ represents those linkers falling under the definition of X which are attached to the phenyl ring via a O atom (in said definition $X_1$ represents that part of the linker wherein the O atom is not included), in the presence of a suitable base, such as for example dipotassium carbonate, and a suitable solvent, such as for example N,N-dimethylacetamide.

Compounds of formula (I) wherein $R^3$ is nitro, or wherein $R^2$ is substituted with nitro, may be converted into a compound of formula (I) wherein $R^3$ is amino or wherein $R^2$ is substituted with amino, by reaction with a suitable reducing agent, such as for example $H_2$, in the presence of a suitable catalyst, such as for example palladium on charcoal, a suitable catalyst poison, such as for example a thiophene solution, and a suitable solvent, such as for example an alcohol, e.g. methanol, ethanol and the like.

Compounds of formula (I) wherein $R^2$ is substituted with $NH_2$, can be converted into a compound of formula (I) wherein $R^2$ is substituted with NH—S($=$O)$_2$—$NR^5R^6$, by reaction with $W_1$—S($=$O)$_2$—$NR^5R^6$ wherein $W_1$ represents a suitable leaving group such as for example a halo atom, e.g. chloro, in the presence of a suitable solvent, such as for example N,N-dimethylacetamide and a suitable base, such as for example N,N-diethylethanamine.

Some of the compounds of formula (I) and some of the intermediates in the present invention may contain an asymmetric carbon atom. Pure stereochemically isomeric forms of said compounds and said intermediates can be obtained by the application of art-known procedures. For example, diastereoisomers can be separated by physical methods such as selective crystallization or chromatographic techniques, e.g. counter current distribution, liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallization or chromatographic techniques, e.g. liquid chromatography and the like methods; and finally converting said separated diastereomeric salts or compounds into the corresponding enantiomers. Pure stereochemically isomeric forms may also be obtained from the pure stereochemically isomeric forms of the appropriate intermediates and starting materials, provided that the intervening reactions occur stereospecifically.

An alternative manner of separating the enantiomeric forms of the compounds of formula (I) and intermediates involves liquid chromatography, in particular liquid chromatography using a chiral stationary phase.

Some of the intermediates and starting materials are known compounds and may be commercially available or may be prepared according to art-known procedures, such as those described in WO 99/50250, WO 00/27825 or EP 0,834,507.

Intermediates of formula (II) wherein $R^1$ is hydrogen, said intermediates being represented by formula (II-a), can be prepared by reducing an intermediate of formula (XII) in the presence of a suitable reducing agent, such as for example $H_2$, a suitable catalyst, such as for example palladium on charcoal, a suitable catalyst poison, such as for example a thiophene solution, and a suitable solvent, such as for example tetrahydrofuran or an alcohol, e.g. methanol, ethanol and the like.

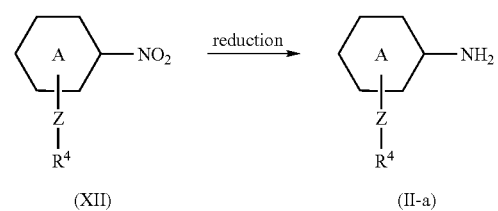

Intermediates of formula (III) can be prepared by reacting an intermediate of formula (XIII) wherein $W_1$ is as defined hereinabove, with an intermediate of formula (XIV) in the presence of a suitable solvent, such as for example acetonitrile or dioxane, and optionally in the presence of a suitable base, such as for example N,N-diisopropylethanamine.

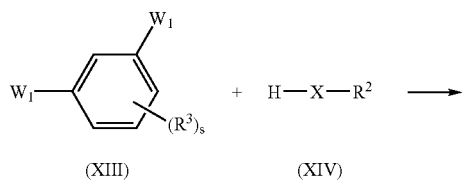

(XIII)  (XIV)

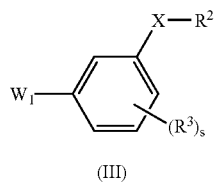

(III)

Intermediates of formula (IV) can be prepared by reacting an intermediate of formula (XV) wherein $W_2$ is as defined hereinabove, with an intermediate of formula (XVI) wherein $W_2$ is as defined hereinabove.

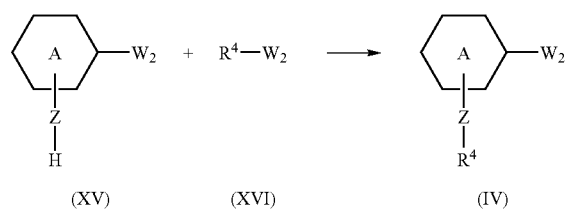

(XV)  (XVI)  (IV)

Intermediates of formula (XVI) can be prepared by reacting an intermediate of formula (XVII) with a leaving group introducing agent of formula (XVIII) wherein $W_2$ represents the leaving group and R represents the remaining of the leaving group introducing agent, such as for example $POCl_3$.

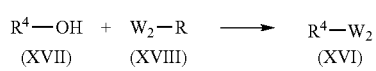

(XVII)  (XVIII)  (XVI)

Intermediates of formula (VI) can be prepared by reacting an intermediate of formula (XIX) wherein $W_3$ is as defined hereinabove, with an intermediate of formula (III) in the presence of a suitable solvent, such as for example an alcohol, e.g. methanol, ethanol, isopropanol and the like, and a suitable acid, such as for example hydrochloric acid.

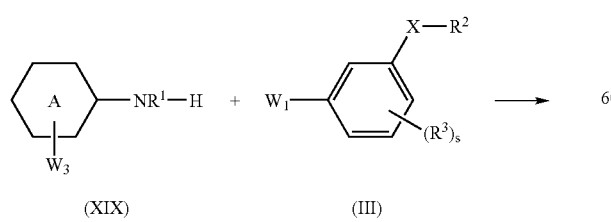

(XIX)  (III)

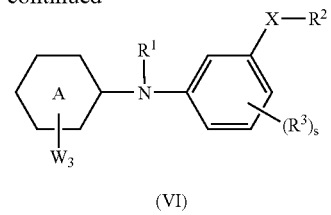

(VI)

Intermediates of formula (VIII) wherein ring A is pyrimidinyl with the $NR^1$ linker in position 2 and $W_4$ represents an alcoholate, i.e. $C_{1-6}alkylO$—, said intermediates being represented by formula (VIII-a), may be prepared by reacting an intermediate of formula (XX) with an intermediate of formula (XXII) in the presence of a suitable solvent, such as for example N,N-dimethylacetamide.

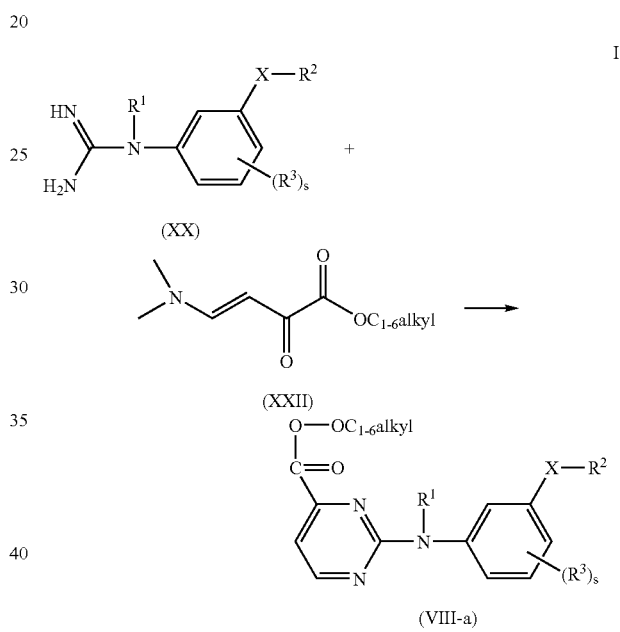

(XX)

(XXII)

(VIII-a)

Intermediates of formula (XXII) can be prepared by reacting an intermediate of formula (XXIII) with 1,1-diethoxy-N,N-dimethyl-methanamine.

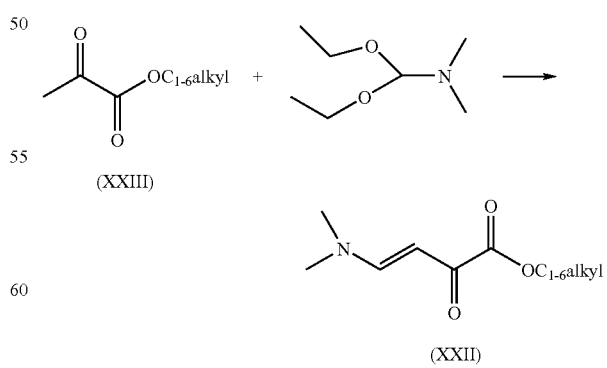

(XXIII)

(XXII)

Intermediates of formula (XX) can be prepared by reacting an intermediate of formula (V) with cyanamide in the presence of a suitable solvent, such as for example diglyme.

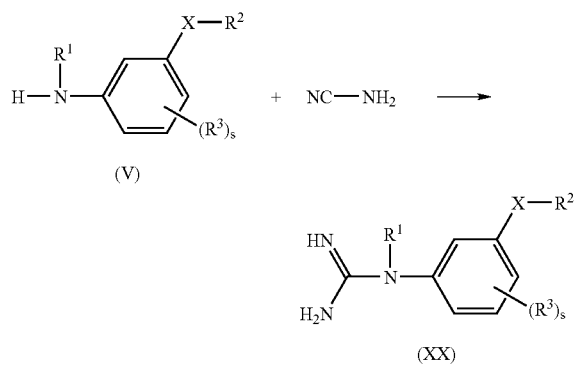

(V)

(XX)

Intermediates of formula (XXI) can be prepared by reacting an intermediate of formula (XXIV) with 1,1-diethoxy-N,N-dimethyl-methanamine.

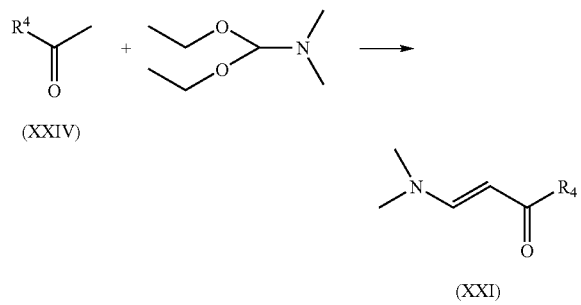

(XXIV)

(XXI)

The compounds of formula (I) or (I') inhibit Glycogen synthase kinase 3 (GSK3), in particular glycogen synthase kinase 3 beta (GSK3β). They are selective Glycogen synthase kinase 3 inhibitors. Specific inhibitory compounds are superior therapeutic agents since they are characterized by a greater efficacy and lower toxicity by virtue of their specificity.

Synonyms for GSK3 are tau protein kinase I (TPK I), FA (Factor A) kinase, kinase FA and ATP-citrate lysase kinase (ACLK).

Glycogen synthase kinase 3 (GSK3), which exists in two isoforms, i.e. GSK3α and GSK3β, is a proline-directed serine/threonine kinase originally identified as an enzyme that phosphorylates glycogen synthase. However, it has been demonstrated that GSK3 phosphorylates numerous proteins in vitro such as glycogen synthase, phosphatase inhibitor I-2, the type-II subunit of cAMP-dependent protein kinase, the G-subunit of phosphatase-1, ATP-citrate lyase, acetyl coenzyme A carboxylase, myelin basic protein, a microtubule-associated protein, a neurofilament protein, an N-CAM cell adhesion molecule, nerve growth factor receptor, c-Jun transcription factor, JunD transcription factor, c-Myb transcription factor, c-Myc transcription factor, L-Myc transcription factor, adenomatous polyposis coli tumor supressor protein, tau protein and β-catenin.

The above-indicated diversity of proteins which may be phosphorylated by GSK3 implies that GSK3 is implicated in numerous metabolic and regulatory processes in cells.

GSK3 inhibitors may therefore be useful in the prevention or treatment of diseases mediated through GSK3 activity such as bipolar disorder (in particular manic depression), diabetes, Alzheimer's disease, leukopenia, FTDP-17 (Fronto-temporal dementia associated with Parkinson's disease), cortico-basal degeneration, progressive supranuclear palsy, multiple system atrophy, Pick's disease, Niemann Pick's disease type C, Dementia Pugilistica, dementia with tangles only, dementia with tangles and calcification, Down syndrome, myotonic dystrophy, Parkinsonism-dementia complex of Guam, aids related dementia, Postencephalic Parkinsonism, prion diseases with tangles, subacute sclerosing panencephalitis, frontal lobe degeneration (FLD), argyrophilic grains disease, subacute sclerotizing panencephalitis (SSPE) (late complication of viral infections in the central nervous system), inflammatory diseases, cancer, dermatological disorders such as baldness, neuronal damage, schizophrenia, pain, in particular neuropathic pain. GSK3 inhibitors can also be used to inhibit sperm motility and can therefore be used as male contraceptives.

In particular, the compounds of the present invention are useful in the prevention or treatment of Alzheimer's disease, diabetes, especially type 2 diabetes (non insulin dependent diabetes).

The major neuropathological landmarks in Alzheimer's disease are neuronal loss, the deposition of amyloid fibers and paired helical filaments (PHF) or neurofibrillary tangles (NFT). Tangle formation appears to be the consequence of accumulation of aberrantly phosphorylated tau protein. This aberrant phosphorylation destabilizes neuronal cytoskeleton, which leads to reduced axonal transport, deficient functioning and ultimately neuronal death. The density of neurofibrillary tangles has been shown to parallel duration and severity of Alzheimer's disease. Reduction of the degree of tau phosphorylation can provide for neuroprotection and can prevent or treat Alzheimer's disease or can slow the progression of the disease. As mentioned hereinabove, GSK3 phosphorylates tau protein. Thus compounds having an inhibitory activity for GSK3 may be useful for the prevention or the treatment of Alzheimer's disease.

Insulin regulates the synthesis of the storage polysaccharide glycogen. The rate-limiting step in the glycogen synthesis is catalyzed by the enzym glycogen synthase. It is believed that glycogen synthase is inhibited by phosphorylation and that insulin stimulates glycogen synthase by causing a net decrease in the phosphorylation of this enzyme. Thus, in order to activate glycogen synthase, insulin must either activate phosphatases or inhibit kinases, or both.

It is believed that glycogen synthase is a substrate for glycogen synthase kinase 3 and that insulin inactivates GSK3 thereby promoting the dephosphorylation of glycogen synthase.

In addition to the role of GSK3 in insulin-induced glycogen synthesis, GSK3 may also play a role in insulin resistance. It is believed that GSK3 dependent Insulin Receptor Substrate-1 phosphorylation contributes to insulin resistance.

Therefore, GSK3 inhibition may result in the increased deposition of glycogen and a concomitant reduction of blood glucose, thus mimicing the hypoglycemic effect of insulin. GSK3 inhibition provides an alternative therapy to manage insulin resistance commonly observed in non insulin dependent diabetes mellitus and obesity. GSK3 inhibitors may thus provide a novel modality for the treatment of type 1 and type 2 diabetes.

GSK3 inhibitors, in particular GSK3β inhibitors, may also be indicated for use in the prevention or the treatment of pain, in particular neuropathic pain.

After axotomy or CCI, neuronal cells die through an apoptotic pathway and the morphological changes correlate with the onset of hyperalgesia and/or allodynia. The induction of apoptosis is probably triggered by a reduced supply of neurotrophic factors as the time course of neuronal loss is positively altered by administration of neurotrophins. GSK, in particular GSK3β, has been shown to be involved in the initiation of the apoptotic cascade and trophic factor withdrawal stimulates the GSK3β apoptosis pathway.

In view of the above, GSK3β inhibitors might reduce signals of and even prevent levels of neuropathic pain.

Due to their GSK3 inhibitory properties, particularly their GSK3β inhibitory properties, the compounds of formula (I) or (I'), their N-oxides, pharmaceutically acceptable addition salts, quaternary amines and stereochemically isomeric forms thereof, are useful to prevent or treat GSK3 mediated diseases, in particular GSK3β mediated diseases, such as bipolar disorder (in particular manic depression), diabetes, Alzheimer's disease, leukopenia, FTDP-17 (Fronto-temporal dementia associated with Parkinson's disease), cortico-basal degeneration, progressive supranuclear palsy, multiple system atrophy, Pick's disease, Niemann Pick's disease type C, Dementia Pugilistica, dementia with tangles only, dementia with tangles and calcification, Down syndrome, myotonic dystrophy, Parkinsonism-dementia complex of Guam, aids related dementia, Postencephalic Parkinsonism, prion diseases with tangles, subacute sclerosing panencephalitis, frontal lobe degeneration (FLD), argyrophilic grains disease, subacute sclerotizing panencephalitis (SSPE) (late complication of viral infections in the central nervous system), inflammatory diseases, cancer, dermatological disorders such as baldness, neuronal damage, schizophrenia, pain, in particular neuropathic pain. The present compounds are also useful as male contraceptives. In general, the compounds of the present invention may be useful in the treatment of warm-blooded animals suffering from disease mediated through GSK3, in particular GSK3β, or they may be useful to prevent warm-blooded animals to suffer from disease mediated through GSK3, in particular GSK3 β. More in particular, the compounds of the present invention may be useful in the treatment of warm-blooded animals suffering from Alzheimer's disease, diabetes, especially type 2 diabetes, cancer, inflammatory diseases or bipolar disorder.

In view of the above described pharmacological properties, the compounds of formula (I) or any subgroup thereof, their N-oxides, pharmaceutically acceptable addition salts, quaternary amines and stereochemically isomeric forms, may be used as a medicine. In particular, the present compounds can be used for the manufacture of a medicament for treating or preventing diseases mediated through GSK3, in particular GSK3β. More in particular, the present compounds can be used for the manufacture of a medicament for treating or preventing Alzheimer's disease, diabetes, especially type 2 diabetes, cancer, inflammatory diseases or bipolar disorder.

In view of the utility of the compounds of formula (I) or (I'), there is provided a method of treating warm-blooded animals, including humans, suffering from or a method of preventing warm-blooded animals, including humans, to suffer from diseases mediated through GSK3, in particular GSK3β, more in particular a method of treating or preventing Alzheimer's disease, diabetes, especially type 2 diabetes, cancer, inflammatory diseases or bipolar disorder. Said method comprises the administration, preferably oral administration, of an effective amount of a compound of formula (I) or (I'), a N-oxide form, a pharmaceutically acceptable addition salt, a quaternary amine or a possible stereoisomeric form thereof, to warm-blooded animals, including humans.

The present invention also provides compositions for preventing or treating diseases mediated through GSK3, in particular GSK3β, comprising a therapeutically effective amount of a compound of formula (I) or (I') and a pharmaceutically acceptable carrier or diluent.

The compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. The compounds of the present invention may also be administered via inhalation or insufflation by means of methods and formulations employed in the art for administration via this way. Thus, in general the compounds of the present invention may be administered to the lungs in the form of a solution, a suspension or a dry powder. Any system developed for the delivery of solutions, suspensions or dry powders via oral or nasal inhalation or insufflation are suitable for the administration of the present compounds.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

The present compounds are orally active compounds, and are preferably orally administered.

The exact dosage, the therapeutically effective amount and frequency of administration depends on the particular compound of formula (I) or (I') used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

When used as a medicament to prevent or treat Alzheimer's disease, the compounds of formula (I) or (I') may be used in combination with other conventional drugs used to combat Alzheimer's disease, such as galantamine, donepezil, rivastigmine or tacrine. Thus, the present invention also relates to the combination of a compound of formula (I) or (I') and another agent capable of preventing or treating Alzheimer's disease. Said combination may be used as a medicine. The present invention also relates to a product containing (a) a compound of formula (I) or (I'), and (b) another agent capable of preventing or treating Alzheimer's disease, as a combined preparation for simultaneous, separate or sequential use in the prevention or treatment of Alzheimer's disease. The different drugs may be combined in a single preparation together with pharmaceutically acceptable carriers.

When used as a medicament to prevent or treat type 2 diabetes, the compounds of formula (I) or (I') may be used in combination with other conventional drugs used to combat type 2 diabetes, such as glibenclamide, chlorpropamide, gliclazide, glipizide, gliquidon, tolbutamide, metformin, acarbose, miglitol, nateglinide, repaglinide, acetohexamide, glimepiride, glyburide, tolazamide, troglitazone, rosiglitazone, pioglitazone, isaglitazone.

Thus, the present invention also relates to the combination of a compound of formula (I) or (I') and another agent capable of preventing or treating type 2 diabetes. Said combination may be used as a medicine. The present invention also relates to a product containing (a) a compound of formula (I) or (I'), and (b) another agent capable of preventing or treating type 2 diabetes, as a combined preparation for simultaneous, separate or sequential use in the prevention or treatment of type 2 diabetes. The different drugs may be combined in a single preparation together with pharmaceutically acceptable carriers.

When used as a medicament to prevent or treat cancer, the compounds of formula (I) or (I') may be used in combination with other conventional drugs used to combat cancer such as platinum coordination compounds for example cisplatin or carboplatin; taxane compounds for example paclitaxel or docetaxel; camptothecin compounds for example irinotecan or topotecan; anti-tumour vinca alkaloids for example vinblastine, vincristine or vinorelbine; anti-tumour nucleoside derivatives for example 5-fluorouracil, gemcitabine or capecitabine; nitrogen mustard or nitrosourea alkylating agents for example cyclophosphamide, chlorambucil, carmustine or lomustine; anti-tumour anthracycline derivatives for example daunorubicin, doxorubicin or idarubicin; HER2 antibodies for example trastzumab; and anti-tumour podophyllotoxin derivatives for example etoposide or teniposide; and antiestrogen agents including estrogen receptor antagonists or selective estrogen receptor modulators preferably tamoxifen, or alternatively toremifene, droloxifene, faslodex and raloxifene; aromatase inhibitors such as exemestane, anastrozole, letrazole and vorozole; differentiating agents for example retinoids, vitamin D and DNA methyl transferase inhibitors for example azacytidine; kinase inhibitors for example flavoperidol and imatinib mesylate or farnesyltransferase inhibitors for example R115777.

Thus, the present invention also relates to the combination of a compound of formula (I) or (I') and another agent capable of preventing or treating cancer. Said combination may be used as a medicine. The present invention also relates to a product containing (a) a compound of formula (I) or (I'), and (b) another agent capable of preventing or treating cancer, as a combined preparation for simultaneous, separate or sequential use in the prevention or treatment of cancer. The different drugs may be combined in a single preparation together with pharmaceutically acceptable carriers.

When used as a medicament to prevent or treat bipolar disorder, the compounds of formula (I) or (I') may be used in combination with other conventional drugs used to combat bipolar disorder such as atypical antipsychotics, anti-epileptica, benzodiazepines, lithium salts, for example olanzapine, risperidone, carbamazepine, valproate, topiramate.

Thus, the present invention also relates to the combination of a compound of formula (I) or (I') and another agent capable of preventing or treating bipolar disorder. Said combination may be used as a medicine. The present invention also relates to a product containing (a) a compound of formula (I) or (I'), and (b) another agent capable of preventing or treating bipolar disorder, as a combined preparation for simultaneous, separate or sequential use in the prevention or treatment of bipolar disorder. The different drugs may be combined in a single preparation together with pharmaceutically acceptable carriers.

When used as a medicament to prevent or treat inflammatory diseases, the compounds of formula (I) or (I') may be used in combination with other conventional drugs used to combat inflammatory diseases such as steroids, cyclooxygenase-2 inhibitors, non-steroidal-anti-inflammatory drugs, TNF-α antibodies, such as for example acetyl salicylic acid, bufexamac, diclofenac potassium, sulindac, diclofenac sodium, ketorolac trometamol, tolmetine, ibuprofen, naproxen, naproxen sodium, tiaprofen acid, flurbiprofen, mefenamic acid, nifluminic acid, meclofenamate, indomethacin, proglumetacine, ketoprofen, nabumetone, paracetamol, piroxicam, tenoxicam, nimesulide, fenylbutazon, tramadol, beclomethasone dipropionate, betamethasone, beclamethasone, budesonide, fluticasone, mometasone, dexamethasone, hydrocortisone, methylprednisolone, prednisolone, prednisone, triamcinolone, celecoxib, rofecoxib, infliximab, leflunomide, etanercept, CPH 82, methotrexate, sulfasalazine.

Thus, the present invention also relates to the combination of a compound of formula (I) or (I') and another agent capable of preventing or treating inflammatory diseases. Said combination may be used as a medicine. The present invention also relates to a product containing (a) a compound of formula (I) or (I'), and (b) another agent capable of preventing or treating inflammatory diseases, as a combined preparation for simultaneous, separate or sequential use in the prevention or treatment of inflammatory disorders. The different drugs may be combined in a single preparation together with pharmaceutically acceptable carriers.

Experimental Part

Hereinafter, "DIPE" is defined as diisopropyl ether, "DMA" is defined as N,N-dimethylacetamide, "DMF" is defined as N,N-dimethylformamide.

A. Preparation of the Intermediate Compounds

EXAMPLE A1

Reaction under Argon atmosphere. 2,4,6-Trimethylaniline (0.0678 mol) was added to 2,4-dichloropyrimidine (0.0664 mol) in 1,4-dioxane (100 ml). N,N-di(1-methylethyl)-ethaneamine (N,N-diisopropylethanamine) (0.0830 mol) was added. The reaction mixture was stirred and refluxed for 4 days and the solvent was evaporated. The residue was dissolved in CH$_2$Cl$_2$, washed with a saturated NaHCO$_3$ solution, then dried (Na$_2$SO$_4$), filtered and the solvent was evaporated to give 17.1 g solid residue. This solid was dissolved in CH$_2$Cl$_2$:hexane (1:1; 150 ml), and the resulting solution was concentrated to 100 ml, then filtered. The residue was purified by column chromatography on KP-Sil (eluent: CH$_2$Cl$_2$). The desired fractions were collected and the solvent was evaporated. The less polar fraction was stirred in CH$_2$Cl$_2$ for 3 hours and filtered, yielding 0.44 g 4-chloro-N-(2,4,6-trimethylphenyl)-2-pyrimidinamine. A second fraction was recrystallized from acetonitrile, filtered off and dried, yielding 2-chloro-N-(2,4,6-trimethyl-phenyl)-4-pyrimidinamine (intermediate 1).

EXAMPLE A2

A mixture of 4-[(4-hydroxy-2-pyrimidinyl)amino]-benzonitrile (0.12 mol) in POCl$_3$ (90 ml) was stirred and refluxed under Argon for 20 minutes. The reaction mixture was slowly poured onto 750 ml ice/water, and the solid was separated by filtration. The solid was suspended in 500 ml water, and the pH of the suspension was adjusted to neutral by adding a 20% NaOH solution. The solid was again separated by filtration, suspended in 200 ml 2-propanone, and 1 L methylene chloride was added. The mixture was heated till all solid had dissolved. After cooling to room temperature, the aqueous layer was separated, and the organic layer was dried over magnesium sulfate. During removal of the drying agent by filtration, a solid formed in the filtrate. Further cooling of the filtrate in the freezer, followed by filtration, yielded 21.38 g of 4-[(4-chloro-2-pyrimidinyl)amino]-benzonitrile (intermediate 2).

EXAMPLE A3 a) The Preparation of Intermediate 3

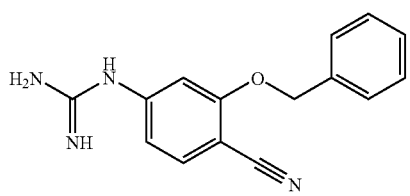

A mixture of 4-amino-2-(2-phenylethoxy)benzonitrile (0.012 mol) in 1,1'-oxybis [2-methoxyethane] (50 ml) was stirred at 100° C., cyanamide (1 ml) was added dropwise. The reaction mixture was stirred at 100° C. for 30 minutes and at room temperature overnight. Extra cyanamide (1 ml) was added and the reaction mixture was stirred at 100° C. for 24 hours. Extra cyanamide (1 ml) was added and the reaction mixture was stirred further at 100° C. for 24 hours. The solvent was evaporated. The residue (6.3 g) was purified by high-performance liquid chromatography over Hyperprep C18 HS BDS (eluent: (0.5% NH$_4$Ac in H$_2$O/CH$_3$CN 90/10)/MeOH/CH$_3$CN 75/25/0; 0/50/50; 0/0/100). The first fraction was collected and the solvent was evaporated, yielding 1.36 g (42.6%) of intermediate 3.

b) The Preparation of Intermediate 4

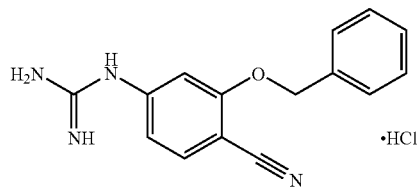

Cyanamide (0.0444 mol) was added portionwise at 80° C. to a solution of 4-amino-2-(phenylmethoxy)-benzonitrile hydrochloric acid (1:1) (0.0444 mol) in 1,1'-oxybis[2-methoxyethane] (90 ml). The mixture was stirred at 100° C. for 3 hours, cooled to room temperature and poured out into ice water. The precipitate was filtered. The filtrate was evaporated. The residue was taken up in CH$_2$Cl$_2$ and crystallized. The precipitate was filtered off and dried, yielding 12.5 g of intermediate 4 (90%) 9 mp. 132° C.).

EXAMPLE A4 a) The Preparation of Intermediate 5

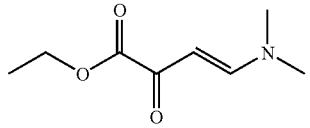

1,1-Diethoxy-N,N-dimethylmethanamine (0.153 mol) was added over 15 minutes to ethyl 2-oxopropanoate (0.153 mol) at room temperature while vigorously stirring. The temperature was kept below 30° C. The reaction mixture was heated to 80° C. for 24 hours. The residue was purified by distillation, yielding 9.8 g (37.4%) of intermediate 5.

EXAMPLE A5

The Preparation of Intermediate 6

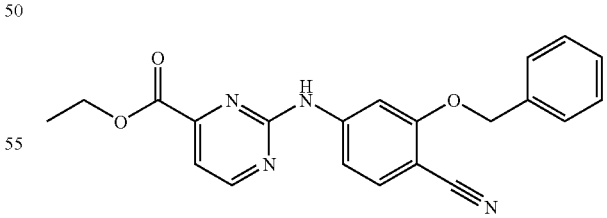

To a solution of intermediate 3 (0.00477 mol) in DMA (30 ml), intermediate 5 (0.0057 mol) was added. The reaction mixture was stirred for 1 hour at room temperature and overnight at 100° C. This mixture was again stirred at 100° C. for 24 hours and then cooled to room temperature. The residue was poured out in a saturated NaCl-solution (300 ml), filtered and washed with H$_2$O. The precipitate was dissolved in 2-propanone and this solution was concentrated in vacuum. The obtained solid was crystallized from EtOH, filtered and dried at 40° C. under vacuum, yielding 0.64 g (35.8%) of intermediate 6.

EXAMPLE A6 a) The Preparation of Intermediate 7

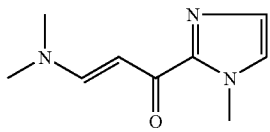

1-(1-Methyl-1H-imidazol-2-yl)ethanone (0.0028 mol) in 1,1-diethoxy-N,N-dimethylmethanamine (10 ml) was stirred and refluxed for 12 hours; then allowed to cool to room temperature. The precipitate was filtered off and dried (50° C., vacuum), yielding 0.42 g (82.3%) of intermediate 7.

b) The Preparation of Intermediate 8

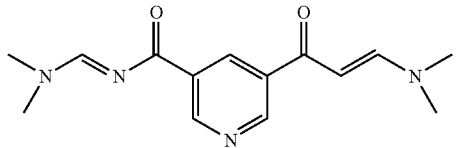

A mixture of 5-acetyl-3-pyridinecarboxamide in DMF/DMA (100 ml) was stirred at 80° C. overnight. The precipitate was filtered off and dried (vacuum), yielding 4 g of intermediate 8.

B. Preparation of the Final Compounds

EXAMPLE B1

The Preparation of Compound 1

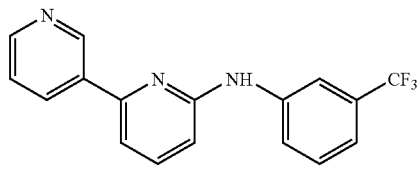

A suspension of 6-bromo-2,3'-bipyridine (0.00042 mol), tris (dibenzylidene aceton)dipalladium (0) (0.0085 mmol), 2,2-bis(diphenylphosphino)-1,1'-binaphthyl (0.0128 mmol) and sodium tert. butoxide (0.00051 mol) in toluene (4 ml) was degassed with $N_2$. 3-(Trifluoromethyl)-benzenamine (0.00051 mol) was added while stirring at room temperature. The resulting reaction mixture was stirred for 18 hours at 90° C. The reaction mixture was washed with water (1 ml), then filtered through Extrelut and the filtrate was evaporated, yielding 0.027 g of compound 1.

EXAMPLE B2 a) The Preparation of Compound 2

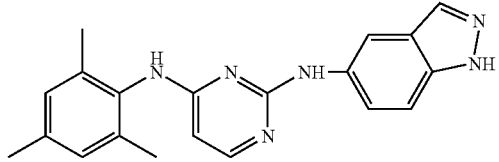

A mixture of methanol (4 ml), water (4 ml) and HCl/2-propanol (0.2 ml) was added to a mixture of intermediate 2 (0.000242 mol) and 1H-indazol-5-amine (0.000242 mol). The reaction mixture was stirred overnight at 60° C. The desired compound was isolated and purified by high performance liquid chromatography over RP C-18 (eluent: (0.5% $NH_4OAc$ in $H_2O/CH_3CN$ 90/10)/$CH_3OH/CH_3CN$ 70/15/15; 0/50/50; 0/0/100). The desired fractions were collected and the solvent was evaporated, yielding 0.017 g of compound 2.

b) The Preparation of Compound 3

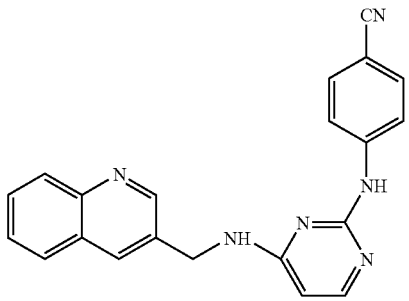

A mixture of intermediate 2 (0.000325 mol), 3-quinolinemethanamine (0.000357 mol) and N,N-diisopropylethanamine (0.0005 mmol) in 1,4-dioxane (4 ml) was stirred at 95° C. for 3 days. The solvent was evaporated and the residue was taken up in methylene chloride. Water (1 ml) was added. The mixture was stirred for 30 minutes; then extracted through Extrelut. The Extrelut was washed twice with methylene chloride. The extract was purified by high performance liquid chromatography over silica gel (eluent: methylene chloride/methanol 100/0; 90/10). The desired fractions were collected and the solvent was evaporated, yielding 0.048 g of compound 3.

EXAMPLE B3 b) The Preparation of Compound 4

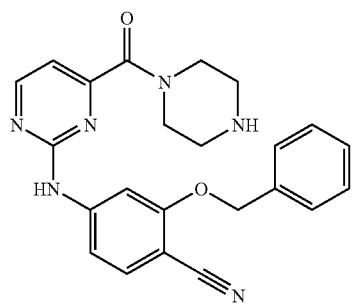

A mixture of intermediate 6 (0.002 mol) and piperazine (0.002 mol) in methanol (15 ml) was stirred at room temperature for 1 day; then stirred at 50° C. for 1 day. The solvent was evaporated. The residue was dissolved in CH$_2$Cl$_2$/MeOH (95/5) and washed with H$_2$O. The separated organic layer was dried (MgSO$_4$), filtered and the solvent was evaporated. The residue was purified over silica gel on a glass filter (eluent: CH$_2$Cl$_2$/MeOH 92.5/7.5). The desired fractions were collected and the solvent was evaporated. The residue was stirred in diethyl ether. The precipitate was filtered off, washed and dried (50° C., vacuum), yielding 0.32 g of compound 4.

EXAMPLE B4 d) The Preparation of Compound 5

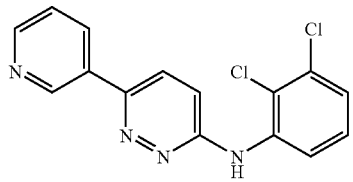

A mixture of 6-chloro-N-(2,3-dichlorophenyl)-3-pyridazinamine (0.00037 mol) and palladium tetrakis(triphenylphosphine) (0.000018 mol) in acetonitrile (10 ml) was stirred (and degassed) under N$_2$ atmosphere and heated to 90° C. A solution of 3-pyridinylboronic acid (2 equiv, 0.00074 mol) in 0.4 M Na$_2$CO$_3$ in H$_2$O (10 ml) (previously degassed under N$_2$) was added dropwise and the resulting reaction mixture was stirred for 18 hours under N$_2$ atmosphere. The mixture was filtered warm and the filter residue was washed with CH$_3$CN (1 ml). The filtrate was diluted with CH$_2$Cl$_2$ (4 ml), then filtered/dried through Extrelut and the filtrate was evaporated. The residue was purified by preparative column chromatography. The product fractions were collected and the solvent was evaporated, yielding 0.027 g of compound 5.

Example B5 a) The Preparation of Compound 6

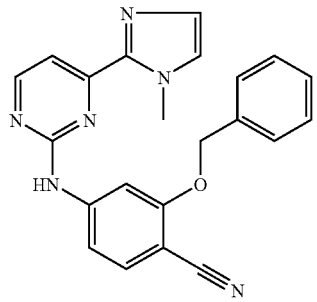

NaOEt (0.68 g) was added to a solution of intermediate 4 (0.01 mol) in DMA (25 ml). The reaction mixture was stirred at room temperature for 1 hour. Intermediate 4 (0.01 mol) was dissolved in DMA (5 ml) and EtOH (15 ml). This solution was added dropwise to the reaction mixture at room temperature. The mixture was stirred at room temperature for 2 hours; then gently heated to 100° C. and stirred for 3 days at this temperature. This fraction was purified by high performance liquid chromatography over hyperprep C$_{18}$ (0.5% NH$_4$OAc in H$_2$O/CH$_3$CN 90/10)/CH$_3$CN 63/37; 25/75; 0/100). The desired fractions were collected and the solvent was evaporated. The residue was suspended in DIPE and stirred overnight. The precipitate was filtered off and dried (40° C., vacuum), yielding 1.34 g (35%) of compound 6.

b) The Preparation of Compound 37' N

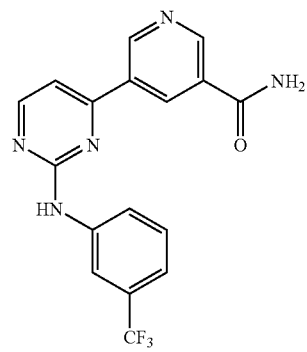

A mixture of guanidine, [3-(trifluoromethyl)phenyl]-, mononitrate (250 mg), intermediate 8 (220 mg), sodium methanolate (0.05 g) and methoxyethanol (20 ml) was stirred at 110° C. for 1 day. The temperature was raised to 160° C. overnight. The reaction mixture was colled, the solvent was evaporated and the residue was suspended in aceton. The precipitate was filtered off, washed and dried (vacuum), yielding 248,1 mg of compound 37.

Example B6

The Preparation of Compound 7

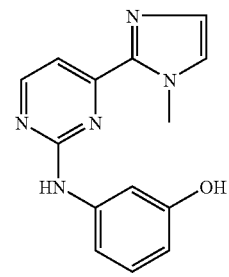

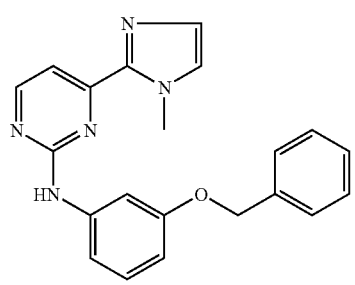

(compound 8) (0.013 mol) (prepared according to Example B5) in methanol and DMA (50 ml) was hydrogenated at 50° C. with Pd/C 10% (1 g) as a catalyst. After uptake of hydrogen (1 equiv), the catalyst was filtered off and the mixture was concentrated till 100 ml. The formed precipitate was filtered off, washed with DIPE and dried, yielding 2.6 g of compound 7.

Tables 1 to 4 list the compounds of formula (I) which were prepared according to one above examples.

TABLE 1

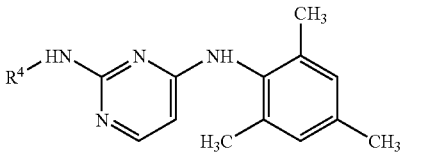

| Co. No. | Ex. No. | R⁴ | Physical data |
|---|---|---|---|
| 9 | B2a | (pyridinyl-morpholinyl group) | |
| 10 | B2a | 1H-benzimidazol-5-yl | |
| 11 | B2a | 1H-indazol-6-yl | |
| 12 | B2a | 5-bromo-2-pyrimidinyl | H2O(1:1) |
| 13 | B2a | 5-bromo-2-pyridinyl | |
| 14 | B2a | 6-methoxy-3-pyridinyl | |
| 15 | B2a | 6-benzothiazolyl | |
| 2 | B2a | 1H-indazol-5-yl | |
| 16 | B2a | 1H-benzotriazol-5-yl | |
| 17 | B2a | 1,3-benzodioxol-5-yl | |
| 18 | B2a | 6-chloro-3-pyridinyl | |
| 19 | B2a | 1H-indol-5-yl | |
| 20 | B2a | 6-quinolinyl | |

TABLE 2

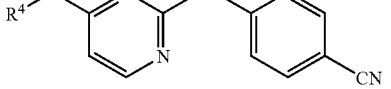

| Co. No. | Ex. No. | R⁴ | Z |
|---|---|---|---|
| 21 | B2b | 2-tetrahydrofuranyl | —CH₂—NH— |
| 22 | B2b | 2-thienyl | —CH₂—NH— |
| 23 | B2b | (dimethoxy-dihydrofuranyl) | —CH₂—NH— |
| 24 | B2b | 2,2-dimethyl-1,3-dioxolan-4-yl | —CH₂—NH— |
| 25 | B2b | 1-ethylpyrrolidin-2-yl | —CH₂—NH— |
| 26 | B2b | 2-furanyl | —CH₂—NH— |
| 3 | B2b | 3-quinolinyl | —CH₂—NH— |
| 27 | B2b | (1-benzylpyrrolidin-3-yl) | —CH₂—NH— |
| 28 | B2b | 4-morpholinyl | —(CH₂)₂—NH— |
| 29 | B2b | 1,3-benzodioxol-5-yl | —CH₂—NH— |
| 30 | B2b | 4-methyl-1-piperazinyl | direct bond |
| 31 | B2b | (4-acetyl-1-piperazinyl) | direct bond |
| 32 | B2b | 4-morpholinyl | direct bond |
| 33 | B5a | 1-methyl-1H-imidazol-2-yl | direct bond |

TABLE 3

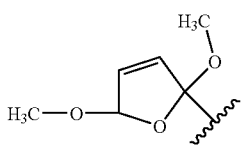

| Co. No. | Ex. No. | R⁴ | R³ᵃ | R³ᵇ | Physical data |
|---|---|---|---|---|---|
| 34 | | (3,5-dimethyl-1H-pyrazol-1-yl) | (pyrimidin-4,6-diyl) | 4-C₆H₁₃ | H |

TABLE 3-continued

| Co. No. | Ex. No. | R⁴ | A | R³ᵃ | R³ᵇ | Physical data |
|---|---|---|---|---|---|---|
| 5 | B4 | 3-pyridinyl | pyridazine-3,6-diyl | 2-Cl | 3-Cl | |
| 35 | B4 | 3-pyridinyl | pyridazine-3,6-diyl | 3-CF₃ | H | |
| 1 | B1 | 3-pyridinyl | pyridine-2,6-diyl | 3-CF₃ | H | |
| 36 | B5b | 2-amino-4-methylpyrimidin-? | pyrimidine-2,4-diyl | 3-CF₃ | H | |
| 37 | B5b | 5-carbamoyl-3-methylpyridin-? | pyrimidine-2,4-diyl | 3-CF₃ | H | |

TABLE 4

| Co. No. | Ex. No. | R⁴ | Z | X-R² | R³ | Physical data |
|---|---|---|---|---|---|---|
| 6 | B5a | 1-methylimidazol-2-yl | db* | —O—CH₂—C₆H₅ | 4-CN | |
| 4 | B3 | 1-piperazinyl | —(C=O)— | —O—CH₂—C₆H₅ | 4-CN | |
| 8 | B5a | 1-methylimidazol-2-yl | db* | —O—CH₂—C₆H₅ | H | |

TABLE 4-continued

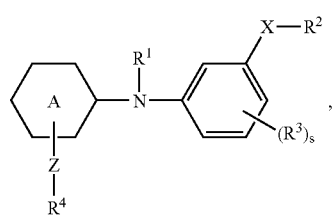

| Co. No. | Ex. No. | R⁴ | Z | X-R² | R³ | Physical data |
|---|---|---|---|---|---|---|
| 7 | B6 | (N-methylimidazol-2-yl) | db* | —O—H | H | |

*db = direct bond

C. Pharmacological Example

The pharmacological activity of the present compounds was examined using the following test.

GSK3beta assays were performed at 25° C. in a 100 µl reaction volume of 25 mM Tris (pH 7.4) containing 10 mM $MgCl_2$, 1 mM DTT, 0.1 mg/ml BSA, 5% glycerol and containing 19 nM GSK3β, 5 µM biotinylated phosphorylated CREB peptide, 1 µM ATP, 2 nM ATP-$P^{33}$ and a suitable amount of a test compound of formula (I) or (I'). After one hour, the reaction was terminated by adding 70 µl of Stop mix (1 mM ATP, 18 mg/ml streptavidin coated PVT SPA bead pH 11.0). The beads to which the phosphorylated CREB peptide is attached were allowed to settle for 30 minutes and the radioactivity of the beads was counted in a microtiterplate scintillation counter and compared with the results obtained in a control experiment (without the presence of a test compound) in order to determine the percentage of GSK3β, inhibition. The $IC_{50}$ value, i.e. the concentration (M) of the test compound at which 50% of GSK3, is inhibited, was calculated from the dose response curve obtained by performing the above-described GSK3β assay in the presence of different amounts of the test compound.

Table 5 lists $pIC_{50}$ values (-log $IC_{50}$ (M)) obtained in the above-described test for the present compounds.

TABLE 5

| Comp. No. | $pIC_{50}$ |
|---|---|
| 22 | 5.74 |
| 24 | 5.36 |
| 25 | 5.72 |
| 26 | 5.81 |
| 2 | 6.28 |
| 17 | 5.30 |
| 20 | 5.44 |
| 6 | 7.01 |
| 4 | 5.53 |
| 33 | 7.11 |

The invention claimed is:

1. A method for treating, in a warm blooded animal in need of such treatment, a disease selected from the group consisting of diabetes, Alzheimer's disease and neuropathic pain, comprising, administering to said animal a therapeutically effective amount of a compound of formula I:

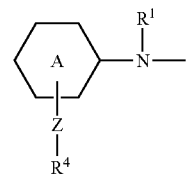

(I)

a pharmaceutically acceptable addition salt or a stereochemically isomeric form thereof, wherein
the moiety

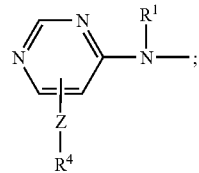

represents a radical of formula $R^1$ is hydrogen; aryl formyl; $C_{1-6}$alkylcarbonyl; $C_{1-6}$alkyl; $C_{1-6}$alkyloxycarbonyl; $C_{1-6}$alkyl substituted with formyl, $C_{1-6}$alkylcarbonyl, $C_{1-6}$alkyloxycarbonyl, $C_{1-6}$alkylcarbonyloxy; $C_{1-6}$alkyloxy$C_{1-6}$alkylcarbonyl optionally substituted with $C_{1-6}$alkyloxycarbonyl;

X is —$NR^1$—; —NH—NH—; —N=N—; —O—; —C(=O)—; —C(=S)—; —O—C(=O)—; —C(=O)—O—; —O—C(=O)—$C_{1-6}$alkyl-; —C(=O)—O—$C_{1-6}$alkyl-; —O—$C_{1-6}$alkyl-C(=O)—; —C(=O)—$C_{1-6}$alkyl-O—; —O—C(=O)—$NR^1$—; —$NR^1$—C(=O)—O—; —O—C(=O)—C(=O)—; —C(=O)—$NR^1$—, —$NR^1$—C(=O)—;

—C(=S)—NR$^1$—, —NR$^1$—C(=S)—; —NR$^1$—C(=O)—NR$^1$—; —NR$^1$—C(=)S—NR$^1$—; —NR$^1$—S(=O)—NR$^1$; NR$^1$—S(=O)$_2$—NR$^1$—; —C$_{1-6}$alkyl-C(=O)—NR$^1$—; —O—C$_{1-6}$alkyl-C(=O)—NR$^1$—; —C$_{1-6}$alkyl-O—C(=O)—NR$^1$—; —C$_{1-6}$alkyl-—O—C$_{1-6}$alkyl-; —C$_{1-6}$alkyl-O—; —NR$^1$—C$_{1-6}$alkyl-; —C$_{1-6}$alkyl-NR$^1$—; —NR$^1$—C$_{1-6}$alkyl-NR$^1$—; —NR$^1$—C$_{1-6}$alkyl-C$_{3-7}$cycloalkyl-; —C$_{2-6}$alkenyl-; —C$_{2-6}$alkynyl-; —O—C$_{2-6}$alkenyl-; —C$_{2-6}$alkenyl-O—; —NR$^1$—C$_{2-6}$alkenyl-; —C$_{2-6}$alkenyl-NR$^1$—; —NR$^1$—C$_{2-6}$alkenyl-NR$^1$—; —NR$^1$—C$_{2-6}$alkenyl-C$_{3-7}$ cycloalkyl-; —O—C$_{2-6}$alkynyl-; —C$_{2-6}$alkynyl-O—; —NR$_1$—C$_{2-6}$alkynyl-; —C$_{2-6}$alkynyl-NR$^1$—; —NR$^1$—C$_{2-6}$alkynyl-NR$^1$—; —NR$^1$—C$_{2-6}$alkynyl-C$_{3-7}$cycloalkyl-; —O—C$_{1-6}$alkyl-O—; —O—C$_{2-6}$alkenyl-O—; —O—C$_{2-6}$alkynyl-O—; —CHOH—; —S—; —S(=O)—; —S(=O)$_2$—; —S(=O)—NR$^1$—; —S(=O)$_2$—NR$^1$—; —NR$^1$—S(=O)—; —NR$^1$—S(=O)$_2$—; —S—C$_{1-6}$alkyl-; —C$_{1-6}$alkyl-S—; —S—S$_{2-6}$alkenyl-; —C$_{2-6}$alkenyl-S—; —S—C$_{2-6}$ alkynyl-; —C$_{2-6}$alkynyl-S—; —O—C$_{1-6}$alkyl-S(=O)$_2$— or a direct bond;

Z is a direct bond, —O—; —S—; —C(=O)—; —C(=O)—O—; —O—C(=O)—; —C(=S)—; —S(=O)—; —S(=O)$_2$—; —NR$^1$—; —NR$^1$—C(=O)—; —O—C(=O)—NR$^1$—; —NR$^1$C(=O)—O—; —NR$^1$—C(=S)—; —S(=O)—NR$^1$—; —S(=O)$_2$—NR$^1$—; —NR$^1$—S(=O)—; —NR$^1$—S(=O)$_2$—; —NR$^1$—(C=O)—NR$^1$—; —NR$^1$—C(=S)—NR$^1$—; —NR$^1$—S(=O)=NR$^1$—; —NR$^1$—S(=O)$_2$—NR$^1$—;

R$^2$ is hydrogen, C$_{1-10}$alkyl, C$_{2-10}$alkenyl, C$_{2-10}$alkynyl, R$^{20}$, each of said groups representing R$^2$ may optionally be substituted where possible with one or more substituents each independently being selected from —S; —O; R$^{15}$; hydroxy; halo; nitro; cyano; R$^{15}$—O—; SH; R$^{15}$—S—; formyl; carboxyl; R$^{15}$—C(=O)—; R$^{15}$—O—C(=O)—; R$^{15}$—C(=O)—O—; R$^{15}$—O—C(=O)—O—; —SO$_3$H; R$^{15}$—S(=O)—; R$^{15}$—S(=O)$_2$—; R$^5$R$^6$N; R$^5$R$^6$N—C$_{1-6}$alkyl; R$^5$R$^6$N—C$_{3-7}$cycloalkyl; R$^5$R$^6$N—C$_{1-6}$alkyloxy; R$^5$R$^6$N—C(=O)—; R$^5$R$^6$N—C(=S)—; R$^5$R$^6$N—C(=O)—NH—; R$^5$R$^6$N—C(=S)—NH—; R$^5$R$^6$N—S(=O)$_n$—; R$^5$R$^6$N—S(=O)$_n$—NH—; R$^{15}$—C(=S)—; R$^{15}$—C(=O)—NH—; R$^{15}$—O—C(=O)—NH—; R$^{15}$—S(=O)$_n$—NH—; R$^{15}$—O—S(=O)$_n$—NH—; R$^{15}$—C(=S)—NH—; R$^{15}$—O—C(=S)—NH—; R$^{17}$R$^{18}$N—Y$_{1a}$—; R$^{17}$R$^{18}$N—Y$_2$—NR$^{16}$—Y$_1$—; R$^{15}$—Y$_2$—NR$^{19}$—Y$_1$—; H—Y$_2$—NR$^{19}$—Y$_1$—;

R$^3$ is hydrogen; halo; C$_{1-6}$alkyl; cyano; or polyhaloC$_{1-6}$alkyl;

R$^4$ is a monocyclic, bicyclic or tricyclic saturated heterocycle; a monocyclic, bicyclic or tricyclic partially saturated heterocycle or a monocyclic, bicyclic or tricyclic aromatic heterocycle, each of said heterocycles optionally being substituted where possible with one or more substituents each independently being selected from =S; =O; R$^{15}$; hydroxy; halo; nitro; cyano; R$^{15}$—O—; SH; R$^{15}$—S—; formyl; carboxyl; R$^{15}$—C(=O)—; R$^{15}$—O—C(=O)—; R$^{15}$—C(=O)—O—; R$^{15}$—O—C(=O)—O—; —SO$_3$H; R$^{15}$—S(=O)—; R$^{15}$—S(=O)$_2$—; R$^5$R$^6$N; R$^5$R$^6$NC$_{1-6}$alkyl; R$^5$R$^6$NC$_{3-7}$cycloalkyl; R$^5$R$^6$NC$_{1-6}$alkyloxy; R$^5$R$^6$N—C(=O)—; R$^5$R$^6$N—C(=S)—; R$^5$R$^6$N—C(=O)—NH—; R$^5$R$^6$N—C(=S)—NH—; R$^5$R$^6$N—S(=O)$_n$—; R$^5$R$^6$N—S(=O)$_n$—NH—; R$^{15}$—C(=S)—; R$^{15}$—C(=O)—NH—; R$^{15}$—O—C(=O)—NH—; R$^{15}$—S(=O)$_n$—NH—; R$^{15}$—O—S(=O)$_n$—NH—; R$^{15}$—C(=S)—NH—; R$^{15}$—O—C(=S)—NH—; R$^{17}$R$^{18}$N—Y$_{1a}$—; R$^{17}$R$^{18}$N—Y$_2$—NR$^{16}$—Y$_1$—; R$^{15}$—Y$_2$—NR$^{19}$—Y$_1$—; H—Y$_2$NR$^{19}$—Y$_1$—;

R$^5$ and R$^6$ each independently are hydrogen, R$^8$, —Y$_1$—NR$^9$—Y$_2$—NR$^{10}$R$^{11}$, —Y$_1$—NR$^9$—Y$_1$—R$^8$, —Y$_1$—NR$^9$R$^{10}$, or R$^5$ and R$^6$ may together with the nitrogen to which they are attached form a saturated or partially saturated monocyclic 3 to 8 membered heterocycle or an aromatic 4 to 8 membered monocyclic heterocycle, each of said heterocycles may optionally be substituted with one or more substituents selected from R$^{12}$, R$^{13}$ and R$^{14}$, or each of said heterocycles may optionally be fused with a benzene ring, said benzene ring being optionally substituted with one or more substituents selected from R$^{12}$, R$^{13}$ and R$^{14}$;

R$^7$ is C$_{1-6}$alkyl, C$_{1-6}$alkyloxy, amino, mono- or di(C$_{1-6}$alkyl)amino or polyhaloC$_{1-6}$alkyl;

R$^8$ is C$_{1-6}$alkyl; C$_{2-6}$alkenyl; C$_{2-6}$alkynyl; a monocyclic, bicyclic or tricyclic saturated carbocycle; a monocyclic, bicyclic or tricyclic partially saturated carbocycle; a monocyclic, bicyclic or tricyclic aromatic carbocycle; a monocyclic, bicyclic or tricyclic saturated heterocycle; a monocyclic, bicyclic or tricyclic partially saturated heterocycle; a monocyclic, bicyclic or tricyclic aromatic heterocycle; C$_{1-6}$alkyl substituted with a monocyclic, bicyclic or tricyclic saturated carbocycle or with a monocyclic, bicyclic or tricyclic partially saturated carbocycle or with a monocyclic, bicyclic or tricyclic aromatic carbocycle or with a monocyclic, bicyclic or tricyclic saturated heterocycle or with a monocyclic, bicyclic or tricyclic partially saturated heterocycle or with a monocyclic, bicyclic or tricyclic aromatic heterocycle; each of said groups representing R$^8$ may optionally be substituted with one or more substituents selected from R$^{12}$, R$^{13}$ and R$^{14}$;

R$^9$, R$^{10}$ and R$^{11}$ each independently are hydrogen or R$^8$, or any two of R$^9$, R$^{10}$ and R$^{11}$ may together be C$_{1-6}$alkanediyl or C$_{2-6}$alkenediyl thereby forming a saturated or partially saturated monocyclic 3 to 8 membered heterocycle or an aromatic 4 to 8 membered monocyclic heterocycle together with the nitrogen atoms to which they are attached, each of said heterocycles may optionally be substituted with one or more substituents selected from R$^{12}$, R$^{13}$ and R$^{14}$;

R$^{12}$, R$^{13}$ and R$^{14}$ each independently are hydrogen; R$^{15}$; hydroxy; halo; nitro; cyano; R$^{15}$—O—; SH; R$^{15}$—S—; formyl; carboxyl; R$^{15}$—C(=O)—; R$^{15}$—O—C(=O)—; R$^{15}$—C(=O)—O—; R$^{15}$—O—C(=O)—O—; —SO$_3$H; R$^{15}$—S(=O)—; R$^{15}$—S(=O)$_2$—; R$^{15}$R$^{16}$N—S(=O)—; R$^{15}$R$^{16}$N—S(=O)$_2$—; R$^{17}$R$^{18}$N—Y$_1$—; R$^{17}$R$^{18}$N—Y$_2$—NR$^{16}$—Y$_1$—; R$^{15}$—Y$_2$—NR$^{19}$—Y$_1$—; H—Y$_2$NR$^{19}$—Y$_1$—; oxo, or any two of R$^{12}$, R$^{13}$ and R$^{14}$ may together be C$_{1-6}$alkanediyl or C$_{2-6}$alkenediyl thereby forming a saturated or partially saturated monocyclic 3 to 8 membered carbo—or heterocycle or an aromatic 4 to 8 membered monocyclic carbo—or heterocycle together with the atoms to which they are attached, or any two of R$^{12}$, R$^{13}$ and R$^{14}$ may together be —O—(CH$_2$)$_r$—O— thereby forming a saturated, partially saturated or aromatic monocyclic 4 to 8 membered carbo or heterocycle together with the atoms to which they are attached;

$R^{15}$ is $C_{1-6}$alkyl, a monocyclic, bicyclic or tricyclic saturated heterocycle; $C_{1-6}$alkyl substituted with a monocyclic, bicyclic or tricyclic saturated carbocycle or with a monocyclic, bicyclic or tricyclic aromatic carbocycle;

$R^{16}$, $R^{17}$, $R^{18}$ and R19 each independently are hydrogen or $R^{15}$, or $R^{17}$ and $R^{18}$, or $R^{15}$ and $R^{19}$ may together be $C_{1-6}$alkanediyl or $C_{2-6}$alkenediyl thereby forming a saturated or partially saturated monocyclic 3 to 8 membered heterocycle or an aromatic 4 to 8 membered monocyclic heterocycle, each of said heterocycles may optionally be substituted with one or more substituents selected from $R^{12}$, $R^{13}$ and $R^{14}$; or $R^{17}$ and $R^{18}$ together with $R^{16}$ may be $C_{1-6}$alkanediyl or $C_{2-6}$alkenediyl thereby forming a saturated or partially saturated monocyclic 3 to 8 membered heterocycle or an aromatic 4 to 8 membered monocyclic heterocycle together with the nitrogen atoms to which they are attached, each of said heterocycles may optionally be substituted with one or more substituents selected from $R^{12}$, $R^{13}$ and $R^{14}$;

$R^{20}$ is a monocyclic, bicyclic or tricyclic saturated carbocycle; a monocyclic, bicyclic or tricyclic partially saturated carbocycle; a monocyclic, bicyclic or tricyclic aromatic carbocycle; a monocyclic, bicyclic or tricyclic saturated heterocycle; a monocyclic, bicyclic or tricyclic partially saturated heterocycle; a monocyclic, bicyclic or tricyclic aromatic heterocycle;

$R^{21}$ is a monocyclic, bicyclic or tricyclic saturated carbocycle; a monocyclic, bicyclic or tricyclic partially saturated carbocycle; a monocyclic, bicyclic or tricyclic aromatic carbocycle; a monocyclic, bicyclic or tricyclic saturated heterocycle; a monocyclic, bicyclic or tricyclic partially saturated heterocycle; a monocyclic, bicyclic or tricyclic aromatic heterocycle, each of said carbocycles or heterocycles representing $R^{21}$ may optionally be substituted with one or more substituents selected from $R^{12}$, $R^{13}$ and $R^{14}$;

$Y_{1a}$ is —$Y_3$—S(=O)—$Y_4$—; —$Y_3$—S(=O)$_2$—$Y_4$—, —$Y_3$—C(=O)—$Y_4$, —$Y_3$—C(=S)—$Y_4$, —$Y_3$—O—$Y_4$—, —$Y_3$—S—$Y_4$—, —$Y_3$—O—C(=O)—$Y_4$— or —$Y_3$—C(=O)—O—$Y_4$—;

$Y_1$ or $Y_2$ each independently are a direct bond, —$Y_3$—S(=O)—$Y_4$—; —$Y_3$—S(=O)$_2$—$Y_4$—, —$Y_3$—C(=O)—$Y_4$—, —$Y_3$—C(=S)—$Y_4$, —$Y_3$—O—$Y_4$, —$Y_3$—S—$Y_4$—, —$Y_3$—O—C(=O)—$Y_4$— or —$Y_3$—C(=O)—O—$Y_4$—;

$Y_3$ or $Y_4$ each independently are a direct bond, $C_{1-6}$alkanediyl, $C_{2-6}$alkenediyl or $C_{2-6}$alkynediyl;

n is 1 or 2;

m is 1 or 2;

p is 1 or 2;

r is 1 to 5;

s is 1 to 3;

aryl is phenyl or phenyl substituted with one, two, three, four or five substituents each independently selected from halo, $C_{1-6}$alkyl, $C_{3-7}$cycloalkyl, $C_{1-6}$alkyloxy, cyano, nitro, polyhalo$C_{1-6}$alkyl and polyhalo$C_{1-6}$alkyloxy;

provided that —X—$R^2$ and/or $R^3$ is other than hydrogen; and provided that

-Z—$R^4$ is other than

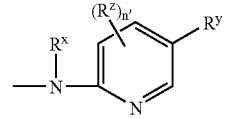

wherein $R^x$ is hydrogen, aryl, $C_{1-6}$alkylcarbonyl, $C_{1-6}$alkyl, $C_{1-6}$alkyloxycarbonyl, $C_{1-6}$alkyl substituted with $C_{1-6}$alkyloxycarbonyl; $R^y$ is halo, $C_{1-6}$alkyl, cyano, aminocarbonyl, nitro, trihalomethyl, trihalomethyloxy or $C_{1-6}$alkyl substituted with cyano or aminocarbonyl; $R^z$ is hydroxyl, halo, $C_{1-6}$alkyl, $C_{1-6}$alkyloxy, cyano, aminocarbonyl, nitro, amino, trihalomethyl, trihalomethyloxy or $C_{1-6}$alkyl substituted with cyano or aminocarbonyl; and n' is 0, 1, 2 or 3; and provided that -Z—$R^4$ is other than $C_{1-6}$alkyl substituted with indolyl which may be substituted with one, two, three, four or five substituents each independently selected from halo, hydroxyl, $C_{1-6}$alkyl, $C_{1-6}$alkyloxy, cyano, aminocarbonyl, $C_{1-6}$alkyloxycarbonyl, formyl, nitro, amino, trihalomethyl, trihalomethyloxy and $C_{1-6}$alkylcarbonyl.

2. The method according to claim 1 wherein

Z is a direct bond, —O—; —O—$C_{1-6}$alkyl-; —C(=O)—; —C(=)—O—; —O—C(=O)—; —C(=S)—; —S(=O)—; —S(=O)$_2$—; —$NR^1$—; —$NR^1$—C(=O)—; —O—C(=O)—$NR^1$—; —$NR^1$C(=O)—O—; —$NR^1$—C(=S)—; —S(=O)—$NR^1$—; —S(=O)$_2$—$NR^1$—; —$NR^1$—S(=O)—; —$NR^1$—S(=O)$_2$—; —$NR^1$—(C=O)—$NR^1$—; —$NR^1$—C(=S)—$NR^1$—; —$NR^1$—S(=O)—$NR^1$—; —$NR^1$—S(=O)$_2$—$NR^1$—;

$R^2$ is hydrogen, $C_{1-10}$alkyl, $C_{2-10}$alkenyl, $C_{2-10}$alkynyl, $R^{20}$, each of said groups representing $R^2$ may optionally be substituted where possible with one or more substituents each independently being selected from =S; =O; $R^{15}$; hydroxy; halo; nitro; cyano; $R^{15}$—O—; SH; $R^{15}$—S—; formyl; carboxyl; $R^{15}$—C(=O)—; $R^{15}$—O—C(=O)—; $R^{15}$—C(=O)—O—; $R^{15}$—O—C(=O)—O—; —SO$_3$H; $R^{15}$—S(=O)—; $R^{15}$—S(=O)$_2$—; $R^5R^6$N; $R^5R^6$N—$C_{1-6}$alkyl; $R^5R^6$N—$C_{3-7}$cycloalkyl; $R^5R^6$N—$C_{1-6}$alkyloxy; $R^{5a}R^{6a}$N—C(=O)—; $R^5R^6$N—C(=S)—; $R^5R^6$N—C(=O)—NH—; $R^5R^6$N—C(=S)—NH—; $R^5R^6$N—S(=O)$_n$—; $R^5R^6$N—S(=O)$_n$—NH—; $R^{15}$—C(=S)—; $R^{15}$—C(=O)—NH—; $R^{15}$—O—C(=O)—NH—; $R^{15}$—S(=O)$_n$—NH—; $R^{15}$—O—S(=O)$_n$—NH—; $R^{15}$—C(=S)—NH—; $R^{15}$—O—C(=S)—NH—; $R^{17}R^{18}$N—$Y_{1a}$—; $R^{17}R^{18}$N—$Y_2$—$NR^{16}$—$Y_1$—; $R^{15}$—$Y_2$—$NR^{19}$—$Y_1$—; H—$Y_2$—$NR^{19}$—$Y_1$—;

$R^4$ is tetrahydrofuranyl, dihydrofuranyl, pyrrolinyl, pyrrolidinyl, imidazolyl, imidazolinyl, imidazolidinyl, oxazolyl, pyrimidinyl, pyridyl, piperidinyl, piperazinyl, pyridazinyl, triazinyl, morpholinyl, dioxolanyl or dioxanyl, each of said heterocycles optionally being substituted where possible with one or more substituents each independently being selected from =S; =O; $R^{15}$; hydroxy; halo; nitro; cyano; $R^{15}$—O—; SH; $R^{15}$—S—; formyl; carboxyl; $R^{15}$—C(=O)—; $R^{15}$—O—C(=O)—; $R^{15}$—C(=O)—O—; $R^{15}$—O—C(=O)—O—; —SO$_3$H; $R^{15}$—S(=O)—; $R^{15}$—S(=O)$_2$—;

$R^5R^6N$; $R^5R^6NC_{1-6}$alkyl; $R^5R^6NC_{3-7}$cycloalkyl; $R^5R^6NC_{1-6}$alkyloxy; $R^5R^6N$—C(=O)—; $R^5R^6N$—C(=S)—; $R^5R^6N$—C(=O)—NH—; $R^5R^6N$—C(=S)—NH—; $R^5R^6N$—S(=O)$_n$—; $R^5R^6N$—S(=O)$_n$—NH—; $R^{15}$—C(=S)—; $R^{15}$—C(=O)—NH—; $R^{15}$—O—C(=O)—NH—; $R^{15}$—S(=O)$_n$—NH—; $R^{15}$—O—S(=O)$_n$—NH—; $R^{15}$—C(=S)—NH—; $R^{15}$—O—C(=S)—NH—; $R^{17}R^{18}N$—$Y_{1a}$—; $R^{17}R^{18}N$—$Y_2$—$NR^{16}$—$Y_1$—; $R^{15}$—$Y_2$—$NR^{19}$—$Y_1$—; H—$Y_2$—$NR^{19}$—$Y_1$—;

$R^{5a}$ and $R^{6a}$ each independently are hydrogen, $C_{1-6}$alkyl; $C_{2-6}$alkenyl or $C_{2-6}$alkynyl, each of said groups representing $R^{5a}$ and $R^{6a}$ may optionally be substituted with one or more substituents selected from $R^{12}$, $R^{13}$ and $R^{14}$.

3. The method according to claim 1 wherein $R^4$ is a 5-membered aromatic heterocycle optionally being substituted where possible with one or more substituents each independently being selected from =S; =O; $R^{15}$; hydroxy; halo; nitro; cyano; $R^{15}$—O—; SH; $R^{15}$—S—; formyl; carboxyl; $R^{15}$—C(=O)—; $R^{15}$—O—C(=O)—; $R^{15}$—C(=O)—O—; $R^{15}$—O—C(=O)—O—; —SO$_3$H; $R^{15}$—S(=O)—; $R^{15}$—S(=O)$_2$—; $R^5R^6N$; $R^5R^6NC_{1-6}$alkyl; $R^5R^6NC_{3-7}$cycloalkyl; $R^5R^6NC_{1-6}$alkyloxy; $R^5R^6N$—C(=O)—; $R^5R^6N$—C(=S)—; $R^5R^6N$—C(=O)—NH—; $R^5R^6N$—C(=S)—NH—; $R^5R^6N$—S(=O)$_n$—; $R^5R^6N$—S(=O)$_n$—NH—; $R^{15}$—C(=S)—; $R^{15}$—C(=O)—NH—; $R^{15}$—O—C(=O)—NH—; $R^{15}$—S(=O)$_n$—NH—; $R^{15}$—O—S(=O)$_n$—NH—; $R^{15}$—C(=S)—NH—; $R^{15}$—O—C(=S)—NH—; $R^{17}R^{18}N$—$Y_{1a}$—; $R^{17}R^{18}N$—$Y_2$—$NR^{16}$—$Y_1$—; $R^{15}$—$Y_2$—$NR^{19}$—$Y_1$—; H—$Y_2$—$NR^{19}$—$Y_1$—.

4. The method according to claim 3 wherein Z is a direct bond.

5. The method according to claim 1 wherein the compound is $N^2$-(1H-indazol-5-yl)-$N^4$-(2,4,6-trimethylphenyl)-2,4-pyrimidinediamine; a pharmaceutically acceptable addition salt or a stereochemically isomeric form thereof.

6. The method according to claim 1 wherein the compound is $N^2$-(6-morpholinyl-4-yl-pyridin-3-yl)-$N^4$-(2,4,6-trimethyl-phenyl)-2,4-pyrimidinediamine; $N^2$-(3H-benzimidazol-5-yl)-$N^4$-(2,4,6-trimethyl-phenyl)-2,4-pyrimidinediamine; $N^2$-(1H-indazol-6-yl)-$N^4$-(2,4,6-trimethyl-phenyl)-2,4-pyrimidinediamine; $N^2$-(5-bromo-pyridin-2-yl)-$N^4$-(2,4,6-trimethyl-phenyl)-2,4-pyrimidinediamine; $N^2$-(6-methoxy-pyridin-3-yl)-$N^4$-(2,4,6-trimethyl-phenyl)-2,4-pyrimidinediamine; $N^2$-benzothiazol-6-yl-$N^4$-(2,4,6-trimethyl-phenyl)-2,4-pyrimidinediamine; $N^2$-(1H-indazol-5-yl)-$N^4$-(2,4,6-trimethyl-phenyl)-2,4-pyrimidinediamine; $N^2$-(1H-benzotriazol-5-yl)-$N^4$-(2,4,6-trimethyl-phenyl)-2,4-pyrimidinediamine; $N^2$-benzo[1,3]dioxol-5-yl-$N^4$-(2,4,6-trimethyl-phenyl)-2,4-pyrimidinediamine; $N^2$-(6-chloro-pyridin-3-yl)-$N^4$-(2,4,6-trimethyl-phenyl)-2,4-pyrimidinediamine; $N^2$-(1H-indol-5-yl)-$N^4$-(2,4,6-trimethyl-phenyl)-2,4-pyrimidinediamine; $N^2$-quinolin-6-yl-$N^4$-(2,4,6-trimethyl-phenyl)-2,4-pyrimidinediamine; a pharmaceutically acceptable addition salt or a stereochemically isomeric form thereof.

7. The method according to claim 1 wherein
X is a direct bond, —O— or —O—$C_{1-6}$alkyl-;
Z is a direct bond, —$NR^1$— or —C(=O)—;
$R^2$ is hydrogen, or $R^{20}$,
$R^4$ is a monocyclic, bicyclic or tricyclic saturated heterocycle; a monocyclic, bicyclic or tricyclic partially saturated heterocycle or a monocyclic, bicyclic or tricyclic aromatic heterocycle, each of said heterocycles optionally being substituted where possible with one or more substituents each independently being selected from $R^{15}$; $R^{15}$—O—; $R^{15}$—C(=O)—; or halo;
$R^{20}$ is a monocyclic, bicyclic or tricyclic aromatic carbocycle;
s is 1 to 3.

8. The method according to claim 1 wherein the animal is a human.

* * * * *